United States Patent
Chen et al.

(10) Patent No.: US 11,820,820 B2
(45) Date of Patent: Nov. 21, 2023

(54) ANTIBODY CAPABLE OF BLOCKING CD47-SIRPA INTERACTION AND APPLICATION THEREOF

(71) Applicant: CHENGDU CONMED BIOSCIENCES CO., LTD, Chengdu (CN)

(72) Inventors: Bo Chen, Chengdu (CN); Gang Xu, Chengdu (CN); Xuhong Chen, Chengdu (CN); Feng Li, Beijing (CN); Boyan Zhang, Foster City, CA (US); Sijia Huang, Beijing (CN)

(73) Assignee: CHENGDU CONMED BIOSCIENCES CO., LTD., Chengdu (CN)

( * ) Notice: Subject to any disclaimer, the term of this patent is extended or adjusted under 35 U.S.C. 154(b) by 0 days.

(21) Appl. No.: 17/251,411

(22) PCT Filed: Jun. 10, 2019

(86) PCT No.: PCT/CN2019/090587
§ 371 (c)(1),
(2) Date: Dec. 11, 2020

(87) PCT Pub. No.: WO2019/238012
PCT Pub. Date: Dec. 19, 2019

(65) Prior Publication Data
US 2021/0292412 A1    Sep. 23, 2021

(30) Foreign Application Priority Data
Jun. 11, 2018 (CN) .......................... 201810593389.3

(51) Int. Cl.
| C07K 16/28 | (2006.01) |
| A61P 35/00 | (2006.01) |
| A61K 39/00 | (2006.01) |

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/565* (2013.01); *C07K 2317/76* (2013.01)

(58) Field of Classification Search
CPC .......... C07K 16/2803; C07K 2317/565; A61P 35/00; A61K 2039/505
See application file for complete search history.

(56) References Cited

U.S. PATENT DOCUMENTS

| 3,773,919 | A | 11/1973 | Boswell et al. |
| 4,522,811 | A | 6/1985 | Eppstein et al. |
| 7,229,619 | B1 | 6/2007 | Young et al. |
| 2014/0140989 | A1* | 5/2014 | Eckelman .......... C07K 16/2803 424/139.1 |
| 2017/0355756 | A1* | 12/2017 | Julien ...................... A61P 25/00 |

FOREIGN PATENT DOCUMENTS

| CN | 104271757 | 1/2015 | |
| CN | 106084052 | 11/2016 | |
| CN | 107406503 | 11/2017 | |
| CN | 107530421 | 1/2018 | |
| CN | 107955070 | 4/2018 | |
| CN | 107955071 | 4/2018 | |
| JP | 2016507555 | 3/2016 | |
| WO | WO-2008068048 A2 * | 6/2008 | ............. A61P 31/10 |
| WO | WO 2017/049251 | 3/2017 | |
| WO | WO 2017/053423 | 3/2017 | |
| WO | WO 2018/075960 | 4/2018 | |

OTHER PUBLICATIONS

Almagro JC, Fransson J. Humanization of antibodies. Front Biosci. Jan. 1, 2008;13:1619-33. (Year: 2008).*
Chen et al. Enhancement and destruction of antibody function by somatic mutation: unequal occurrence is controlled by V gene combinatorial associations.EMBO J.Jun. 15, 1995; 14(12): 2784-94. (Year: 1995).*
Kussie et al. A single engineered amino acid substitution changes antibody fine specificity.J Immunol. Jan. 1, 1994;152(1):146-52. (Year: 1994).*
Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*
Carrillo et al., "The Multiple Sequence Alignment Problem in Biology," SIAM Journal on Applied Mathematics, Oct. 1988, 48(5), 1073-1082.
Chothia et al., "Canonical structures for the hypervariable regions of immunoglobulins," Journal of molecular biology, Aug. 20, 1987, 196(4): 18 Pages.
Englebienne, "Use of colloidal gold surface plasmon resonance peak shift to infer affinity constants from the interactions between protein antigens and antibodies specific for single or multiple epitopes," Analyst, Jan. 1, 1998, 123(7):1599-1603.
GenBank Accession No. P78324.2, "RecName: Full=Tyrosine-protein phosphatase non-receptor type substrate 1; Short=SHIP substrate 1; Short=SHPS-1; AltName: Full=Brain Ig-like molecule with tyrosine-based activation motifs; Short=Bit; AltName: Full=CD172 antigen-like family member A; AltName: Ful . . . " May 23, 2018, 11 pages.
GenBank Accession No. Q08722.1, "RecName: Full=Leukocyte surface antigen CD47; AltName: Full=Antigenic surface determinant protein OA3; AltName: Full=Integrin-associated protein; Short=IAP; AltName: Full=Protein MER6; AltName: CD_antigen=CD47; Flags: Precursor," May 23, 2018, 7 pages.
Griffin et al., "Computer analysis of sequence data, " InComputer Analysis of Sequence Data 1994, 1-8.

(Continued)

*Primary Examiner* — Aurora M Fontainhas
*Assistant Examiner* — Jennifer A Benavides
(74) *Attorney, Agent, or Firm* — Fish & Richardson P.C.

(57) ABSTRACT

An antibody capable of blocking CD47-SIRPa interaction and an application thereof.

22 Claims, 10 Drawing Sheets
Specification includes a Sequence Listing.

(56) References Cited

OTHER PUBLICATIONS

Liu et al., "Pre-clinical development of a humanized anti-CD47 antibody with anti-cancer therapeutic potential," PloS one, Sep. 21, 2015, 10(9):e0137345, 23 Pages.

Malmqvist, "BIACORE: an affinity biosensor system for characterization of biomolecular interactions," Biochemical Society Transactions, 1999, 27(2), 335-340.

Marasco et al., "Design, intracellular expression, and activity of a human anti-human immunodeficiency virus type 1 gp120 single-chain antibody," Proceedings of the National Academy of Sciences, Aufust 15, 1993, 90(16):7889-7893.

Miller et al., "Design, construction, and in vitro analyses of multivalent antibodies," The Journal of Immunology, May 1, 2003, 170(9): 9 Pages.

Nakamura et al., "Codon usage tabulated from international DNA sequence databases: status for the year 2000," Nucleic acids research, Jan. 1, 2000, 28(1):292.

Nelson et al., "Demystified . . . : monoclonal antibodies," Molecular pathology, Jun. 2000, 53(3):111-17.

PCT International Preliminary Report on Patentability, PCT/CN2019/090587, dated Dec. 15, 2020, 5 Pages.

PCT International Search Report and Written Opinion, PCT/CN2019/090587, dated Sep. 11, 2019, 5 Pages.

Rich et al., Advances in surface plasmon resonance biosensor analysis, Curr Opin Biotechnol, Feb. 2000, 11(1):54-61.

Smith et al., "Demystified . . . recombinant antibodies," Journal of clinical pathology, Sep. 1, 2004, 57(9):912-917.

Welschof et al., "Recombinant antibodies for cancer therapy: methods and protocols," Springer Science & Business Media, 2003, Chapter I; p. 3-25.

Smith, "Biocomputing informatics and genome projects," Academic Press, Jun. 28, 2014, 1 page.

\* cited by examiner

| CD47 antibody | Avidity | | | Affinity | | |
|---|---|---|---|---|---|---|
| | KD (nM) | Kon (1/Ms) | Kdis(1/s) | KD(nM) | Kon(1/Ms) | Kdis(1/s) |
| h15G6VH-v1/VK-v1 | 0.41 | 8.26E+04 | 3.41E-05 | 18 | 2.71E+04 | 4.78E-04 |
| h15G6VH-v5/VK-v1 | 0.2 | 5.66E+04 | 4.00E-05 | 23 | 2.63E+04 | 6.11E-04 |
| h15G6VH-v7/VK-v1 | 0.6 | 6.98E+04 | 4.19E-05 | 41 | 3.55E+04 | 1.47E-03 |
| h15G6VH-v7/VK-v2 | 0.71 | 5.66E+04 | 4.00E-05 | 56 | 3.04E+04 | 1.70E-03 |

SEQUENCE LISTING

<160> NUMBER OF SEQ ID NOS: 180

<210> SEQ ID NO 1
<211> LENGTH: 117
<212> TYPE: PRT
<213> ORGANISM: Mus musculus

<400> SEQUENCE: 1

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Asp
            20                  25                  30

Tyr Ile Asn Trp Val Lys Gln Lys Pro Gly Gln Gly Leu Glu Trp Ile
        35                  40                  45

Gly Trp Ile Tyr Pro Gly Ser Gly Asn Ala Lys Tyr Asn Glu Lys Phe
    50                  55                  60

Lys Gly Lys Ala Thr Leu Ile Val Asp Thr Ser Ser Thr Thr Ala Tyr
65                  70                  75                  80

Met Gln Leu Ser Ser Leu Thr Ser Glu Asp Thr Ala Val Tyr Phe Cys
                85                  90                  95

Ser Arg Arg Arg Glu Asp Ser Phe Asp Tyr Trp Gly Gln Gly Thr Thr
            100                 105                 110

Leu Thr Val Ser Ser
        115

<210> SEQ ID NO 2
<211> LENGTH: 5
<212> TYPE: PRT
<213> ORGANISM: Mus musculus

<400> SEQUENCE: 2

Asp Asp Tyr Ile Asn
1               5

<210> SEQ ID NO 3

```
<211> LENGTH: 17
<212> TYPE: PRT
<213> ORGANISM: Mus musculus

<400> SEQUENCE: 3

Trp Ile Tyr Pro Gly Ser Gly Asn Ala Lys Tyr Asn Glu Lys Phe Lys
1               5                   10                  15
Gly

<210> SEQ ID NO 4
<211> LENGTH: 8
<212> TYPE: PRT
<213> ORGANISM: Mus musculus

<400> SEQUENCE: 4

Arg Arg Glu Asp Ser Phe Asp Tyr
1               5

<210> SEQ ID NO 5
<211> LENGTH: 351
<212> TYPE: DNA
<213> ORGANISM: Mus musculus

<400> SEQUENCE: 5
cagatccagc tgcagcagtc tggacctgag gtggtgaagc ctggggcttc agtgaagata      60
tcctgcaagg cttctggcta caccttcact gacgactata aaactgggt gaagcagaag      120
cctggacagg gacttgagtg gattggatgg atttatcctg gaagcggtaa tgctaagtac     180
aatgagaagt tcaagggcaa ggccacattg attgtagaca catcctccac cacagcctac     240
atgcagctca gcagcctgac atctgaggac actgctgtct atttctgttc aagaaggagg     300
gaggattcct ttgactactg gggccaaggc accactctca cagtctcctc a              351

<210> SEQ ID NO 6
<211> LENGTH: 113
<212> TYPE: PRT
<213> ORGANISM: Mus musculus

<400> SEQUENCE: 6

Asp Phe Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Pro Glu Asp Leu Ala Val Tyr Tyr Cys Gln Gln
                85                  90                  95

Phe Tyr Arg Tyr Pro Leu Thr Phe Gly Ala Gly Thr Lys Leu Glu Leu
            100                 105                 110

Lys

<210> SEQ ID NO 7
<211> LENGTH: 17
<212> TYPE: PRT
<213> ORGANISM: Mus musculus
```

<400> SEQUENCE: 7

Lys Ser Ser Gln Ser Leu Leu Tyr Ser Ser Asn Gln Lys Asn Tyr Leu
1               5                   10                  15

Ala

<210> SEQ ID NO 8
<211> LENGTH: 7
<212> TYPE: PRT
<213> ORGANISM: Mus musculus

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Mus musculus

<400> SEQUENCE: 9

Gln Gln Phe Tyr Arg Tyr Pro Leu Thr
1               5

<210> SEQ ID NO 10
<211> LENGTH: 339
<212> TYPE: DNA
<213> ORGANISM: Mus musculus

<400> SEQUENCE: 10
gactttgtga tgtcacagtc tccatcctcc ctagctgtgt cagtcggaga gaaagttact      60
atgagctgca agtccagtca gagccttta tatagtagca atcaaaagaa ttacttggcc     120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaagcctga agacctggca gtttattact gtcagcaatt ttataggtac    300
ccgctcacgt tcggtgctgg gaccaagctg gagctgaaa                           339

<210> SEQ ID NO 11
<211> LENGTH: 117
<212> TYPE: PRT
<213> ORGANISM: Mus musculus

<400> SEQUENCE: 11

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Leu His Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Arg Arg Glu Asp Ser Phe Asp Tyr Trp Gly Gln Gly Thr Thr
                100                 105                 110

Leu Thr Val Ser Ser

<210> SEQ ID NO 12
<211> LENGTH: 5
<212> TYPE: PRT
<213> ORGANISM: Mus musculus

<400> SEQUENCE: 12

Asp Tyr Tyr Leu His
1               5

<210> SEQ ID NO 13
<211> LENGTH: 17
<212> TYPE: PRT
<213> ORGANISM: Mus musculus

<400> SEQUENCE: 13

Trp Ile Tyr Pro Gly Ser Gly Asn Thr Lys Tyr Asn Glu Lys Phe Lys
1               5                   10                  15

Gly

<210> SEQ ID NO 14
<211> LENGTH: 8
<212> TYPE: PRT
<213> ORGANISM: Mus musculus

<400> SEQUENCE: 14

Arg Arg Glu Asp Ser Phe Asp Tyr
1               5

<210> SEQ ID NO 15
<211> LENGTH: 351
<212> TYPE: DNA
<213> ORGANISM: Mus musculus

<400> SEQUENCE: 15
cagatccagc tgcagcagtc tggacctgag ctggtgaagc ctggggcttc agtgaagata      60
tcctgcaagg cttctggcta caccttcact gactactatc tacactgggt gaagcagagg     120
cctggacagg gacttgagtg gattggatgg atttatcctg gaagcggtaa tactaagtac     180
aatgagaagt tcaagggcaa ggccacattg actgtagaca catcctccag cacagcctac     240
atgcagctca gcagcctgac atctgaggac actgctgtct atttctgtgc aagaaggagg     300
gaggattcct ttgactactg gggccaaggc accactctca cagtctcctc a              351

<210> SEQ ID NO 16
<211> LENGTH: 113
<212> TYPE: PRT
<213> ORGANISM: Mus musculus

<400> SEQUENCE: 16

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Thr Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 17
<211> LENGTH: 17
<212> TYPE: PRT
<213> ORGANISM: Mus musculus

<400> SEQUENCE: 17

Lys Ser Ser Gln Ser Leu Leu Tyr Ser Ser Asn Gln Lys Asn Tyr Leu
1               5                   10                  15

Thr

<210> SEQ ID NO 18
<211> LENGTH: 7
<212> TYPE: PRT
<213> ORGANISM: Mus musculus

<400> SEQUENCE: 18

Trp Ala Ser Thr Arg Glu Ser
1               5

<210> SEQ ID NO 19
<211> LENGTH: 9
<212> TYPE: PRT
<213> ORGANISM: Mus musculus

<400> SEQUENCE: 19

Gln Gln Tyr Tyr Ser Tyr Pro Leu Thr
1               5

<210> SEQ ID NO 20
<211> LENGTH: 339
<212> TYPE: DNA
<213> ORGANISM: Mus musculus

<400> SEQUENCE: 20
gacattgtga tgtcacagtc tccatcctcc ctagctgtgt cagttggaga gaaggttact      60
atgagctgca agtccagtca gagccttttta tatagtagca atcaaaagaa ctacttgacc    120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttatagctat    300
ccgctcacgt tcggtgctgg gaccaagctg gagctgaaa                            339

<210> SEQ ID NO 21
<211> LENGTH: 117
<212> TYPE: PRT
<213> ORGANISM: Mus musculus

<400> SEQUENCE: 21

Gln Val Gln Leu Gln Gln Pro Gly Pro Glu Leu Val Lys Pro Gly Thr
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Lys Pro Gly Gln Gly Leu Glu Trp Ile

```
                35                  40                  45
Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Arg Arg Glu Asp Ser Phe Asp Tyr Trp Gly Gln Gly Thr Thr
                100                 105                 110

Leu Thr Val Ser Ser
        115

<210> SEQ ID NO 22
<211> LENGTH: 5
<212> TYPE: PRT
<213> ORGANISM: Mus musculus

<400> SEQUENCE: 22

Asp Tyr Tyr Ile Asn
1               5

<210> SEQ ID NO 23
<211> LENGTH: 17
<212> TYPE: PRT
<213> ORGANISM: Mus musculus

<400> SEQUENCE: 23

Trp Ile Tyr Pro Gly Ser Gly Asn Thr Lys Tyr Asn Glu Lys Phe Lys
1               5                   10                  15

Gly

<210> SEQ ID NO 24
<211> LENGTH: 8
<212> TYPE: PRT
<213> ORGANISM: Mus musculus

<400> SEQUENCE: 24

Arg Arg Glu Asp Ser Phe Asp Tyr
1               5

<210> SEQ ID NO 25
<211> LENGTH: 351
<212> TYPE: DNA
<213> ORGANISM: Mus musculus

<400> SEQUENCE: 25
caggtccaac tgcagcagcc tggacctgag ctggtgaagc ctgggacttc agtgaagata      60
tcctgcaagg cttctggcta caccttcact gactactata taaactgggt gaagcagaag     120
cctggacagg gacttgagtg gattggatgg atttatcctg gaagcggtaa tactaagtac     180
aatgagaagt tcaagggcaa ggccacattg actgtagaca catcctccag cacagcctac     240
atgcagctca gcagcctgac atctgaggac actgctgtct atttctgtgc aagaaggagg     300
gaggattcct ttgactactg gggccaaggc accactctca cagtctcctc a              351

<210> SEQ ID NO 26
<211> LENGTH: 113
<212> TYPE: PRT
<213> ORGANISM: Mus musculus

<400> SEQUENCE: 26
```

-continued

```
Asp Ile Val Met Ser Gln Ser Pro Ser Ser Leu Ala Val Ser Val Gly
1               5                   10                  15

Glu Lys Val Ala Met Ser Cys Lys Ser Ser Gln Ser Leu Leu Tyr Ser
                20                  25                  30

Ser Asn Gln Lys Asn Tyr Leu Thr Trp Tyr Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys
```

<210> SEQ ID NO 27
<211> LENGTH: 17
<212> TYPE: PRT
<213> ORGANISM: Mus musculus

<400> SEQUENCE: 27

```
Lys Ser Ser Gln Ser Leu Leu Tyr Ser Ser Asn Gln Lys Asn Tyr Leu
1               5                   10                  15

Thr
```

<210> SEQ ID NO 28
<211> LENGTH: 7
<212> TYPE: PRT
<213> ORGANISM: Mus musculus

<400> SEQUENCE: 28

```
Trp Ala Ser Thr Arg Glu Ser
1               5
```

<210> SEQ ID NO 29
<211> LENGTH: 9
<212> TYPE: PRT
<213> ORGANISM: Mus musculus

<400> SEQUENCE: 29

```
Gln Gln Tyr Tyr Ser Tyr Pro Leu Thr
1               5
```

<210> SEQ ID NO 30
<211> LENGTH: 339
<212> TYPE: DNA
<213> ORGANISM: Mus musculus

<400> SEQUENCE: 30

```
gacattgtga tgtcacagtc tccatcctcc ctagctgtgt cagttggaga gaaggttgct      60
atgagctgca gtccagtca gagccttta tatagtagca atcaaaagaa ctacttgacc      120
tggtaccagc agaaaccagg gcagtctcct aaactgctga tttactgggc ttccactagg      180
gaatctgggg tccctgatcg cttcacaggc agtggatctg ggacagattt cactctcacc      240
atcagcagtg tgaaggctga agacctggca gtttattact gtcaacaata ttatagctat      300
ccgctcacgt tcggtgctgg gaccaagctg gagctgaaa                              339
```

<210> SEQ ID NO 31
<211> LENGTH: 117
<212> TYPE: PRT
<213> ORGANISM: Mus musculus

<400> SEQUENCE: 31

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Asn Phe His Trp Val Lys Gln Thr Pro Gly Gln Gly Leu Glu Trp Ile
        35                  40                  45

Gly Thr Phe Tyr Pro Val Asn Gly Asp Thr Ser Tyr Asn Gln Lys Phe
    50                  55                  60

Asp Gly Lys Ala Thr Val Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Thr Arg Ala Met Asp Tyr Trp Gly Gln Gly Thr Ser
            100                 105                 110

Val Thr Val Ser Ser
        115

<210> SEQ ID NO 32
<211> LENGTH: 5
<212> TYPE: PRT
<213> ORGANISM: Mus musculus

<400> SEQUENCE: 32

Asn Tyr Asn Phe His
1               5

<210> SEQ ID NO 33
<211> LENGTH: 17
<212> TYPE: PRT
<213> ORGANISM: Mus musculus

<400> SEQUENCE: 33

Thr Phe Tyr Pro Val Asn Gly Asp Thr Ser Tyr Asn Gln Lys Phe Asp
1               5                   10                  15

Gly

<210> SEQ ID NO 34
<211> LENGTH: 8
<212> TYPE: PRT
<213> ORGANISM: Mus musculus

<400> SEQUENCE: 34

Gly Gly Thr Arg Ala Met Asp Tyr
1               5

<210> SEQ ID NO 35
<211> LENGTH: 351
<212> TYPE: DNA
<213> ORGANISM: Mus musculus

<400> SEQUENCE: 35
caggtccaac tgcagcagcc tggggctgag ctggtgaagc ctggggcctc agtgaagatg      60
tcctgcaagg cttctggcta cacatttacc aattacaatt tcactgggt aaagcagaca     120

-continued

```
cctggacagg gcctggaatg gattggaaca tttttatccag taaatggtga tacttcctac    180
aatcagaagt tcgatggcaa ggccacagtg actgcagaca atcctccag cacagcctac     240 atgcagctca gcagcctgac atctgaggac tctgcggtct attactgtgc aagaggggt    300 acgagggcta tggactactg gggtcaaggg acctcagtca ccgtctcctc a            351
```

<210> SEQ ID NO 36
<211> LENGTH: 112
<212> TYPE: PRT
<213> ORGANISM: Mus musculus

<400> SEQUENCE: 36

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Gly Ile Val His Ser
            20                  25                  30

Asn Gly Asn Thr Tyr Leu Ala Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 37
<211> LENGTH: 16
<212> TYPE: PRT
<213> ORGANISM: Mus musculus

<400> SEQUENCE: 37

```
Arg Ser Ser Gln Gly Ile Val His Ser Asn Gly Asn Thr Tyr Leu Ala
1               5                   10                  15
```

<210> SEQ ID NO 38
<211> LENGTH: 7
<212> TYPE: PRT
<213> ORGANISM: Mus musculus

<400> SEQUENCE: 38

```
Lys Val Ser Asn Arg Phe Ser
1               5
```

<210> SEQ ID NO 39
<211> LENGTH: 9
<212> TYPE: PRT
<213> ORGANISM: Mus musculus

<400> SEQUENCE: 39

```
Phe Gln Gly Ser His Val Pro Tyr Thr
1               5
```

<210> SEQ ID NO 40
<211> LENGTH: 336
<212> TYPE: DNA
<213> ORGANISM: Mus musculus

<400> SEQUENCE: 40

```
gatgttttga tgacccaaac tccactctcc ctgcctgtca gtcttggaga tcaagcctcc    60
```

```
atctcttgca gatctagtca gggcattgta catagtaatg gaaacaccta tttagcatgg    120
tacctgcaga aaccaggcca gtctccaaaa ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tacacgttcg agggggggac caagctggaa ataaaa                              336
```

```
<210> SEQ ID NO 41
<211> LENGTH: 117
<212> TYPE: PRT
<213> ORGANISM: Mus musculus

<400> SEQUENCE: 41
```

Gln Ile Leu Leu Gln Gln Ser Gly Pro Asp Leu Val Lys Pro Gly Ala
1               5                  10                  15

Ser Val Lys Ile Ser Cys Lys Ala Ser Gly Tyr Thr Phe Thr Asp Tyr
            20                  25                  30

Tyr Ile His Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Thr Pro Tyr
65                  70                  75                  80

Met Gln Leu Ser Ser Leu Thr Ser Glu Asp Thr Ala Val Tyr Phe Cys
                85                  90                  95

Thr Arg Arg Arg Glu Asp Ser Phe Asp Tyr Trp Gly Gln Gly Thr Thr
            100                 105                 110

Leu Thr Val Ser Ser
        115

```
<210> SEQ ID NO 42
<211> LENGTH: 5
<212> TYPE: PRT
<213> ORGANISM: Mus musculus

<400> SEQUENCE: 42
```

Asp Tyr Tyr Ile His
1               5

```
<210> SEQ ID NO 43
<211> LENGTH: 17
<212> TYPE: PRT
<213> ORGANISM: Mus musculus

<400> SEQUENCE: 43
```

Trp Ile Tyr Pro Gly Ser Gly Asn Thr Lys Tyr Asn Glu Lys Phe Lys
1               5                   10                  15

Gly

```
<210> SEQ ID NO 44
<211> LENGTH: 8
<212> TYPE: PRT
<213> ORGANISM: Mus musculus

<400> SEQUENCE: 44
```

Arg Arg Glu Asp Ser Phe Asp Tyr
1               5

<210> SEQ ID NO 45
<211> LENGTH: 351
<212> TYPE: DNA
<213> ORGANISM: Mus musculus

<400> SEQUENCE: 45

```
cagatcctgc tgcagcagtc tggacctgac ctggtgaagc ctggggcttc agtgaagatt      60
tcctgcaagg cttctggata caccttcact gactactata tacactgggt gaagcagaag     120
cctggacagg gacttgagtg gattggatgg atttatcctg aagcggtaa tactaagtac      180 aatgagaaat tcaagggcaa ggccacattg actgtagaca catcctccag cacacccta c   240 atgcagctca gcagcctgac atctgaggac actgctgtct atttctgtac aagaaggagg     300
gaggattcct ttgactactg gggccaaggc accactctca cagtctcctc a              351
```

<210> SEQ ID NO 46
<211> LENGTH: 113
<212> TYPE: PRT
<213> ORGANISM: Mus musculus

<400> SEQUENCE: 46

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Phe Tyr Ser Tyr Pro Leu Thr Phe Gly Ala Gly Thr Lys Leu Glu Leu
            100                 105                 110

Lys
```

<210> SEQ ID NO 47
<211> LENGTH: 17
<212> TYPE: PRT
<213> ORGANISM: Mus musculus

<400> SEQUENCE: 47

```
Lys Ser Ser Gln Ser Leu Leu Tyr Ser Ser Asn Gln Lys Asn Tyr Leu
1               5                   10                  15

Ala
```

<210> SEQ ID NO 48
<211> LENGTH: 7
<212> TYPE: PRT
<213> ORGANISM: Mus musculus

<400> SEQUENCE: 48

```
Trp Ala Ser Thr Arg Glu Ser
1               5
```

<210> SEQ ID NO 49
<211> LENGTH: 9
<212> TYPE: PRT
<213> ORGANISM: Mus musculus

<400> SEQUENCE: 49

Gln Gln Phe Tyr Ser Tyr Pro Leu Thr
1               5

<210> SEQ ID NO 50
<211> LENGTH: 339
<212> TYPE: DNA
<213> ORGANISM: Mus musculus

<400> SEQUENCE: 50
gacattgtga tgtcacagtc tccatcctcc ctagctgtgt cagttggaga gaaggttact      60
atgagctgca agtccagtca gagccttttta tatagtagca atcaaaagaa ctacttggcc    120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaatt ttatagctat    300
ccgctcacgt tcggtgctgg gaccaagctg gagctgaaa                            339

<210> SEQ ID NO 51
<211> LENGTH: 117
<212> TYPE: PRT
<213> ORGANISM: Mus musculus

<400> SEQUENCE: 51

Gln Ile Gln Leu Gln Gln Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Met Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Pro Tyr
65                  70                  75                  80

Met Gln Leu Ser Ser Leu Thr Ser Glu Asp Thr Ala Val Tyr Phe Cys
                85                  90                  95

Ala Arg Arg Arg Glu Asp Ser Phe Asp Tyr Trp Gly Gln Val Thr Thr
            100                 105                 110

Leu Thr Val Ser Ser
        115

<210> SEQ ID NO 52
<211> LENGTH: 5
<212> TYPE: PRT
<213> ORGANISM: Mus musculus

<400> SEQUENCE: 52

Asp Tyr Tyr Ile His
1               5

<210> SEQ ID NO 53
<211> LENGTH: 17
<212> TYPE: PRT
<213> ORGANISM: Mus musculus

<400> SEQUENCE: 53

Trp Ile Tyr Pro Gly Ser Gly Asn Thr Lys Tyr Asn Glu Lys Phe Lys
1               5                   10                  15

Gly

<210> SEQ ID NO 54
<211> LENGTH: 8
<212> TYPE: PRT
<213> ORGANISM: Mus musculus

<400> SEQUENCE: 54

Arg Arg Glu Asp Ser Phe Asp Tyr
1               5

<210> SEQ ID NO 55
<211> LENGTH: 351
<212> TYPE: DNA
<213> ORGANISM: Mus musculus

<400> SEQUENCE: 55
cagatccagc tgcagcagtc tggacctgac ctggtgaagc ctggggcttc agtgaagatt     60
tcctgcaagg cttctggata caccttcact gactactata tacactggat gaagcagaag   120
cctggacagg gacttgagtg gattggatgg atttatcctg aagcggtaa tactaagtac    180 aatgagaagt tcaagggcaa ggccacattg actgtagaca catcctccag cacacccta    240 atgcagctca gcagcctgac atctgaggac actgctgtct atttctgtgc aagaaggagg   300
gaagattcct ttgactactg gggccaagtc accactctca cagtctcctc a             351

<210> SEQ ID NO 56
<211> LENGTH: 113
<212> TYPE: PRT
<213> ORGANISM: Mus musculus

<400> SEQUENCE: 56

Asp Ile Val Met Ser Gln Ser Pro Ser Ser Leu Ala Val Ser Val Gly
1               5                   10                  15

Glu Gln Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Arg Ala Glu Asp Leu Ala Val Tyr Tyr Cys Gln Gln
                85                  90                  95

Phe Tyr Ser Tyr Pro Leu Thr Phe Gly Ala Gly Thr Lys Leu Glu Leu
            100                 105                 110

Lys

<210> SEQ ID NO 57
<211> LENGTH: 17
<212> TYPE: PRT
<213> ORGANISM: Mus musculus

<400> SEQUENCE: 57

Lys Ser Ser Gln Ser Leu Leu Tyr Ser Ser Asn Gln Lys Asn Tyr Leu
1               5                   10                  15

Ala

<210> SEQ ID NO 58
<211> LENGTH: 7
<212> TYPE: PRT
<213> ORGANISM: Mus musculus

<400> SEQUENCE: 58

Trp Ala Ser Thr Arg Glu Ser
1               5

<210> SEQ ID NO 59
<211> LENGTH: 9
<212> TYPE: PRT
<213> ORGANISM: Mus musculus

<400> SEQUENCE: 59

Gln Gln Phe Tyr Ser Tyr Pro Leu Thr
1               5

<210> SEQ ID NO 60
<211> LENGTH: 339
<212> TYPE: DNA
<213> ORGANISM: Mus musculus

<400> SEQUENCE: 60
gacattgtga tgtcacagtc tccatcctcc ctagctgtgt cagttggaga gcaggttact     60
atgagctgca gtccagtca gagccttttta tatagtagca atcaaaagaa ctacttggcc    120
tggtaccagc agaaaccagg gcagtctcct aaattgttga tttactgggc atccactagg    180
gaatctgggg tccctgatcg cttcacaggc agtggatctg ggacagattt cactctcacc    240
atcagcagtg tgagggctga agacctggca gtttattact gtcagcaatt ttatagctat    300
ccgctcacgt tcggtgctgg gaccaagctg gagctgaaa                           339

<210> SEQ ID NO 61
<211> LENGTH: 117
<212> TYPE: PRT
<213> ORGANISM: Mus musculus

<400> SEQUENCE: 61

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Ile Phe Thr Asp Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Arg Arg Glu Asp Ser Phe Asp Tyr Trp Gly His Gly Thr Thr
                100                 105                 110

Leu Thr Val Ser Ser
        115

<210> SEQ ID NO 62
<211> LENGTH: 5
<212> TYPE: PRT
<213> ORGANISM: Mus musculus

<400> SEQUENCE: 62

Asp Tyr Tyr Ile His
1               5

<210> SEQ ID NO 63
<211> LENGTH: 17
<212> TYPE: PRT
<213> ORGANISM: Mus musculus

<400> SEQUENCE: 63

Trp Ile Tyr Pro Gly Ser Gly Asn Thr Lys Tyr Asn Glu Lys Phe Lys
1               5                   10                  15

Gly

<210> SEQ ID NO 64
<211> LENGTH: 8
<212> TYPE: PRT
<213> ORGANISM: Mus musculus

<400> SEQUENCE: 64

Arg Arg Glu Asp Ser Phe Asp Tyr
1               5

<210> SEQ ID NO 65
<211> LENGTH: 351
<212> TYPE: DNA
<213> ORGANISM: Mus musculus

<400> SEQUENCE: 65
cagatccagc tgcagcagtc tggacctgag ctggtgaagc ctggggcttc agtgaagata      60
tcctgcaagg cttctggcta catcttcact gactactata tacactgggt gaagcagagg     120
cctggacagg gacttgagtg gattggatgg atttatcctg gaagcggtaa tactaagtac     180
aatgagaagt tcaagggcaa ggccacattg actgtagaca catcctccag cacagcctac     240
atgcagctca gcagcctgac atctgaggac actgctgtct atttctgtgc aagaaggagg     300
gaggattcct ttgactactg gggccatggc accactctca cagtctcctc a              351

<210> SEQ ID NO 66
<211> LENGTH: 113
<212> TYPE: PRT
<213> ORGANISM: Mus musculus

<400> SEQUENCE: 66

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Thr Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr His Cys Gln Gln
                85                  90                  95

Tyr Tyr Ser Tyr Pro Leu Thr Phe Gly Ala Gly Thr Lys Leu Glu Leu
                100                 105                 110

Lys

<210> SEQ ID NO 67
<211> LENGTH: 17
<212> TYPE: PRT
<213> ORGANISM: Mus musculus

<400> SEQUENCE: 67

Lys Ser Ser Gln Ser Leu Leu Tyr Ser Ser Asn Gln Lys Asn Tyr Leu
1               5                   10                  15

Thr

<210> SEQ ID NO 68
<211> LENGTH: 7
<212> TYPE: PRT
<213> ORGANISM: Mus musculus

<400> SEQUENCE: 68

Trp Ala Ser Thr Arg Glu Ser
1               5

<210> SEQ ID NO 69
<211> LENGTH: 9
<212> TYPE: PRT
<213> ORGANISM: Mus musculus

<400> SEQUENCE: 69

Gln Gln Tyr Tyr Ser Tyr Pro Leu Thr
1               5

<210> SEQ ID NO 70
<211> LENGTH: 339
<212> TYPE: DNA
<213> ORGANISM: Mus musculus

<400> SEQUENCE: 70
gacattgtga tgtcacagtc tccatcctcc ctagctgtgt cagttggaga gaaggttact      60
atgagctgca agtccagtca gagccttttta tatagtagca atcaaaagaa ctacttgacc    120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttatcact gtcagcaata ttatagctat    300
ccgctcacgt tcggtgctgg gaccaagctg gagctgaaa                            339

<210> SEQ ID NO 71
<211> LENGTH: 117
<212> TYPE: PRT
<213> ORGANISM: Mus musculus

<400> SEQUENCE: 71

Gln Ile Gln Leu Gln Gln Ser Gly Pro Glu Leu Val Lys Thr Gly Ala
1               5                   10                  15

Ser Val Arg Ile Ser Cys Lys Ala Ser Gly Phe Thr Phe Thr Asp Ser
            20                  25                  30

Tyr Ile Asn Trp Val Lys Gln Arg Pro Gly Gln Gly Leu Gln Trp Ile
        35                  40                  45

Gly Trp Ile Tyr Pro Gly Ser Gly Asn Thr Lys Tyr Asn Glu Lys Phe
    50                  55                  60

Lys Asp Lys Ala Thr Leu Thr Val Asp Thr Ser Ser Ser Thr Ala Tyr
65                  70                  75                  80

```
Met Gln Leu Asn Ser Leu Thr Ser Glu Asp Thr Ala Val Phe Phe Cys
                85                  90                  95

Thr Arg Arg Arg Glu Asp Ser Phe Asp Tyr Trp Gly Gln Gly Thr Thr
            100                 105                 110

Leu Thr Val Ser Ser
            115

<210> SEQ ID NO 72
<211> LENGTH: 5
<212> TYPE: PRT
<213> ORGANISM: Mus musculus

<400> SEQUENCE: 72

Asp Ser Tyr Ile Asn
1               5

<210> SEQ ID NO 73
<211> LENGTH: 17
<212> TYPE: PRT
<213> ORGANISM: Mus musculus

<400> SEQUENCE: 73

Trp Ile Tyr Pro Gly Ser Gly Asn Thr Lys Tyr Asn Glu Lys Phe Lys
1               5                   10                  15

Asp

<210> SEQ ID NO 74
<211> LENGTH: 8
<212> TYPE: PRT
<213> ORGANISM: Mus musculus

<400> SEQUENCE: 74

Arg Arg Glu Asp Ser Phe Asp Tyr
1               5

<210> SEQ ID NO 75
<211> LENGTH: 351
<212> TYPE: DNA
<213> ORGANISM: Mus musculus

<400> SEQUENCE: 75
caaatccagc tacagcagtc tggacctgag ctggtgaaga ctggggcttc agtgaggata      60
tcctgcaagg cttctggctt caccttcact gactcctata aaactgggt gaagcagagg      120 cctggacagg gacttcagtg gattggatgg atttatcctg gaagcggtaa tactaagtac     180
aatgagaagt tcaaggacaa ggccacattg actgtagaca catcttccag cacagcctac     240
atgcagctca acagcctgac atctgaggac actgctgtct ttttctgtac aagaaggagg     300
gaggattctt ttgactattg gggccaaggc accactctca cagtctcctc a              351

<210> SEQ ID NO 76
<211> LENGTH: 113
<212> TYPE: PRT
<213> ORGANISM: Mus musculus

<400> SEQUENCE: 76

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Thr Trp Tyr Gln Gln Lys Pro Gly Gln
```

```
             35                  40                  45
Ser Pro Lys Leu Leu Ile Tyr Trp Ala Ser Ile Arg Glu Ser Gly Val
         50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys
```

<210> SEQ ID NO 77
<211> LENGTH: 17
<212> TYPE: PRT
<213> ORGANISM: Mus musculus

<400> SEQUENCE: 77

```
Lys Ser Ser Gln Ser Leu Leu Tyr Ser Ser Asn Gln Lys Asn Tyr Leu
1               5                   10                  15

Thr
```

<210> SEQ ID NO 78
<211> LENGTH: 7
<212> TYPE: PRT
<213> ORGANISM: Mus musculus

<400> SEQUENCE: 78

```
Trp Ala Ser Ile Arg Glu Ser
1               5
```

<210> SEQ ID NO 79
<211> LENGTH: 9
<212> TYPE: PRT
<213> ORGANISM: Mus musculus

<400> SEQUENCE: 79

```
Gln Gln Tyr Tyr Ser Tyr Pro Leu Thr
1               5
```

<210> SEQ ID NO 80
<211> LENGTH: 339
<212> TYPE: DNA
<213> ORGANISM: Mus musculus

<400> SEQUENCE: 80

```
gacattgtga tgtcacagtc tccatcctcc ctagctgtgt cagttggaga gaaggttact    60
atgagctgca agtccagtca gagccttta tatagtagca atcaaaagaa ctacttgacc   120
tggtaccagc agaaaccagg gcagtctcct aaactgctga tttactgggc atccattagg   180
gaatctgggg tccctgatcg cttcacaggc agtggatctg ggacagattt cactctcacc   240
atcagcagtg tgaaggctga agacctggca gtttattact gtcagcaata ttatagctat   300
ccgctcacgt tcggtgctgg gaccaagctg gagctgaaa                         339
```

<210> SEQ ID NO 81
<211> LENGTH: 117
<212> TYPE: PRT
<213> ORGANISM: Mus musculus

<400> SEQUENCE: 81

```
Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Thr Val Tyr
65                  70                  75                  80

Met Gln Pro Ser Ser Leu Thr Ser Glu Asp Ile Ala Val Tyr Phe Cys
                85                  90                  95

Ala Arg Arg Arg Glu Asp Ser Phe Asp Tyr Trp Gly Gln Gly Thr Thr
                100                 105                 110

Leu Thr Val Ser Ser
            115
```

<210> SEQ ID NO 82
<211> LENGTH: 5
<212> TYPE: PRT
<213> ORGANISM: Mus musculus

<400> SEQUENCE: 82

```
Asp Tyr Tyr Ile His
1               5
```

<210> SEQ ID NO 83
<211> LENGTH: 17
<212> TYPE: PRT
<213> ORGANISM: Mus musculus

<400> SEQUENCE: 83

```
Trp Ile Tyr Pro Gly Ser Gly Asn Thr Lys Tyr Asn Glu Lys Phe Lys
1               5                   10                  15

Gly
```

<210> SEQ ID NO 84
<211> LENGTH: 8
<212> TYPE: PRT
<213> ORGANISM: Mus musculus

<400> SEQUENCE: 84

```
Arg Arg Glu Asp Ser Phe Asp Tyr
1               5
```

<210> SEQ ID NO 85
<211> LENGTH: 351
<212> TYPE: DNA
<213> ORGANISM: Mus musculus

<400> SEQUENCE: 85

```
cagatccagc tgcagcagtc tggacctgag ctggtgaagc ctggggcttc agtgaagata      60
tcctgcaagg cttctggcta caccttcact gactactata tacactgggt gaagcagaag     120
cctggacagg gacttgagtg gattggatgg atttatcctg gaagcggtaa tactaagtac     180
aatgagaagt tcaagggcaa ggccacattg actgtagaca catcctccag cacagtctac     240
atgcagccca gcagcctgac atctgaggac attgctgtct atttctgtgc aagaaggagg     300
gaggattcct ttgactactg gggccaaggc accactctca cagtctcctc a              351
```

<210> SEQ ID NO 86
<211> LENGTH: 113
<212> TYPE: PRT
<213> ORGANISM: Mus musculus

<400> SEQUENCE: 86

Asp Ile Val Met Ser Gln Ser Pro Ser Ser Leu Thr Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Arg Lys Pro Gly Gln
        35                  40                  45

Ser Pro Lys Leu Leu Ile Tyr Trp Ala Ser Asn Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Phe Tyr Arg Tyr Pro Leu Thr Phe Gly Ala Gly Thr Lys Leu Glu Leu
            100                 105                 110

Lys

<210> SEQ ID NO 87
<211> LENGTH: 17
<212> TYPE: PRT
<213> ORGANISM: Mus musculus

<400> SEQUENCE: 87

Lys Ser Ser Gln Ser Leu Leu Tyr Ser Ser Asn Gln Lys Asn Tyr Leu
1               5                   10                  15

Ala

<210> SEQ ID NO 88
<211> LENGTH: 7
<212> TYPE: PRT
<213> ORGANISM: Mus musculus

<400> SEQUENCE: 88

Trp Ala Ser Asn Arg Glu Ser
1               5

<210> SEQ ID NO 89
<211> LENGTH: 9
<212> TYPE: PRT
<213> ORGANISM: Mus musculus

<400> SEQUENCE: 89

Gln Gln Phe Tyr Arg Tyr Pro Leu Thr
1               5

<210> SEQ ID NO 90
<211> LENGTH: 339
<212> TYPE: DNA
<213> ORGANISM: Mus musculus

<400> SEQUENCE: 90
gacattgtga tgtcacagtc tccatcctcc ctaactgtgt cagttggaga gaaggttact      60
atgagctgca agtccagtca gagccttttta tatagtagca atcaaaagaa ctatttggcc    120
tggtaccagc ggaagccagg gcagtctcct aaactgttga tttactgggc atccaatagg    180

```
gaatctgggg tccccgatcg cttcacaggc agtggatctg ggacagattt cactctcacc    240
atcagcagtg tgaaggctga agacctggca gtttattact gtcagcaatt ttataggtat    300
ccgctcacgt tcggtgctgg gaccaagctg gagctgaaa                           339
```

```
<210> SEQ ID NO 91
<211> LENGTH: 117
<212> TYPE: PRT
<213> ORGANISM: Mus musculus

<400> SEQUENCE: 91

Gln Ile Leu Leu Gln Gln Ser Gly Pro Asp Leu Val Lys Pro Gly Ala
1               5                   10                  15

Ser Val Lys Ile Ser Cys Lys Ala Ser Gly Tyr Thr Phe Thr Asp Asn
            20                  25                  30

Tyr Ile His Trp Val Lys Gln Lys Pro Gly Gln Gly Leu Glu Trp Ile
        35                  40                  45

Gly Trp Ile Tyr Pro Gly Ser Gly Asn Ala Lys Tyr Asn Glu Lys Phe
    50                  55                  60

Lys Gly Lys Ala Thr Leu Thr Val Asp Arg Ser Ser Ser Thr Pro Tyr
65                  70                  75                  80

Met Gln Leu Ser Ser Leu Thr Ser Glu Asp Thr Ala Val Tyr Phe Cys
                85                  90                  95

Thr Arg Arg Arg Glu Asp Ser Phe Asp Tyr Trp Gly Gln Gly Thr Thr
            100                 105                 110

Leu Thr Val Ser Ser
        115

<210> SEQ ID NO 92
<211> LENGTH: 5
<212> TYPE: PRT
<213> ORGANISM: Mus musculus

<400> SEQUENCE: 92

Asp Asn Tyr Ile His
1               5

<210> SEQ ID NO 93
<211> LENGTH: 17
<212> TYPE: PRT
<213> ORGANISM: Mus musculus

<400> SEQUENCE: 93

Trp Ile Tyr Pro Gly Ser Gly Asn Ala Lys Tyr Asn Glu Lys Phe Lys
1               5                   10                  15

Gly

<210> SEQ ID NO 94
<211> LENGTH: 8
<212> TYPE: PRT
<213> ORGANISM: Mus musculus

<400> SEQUENCE: 94

Arg Arg Glu Asp Ser Phe Asp Tyr
1               5

<210> SEQ ID NO 95
<211> LENGTH: 351
<212> TYPE: DNA
<213> ORGANISM: Mus musculus
```

<400> SEQUENCE: 95

```
cagatcctgc tgcagcagtc tggacctgac ctggtgaagc ctggggcttc agtgaagatt    60
tcctgcaagg cttcgggata caccttcact gacaactata tacactgggt gaagcagaag   120
cctggacagg gacttgagtg gattggatgg atttatcctg aagtggtaa tgctaagtac    180
aatgagaaat tcaagggcaa ggccacattg actgtagaca atcctccag cacacctac    240
atgcaactca gcagcctgac atctgaggac actgctgtct atttctgtac aagaaggagg   300
gaggattcct ttgactactg gggccaaggc accactctca cagtctcctc a           351
```

<210> SEQ ID NO 96
<211> LENGTH: 113
<212> TYPE: PRT
<213> ORGANISM: Mus musculus

<400> SEQUENCE: 96

```
Asp Ile Val Met Ser Gln Ser Pro Ser Ser Leu Ala Val Ser Val Gly
1               5                   10                  15
Glu Lys Val Thr Met Ser Cys Lys Ser Ser Gln Ser Leu Leu Tyr Ser
                20                  25                  30
Ser Asn Gln Lys Asn Tyr Leu Ala Trp Tyr Gln Gln Lys Pro Gly Gln
            35                  40                  45
Ser Pro Lys Leu Leu Ile Tyr Trp Ala Ser Thr Arg Glu Ser Gly Val
        50                  55                  60
Pro Asp Arg Phe Thr Gly Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
Phe Tyr Arg Tyr Pro Leu Thr Phe Gly Ala Gly Thr Lys Leu Glu Leu
            100                 105                 110
Lys
```

<210> SEQ ID NO 97
<211> LENGTH: 17
<212> TYPE: PRT
<213> ORGANISM: Mus musculus

<400> SEQUENCE: 97

```
Lys Ser Ser Gln Ser Leu Leu Tyr Ser Ser Asn Gln Lys Asn Tyr Leu
1               5                   10                  15
Ala
```

<210> SEQ ID NO 98
<211> LENGTH: 7
<212> TYPE: PRT
<213> ORGANISM: Mus musculus

<400> SEQUENCE: 98

```
Trp Ala Ser Thr Arg Glu Ser
1               5
```

<210> SEQ ID NO 99
<211> LENGTH: 9
<212> TYPE: PRT
<213> ORGANISM: Mus musculus

<400> SEQUENCE: 99

Gln Gln Phe Tyr Arg Tyr Pro Leu Thr

<210> SEQ ID NO 100
<211> LENGTH: 339
<212> TYPE: DNA
<213> ORGANISM: Mus musculus

<400> SEQUENCE: 100

```
gacattgtga tgtcacagtc tccatcctcc ctagctgtgt cagttggaga gaaggttact      60
atgagctgca agtccagtca gagccttttta tatagtagca atcaaaagaa ctacttggcc    120
tggtaccagc agaaaccagg gcagtctcct aaactgctga tttactgggc atccactagg    180
gaatctgggg tccctgatcg cttcacaggc agtggatctg gacagagttt cactctcacc    240
atcagcagtg tgaaggctga agacctggca gtttattact gtcagcaatt ttataggtat    300
ccgctcacgt tcggcgctgg gaccaagctg gagctgaaa                            339
```

<210> SEQ ID NO 101
<211> LENGTH: 117
<212> TYPE: PRT
<213> ORGANISM: Homo sapiens

<400> SEQUENCE: 101

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Leu Thr Val Asp Thr Ser Ser Thr Val Tyr
65                  70                  75                  80

Met Glu Leu Ser Ser Leu Arg Ser Asp Asp Thr Ala Val Tyr Phe Cys
                85                  90                  95

Ala Arg Arg Arg Glu Asp Ser Phe Asp Tyr Trp Gly Gln Gly Thr Leu
            100                 105                 110

Val Thr Val Ser Ser
        115
```

<210> SEQ ID NO 102
<211> LENGTH: 5
<212> TYPE: PRT
<213> ORGANISM: Homo sapiens

<400> SEQUENCE: 102

```
Asp Tyr Tyr Ile His
1               5
```

<210> SEQ ID NO 103
<211> LENGTH: 17
<212> TYPE: PRT
<213> ORGANISM: Homo sapiens

<400> SEQUENCE: 103

```
Trp Ile Tyr Pro Gly Ser Gly Asn Thr Lys Tyr Asn Glu Lys Phe Gln
1               5                   10                  15

Gly
```

<210> SEQ ID NO 104
<211> LENGTH: 8
<212> TYPE: PRT
<213> ORGANISM: Homo sapiens

<400> SEQUENCE: 104

Arg Arg Glu Asp Ser Phe Asp Tyr
1               5

<210> SEQ ID NO 105
<211> LENGTH: 351
<212> TYPE: DNA
<213> ORGANISM: Homo sapiens

<400> SEQUENCE: 105

```
cagattcagc tggtgcagtc tggcgccgaa gtgaagaaac ctggcgcctc tgtgaaggtg      60
tcctgcaagg ctagcggcta cattcacc gactactaca tccactgggt ccgacaggcc     120
cctggacagg gacttgaatg gatgggctgg atctaccctg gcagcggcaa caccaagtac    180
aacgagaagt tccagggcag agtgaccctg accgtggaca caagcagcag caccgtgtac    240
atggaactga gcagcctgag aagcgacgat accgccgtgt acttctgtgc agaagaaga    300
gaggacagct cgactactg gggccaggga acactggtca ccgttagctc t              351
```

<210> SEQ ID NO 106
<211> LENGTH: 117
<212> TYPE: PRT
<213> ORGANISM: Homo sapiens

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Leu Thr Val Asp Thr Ser Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Glu Asp Ser Phe Asp Tyr Trp Gly Gln Gly Thr Leu
            100                 105                 110

Val Thr Val Ser Ser
        115

<210> SEQ ID NO 107
<211> LENGTH: 5
<212> TYPE: PRT
<213> ORGANISM: Homo sapiens

<400> SEQUENCE: 107

Asp Tyr Tyr Ile His
1               5

<210> SEQ ID NO 108
<211> LENGTH: 17
<212> TYPE: PRT
<213> ORGANISM: Homo sapiens

<400> SEQUENCE: 108

Trp Ile Tyr Pro Gly Ser Gly Asn Thr Lys Tyr Asn Glu Lys Phe Gln
1               5                   10                  15

Gly

<210> SEQ ID NO 109
<211> LENGTH: 8
<212> TYPE: PRT
<213> ORGANISM: Homo sapiens

<400> SEQUENCE: 109

Arg Arg Glu Asp Ser Phe Asp Tyr
1               5

<210> SEQ ID NO 110
<211> LENGTH: 351
<212> TYPE: DNA
<213> ORGANISM: Homo sapiens

<400> SEQUENCE: 110
caggttcagc tggttcagtc tggcgccgaa gtgaagaaac ctggcgcctc tgtgaaggtg     60
tcctgcaagg ctagcggcta cacattcacc gactactaca tccactgggt ccgacaggcc    120
cctggacagg gacttgaatg gatgggctgg atctaccctg gcagcggcaa caccaagtac    180
aacgagaagt tccagggcag agtgaccctg accgtggaca ccagcacaag caccgtgtac    240
atggaactga gcagcctgag aagcgacgac accgccgtgt actactgcgc cagaagaaga    300
gaggacagct tcgactactg gggccaggga acactggtca ccgttagctc t             351

<210> SEQ ID NO 111
<211> LENGTH: 117
<212> TYPE: PRT
<213> ORGANISM: Homo sapiens

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Arg Arg Glu Asp Ser Phe Asp Tyr Trp Gly Gln Gly Thr Leu
            100                 105                 110

Val Thr Val Ser Ser
        115

<210> SEQ ID NO 112
<211> LENGTH: 5
<212> TYPE: PRT
<213> ORGANISM: Homo sapiens

<400> SEQUENCE: 112

Asp Tyr Tyr Ile His

```
<210> SEQ ID NO 113
<211> LENGTH: 17
<212> TYPE: PRT
<213> ORGANISM: Homo sapiens

<400> SEQUENCE: 113

Trp Ile Tyr Pro Gly Ser Gly Asn Thr Lys Tyr Asn Glu Lys Phe Gln
1               5                   10                  15
Gly

<210> SEQ ID NO 114
<211> LENGTH: 8
<212> TYPE: PRT
<213> ORGANISM: Homo sapiens

<400> SEQUENCE: 114

Arg Arg Glu Asp Ser Phe Asp Tyr
1               5

<210> SEQ ID NO 115
<211> LENGTH: 351
<212> TYPE: DNA
<213> ORGANISM: Homo sapiens

<400> SEQUENCE: 115
caggttcagc tggttcagtc tggcgccgaa gtgaagaaac ctggcgcctc tgtgaaggtg      60
tcctgcaagg ctagcggcta cacattcacc gactactaca tccactgggt ccgacaggcc     120
cctggacagg gacttgaatg gatgggctgg atctaccctg gcagcggcaa caccaagtac     180
aacgagaagt tccagggcag agtgaccatg accgtggaca ccagcatcag caccgcctac     240
atggaactga gcagcctgag aagcgacgac accgccgtgt actactgcgc cagaagaaga     300
gaggacagct tcgactactg gggccaggga acactggtca ccgttagctc t              351

<210> SEQ ID NO 116
<211> LENGTH: 117
<212> TYPE: PRT
<213> ORGANISM: Homo sapiens

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Met Thr Arg Asp Thr Ser Ile Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Glu Asp Ser Phe Asp Tyr Trp Gly Gln Gly Thr Leu
                100                 105                 110

Val Thr Val Ser Ser
            115
```

<210> SEQ ID NO 117
<211> LENGTH: 5
<212> TYPE: PRT
<213> ORGANISM: Homo sapiens

<400> SEQUENCE: 117

Asp Tyr Tyr Ile His
1               5

<210> SEQ ID NO 118
<211> LENGTH: 17
<212> TYPE: PRT
<213> ORGANISM: Homo sapiens

<400> SEQUENCE: 118

Trp Ile Tyr Pro Gly Ser Gly Asn Thr Lys Tyr Asn Glu Lys Phe Gln
1               5                   10                  15

Gly

<210> SEQ ID NO 119
<211> LENGTH: 8
<212> TYPE: PRT
<213> ORGANISM: Homo sapiens

<400> SEQUENCE: 119

Arg Arg Glu Asp Ser Phe Asp Tyr
1               5

<210> SEQ ID NO 120
<211> LENGTH: 351
<212> TYPE: DNA
<213> ORGANISM: Homo sapiens

<400> SEQUENCE: 120
caggttcagc tggttcagtc tggcgccgaa gtgaagaaac ctggcgcctc tgtgaaggtg    60
tcctgcaagg ctagcggcta cacattcacc gactactaca tccactgggt ccgacaggcc   120
cctggacagg gacttgaatg gatgggctgg atctaccctg gcagcggcaa caccaagtac   180
aacgagaagt tccagggcag agtgaccatg accagagaca ccagcatcag caccgtgtac   240
atggaactga gcagcctgag aagcgacgac accgccgtgt actactgcgc cagaagaaga   300
gaggacagct cgactactg gggccaggga acactggtca ccgttagctc t              351

<210> SEQ ID NO 121
<211> LENGTH: 117
<212> TYPE: PRT
<213> ORGANISM: Homo sapiens

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Arg Arg Glu Asp Ser Phe Asp Tyr Trp Gly Gln Gly Thr Leu
            100                 105                 110

Val Thr Val Ser Ser
        115

<210> SEQ ID NO 122
<211> LENGTH: 5
<212> TYPE: PRT
<213> ORGANISM: Homo sapiens

<400> SEQUENCE: 122

Asp Tyr Tyr Ile His
1               5

<210> SEQ ID NO 123
<211> LENGTH: 17
<212> TYPE: PRT
<213> ORGANISM: Homo sapiens

<400> SEQUENCE: 123

Trp Ile Tyr Pro Gly Ser Gly Asn Thr Lys Tyr Asn Glu Lys Phe Gln
1               5                   10                  15

Gly

<210> SEQ ID NO 124
<211> LENGTH: 8
<212> TYPE: PRT
<213> ORGANISM: Homo sapiens

<400> SEQUENCE: 124

Arg Arg Glu Asp Ser Phe Asp Tyr
1               5

<210> SEQ ID NO 125
<211> LENGTH: 351
<212> TYPE: DNA
<213> ORGANISM: Homo sapiens

<400> SEQUENCE: 125
caggttcagc tggttcagtc tggcgccgaa gtgaagaaac ctggcgcctc tgtgaaggtg      60
tcctgcaagg ctagcggcta cacattcacc gactactaca tccactgggt ccgacaggcc     120
cctggacagg gacttgaatg gatgggctgg atctaccctg gcagcggcaa caccaagtac     180
aacgagaagt tccagggcag agtgaccatg accagagaca ccagcatcag caccgcctac     240
atggaactga gcagcctgag aagcgacgac accgccgtgt actactgcgc cagaagaaga     300
gaggacagct cgactactg gggccaggga acactggtca ccgttagctc t              351

<210> SEQ ID NO 126
<211> LENGTH: 117
<212> TYPE: PRT
<213> ORGANISM: Homo sapiens

<400> SEQUENCE: 126

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

```
Gly Trp Ile Tyr Pro Gly Ser Gly Asn Thr Lys Tyr Asn Glu Lys Phe
 50                  55                  60

Gln Gly Arg Val Thr Leu Thr Val Asp Thr Ser Thr Ser Thr Val Tyr
 65                  70                  75                  80

Met Glu Leu Ser Ser Leu Arg Ser Asp Asp Thr Ala Val Tyr Tyr Cys
                 85                  90                  95

Ala Arg Arg Arg Glu Asp Ser Phe Asp Tyr Trp Gly Gln Gly Thr Leu
                100                 105                 110

Val Thr Val Ser Ser
                115

<210> SEQ ID NO 127
<211> LENGTH: 5
<212> TYPE: PRT
<213> ORGANISM: Homo sapiens

<400> SEQUENCE: 127

Asp Tyr Tyr Ile His
1               5

<210> SEQ ID NO 128
<211> LENGTH: 17
<212> TYPE: PRT
<213> ORGANISM: Homo sapiens

<400> SEQUENCE: 128

Trp Ile Tyr Pro Gly Ser Gly Asn Thr Lys Tyr Asn Glu Lys Phe Gln
1               5                   10                  15

Gly

<210> SEQ ID NO 129
<211> LENGTH: 8
<212> TYPE: PRT
<213> ORGANISM: Homo sapiens

<400> SEQUENCE: 129

Arg Arg Glu Asp Ser Phe Asp Tyr
1               5

<210> SEQ ID NO 130
<211> LENGTH: 351
<212> TYPE: DNA
<213> ORGANISM: Homo sapiens

<400> SEQUENCE: 130
caggttcagc tggttcagtc tggccctgaa gtgaagaaac ctggcgcctc tgtgaaggtg      60
tcctgcaagg ctagcggcta cacattcacc gactactaca tccactgggt ccgacaggcc     120
cctggacagg gacttgaatg gatgggctgg atctaccctg gcagcggcaa caccaagtac     180
aacgagaagt tccagggcag agtgaccctg accgtggaca ccagcacaag caccgtgtac     240
atggaactga gcagcctgag aagcgacgac accgccgtgt actactgcgc cagaagaaga     300
gaggacagct tcgactactg gggccaggga acactggtca ccgttagctc t              351

<210> SEQ ID NO 131
<211> LENGTH: 117
<212> TYPE: PRT
<213> ORGANISM: Homo sapiens

<400> SEQUENCE: 131

Gln Val Gln Leu Val Gln Ser Gly Ala Glu Leu Lys Lys Pro Gly Ala
```

```
1               5                   10                  15
Ser Val Lys Val Ser Cys Lys Ala Ser Gly Tyr Thr Phe Thr Asp Tyr
                    20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
    50                  55                  60

Gln Gly Arg Val Thr Leu Thr Val Asp Thr Ser Thr Ser Thr Val Tyr
65                  70                  75                  80

Met Glu Leu Ser Ser Leu Arg Ser Asp Thr Ala Val Tyr Tyr Cys
                85                  90                  95

Ala Arg Arg Arg Glu Asp Ser Phe Asp Tyr Trp Gly Gln Gly Thr Leu
                    100                 105                 110

Val Thr Val Ser Ser
            115
```

<210> SEQ ID NO 132
<211> LENGTH: 5
<212> TYPE: PRT
<213> ORGANISM: Homo sapiens

<400> SEQUENCE: 132

```
Asp Tyr Tyr Ile His
1               5
```

<210> SEQ ID NO 133
<211> LENGTH: 17
<212> TYPE: PRT
<213> ORGANISM: Homo sapiens

<400> SEQUENCE: 133

```
Trp Ile Tyr Pro Gly Ser Gly Asn Thr Lys Tyr Asn Glu Lys Phe Gln
1               5                   10                  15

Gly
```

<210> SEQ ID NO 134
<211> LENGTH: 8
<212> TYPE: PRT
<213> ORGANISM: Homo sapiens

<400> SEQUENCE: 134

```
Arg Arg Glu Asp Ser Phe Asp Tyr
1               5
```

<210> SEQ ID NO 135
<211> LENGTH: 351
<212> TYPE: DNA
<213> ORGANISM: Homo sapiens

<400> SEQUENCE: 135

```
caggttcagc tggttcagtc tggcgccgaa ctgaagaaac ctggcgcctc tgtgaaggtg      60
tcctgcaagg ctagcggcta cacattcacc gactactaca tccactgggt ccgacaggcc     120
cctggacagg gacttgaatg gatgggctgg atctaccctg gcagcggcaa caccaagtac     180
aacgagaagt tccagggcag agtgaccctg accgtggaca ccagcacaag caccgtgtac     240
atggaactga gcagcctgag aagcgacgac accgccgtgt actactgcgc cagaagaaga     300
gaggacagct cgactactg gggccaggga acactggtca ccgttagctc t               351
```

<210> SEQ ID NO 136
<211> LENGTH: 117
<212> TYPE: PRT
<213> ORGANISM: Homo sapiens

<400> SEQUENCE: 136

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Ile His Trp Val Arg Gln Ala Pro Gly Gln Gly Leu Glu Trp Met
        35                  40                  45
Gly Trp Ile Tyr Pro Gly Ser Gly Asn Thr Lys Tyr Asn Glu Lys Phe
    50                  55                  60
Gln Gly Arg Val Thr Leu Thr Val Asp Thr Ser Thr Ser Thr Val Tyr
65                  70                  75                  80
Met Glu Leu Ser Ser Leu Arg Ser Asp Asp Ile Ala Val Tyr Tyr Cys
                85                  90                  95
Ala Arg Arg Arg Glu Asp Ser Phe Asp Tyr Trp Gly Gln Gly Thr Leu
            100                 105                 110
Val Thr Val Ser Ser
        115

<210> SEQ ID NO 137
<211> LENGTH: 5
<212> TYPE: PRT
<213> ORGANISM: Homo sapiens

<400> SEQUENCE: 137

Asp Tyr Tyr Ile His
1               5

<210> SEQ ID NO 138
<211> LENGTH: 17
<212> TYPE: PRT
<213> ORGANISM: Homo sapiens

<400> SEQUENCE: 138

Trp Ile Tyr Pro Gly Ser Gly Asn Thr Lys Tyr Asn Glu Lys Phe Gln
1               5                   10                  15
Gly

<210> SEQ ID NO 139
<211> LENGTH: 8
<212> TYPE: PRT
<213> ORGANISM: Homo sapiens

<400> SEQUENCE: 139

Arg Arg Glu Asp Ser Phe Asp Tyr
1               5

<210> SEQ ID NO 140
<211> LENGTH: 351
<212> TYPE: DNA
<213> ORGANISM: Homo sapiens

<400> SEQUENCE: 140
caggttcagc tggttcagtc tggcgccgaa gtgaagaaac ctggcgcctc tgtgaaggtg     60
tcctgcaagg ctagcggcta cacattcacc gactactaca tccactgggt ccgacaggcc    120
cctggacagg gacttgaatg gatgggctgg atctaccctg gcagcggcaa caccaagtac    180

```
aacgagaagt tccagggcag agtgaccctg accgtggaca ccagcacaag caccgtgtac    240
atggaactga gcagcctgag aagcgacgac attgccgtgt actactgcgc cagaagaaga    300
gaggacagct tcgactactg gggccaggga acactggtca ccgttagctc t             351
```

```
<210> SEQ ID NO 141
<211> LENGTH: 117
<212> TYPE: PRT
<213> ORGANISM: Homo sapiens

<400> SEQUENCE: 141
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Leu Thr Val Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Arg Arg Glu Asp Ser Phe Asp Tyr Trp Gly Gln Gly Thr Thr
            100                 105                 110

Val Thr Val Ser Ser
        115

```
<210> SEQ ID NO 142
<211> LENGTH: 5
<212> TYPE: PRT
<213> ORGANISM: Homo sapiens

<400> SEQUENCE: 142
```

Asp Tyr Tyr Ile His
1               5

```
<210> SEQ ID NO 143
<211> LENGTH: 17
<212> TYPE: PRT
<213> ORGANISM: Homo sapiens

<400> SEQUENCE: 143
```

Trp Ile Tyr Pro Gly Ser Gly Asn Thr Lys Tyr Asn Glu Lys Phe Gln
1               5                   10                  15

Gly

```
<210> SEQ ID NO 144
<211> LENGTH: 8
<212> TYPE: PRT
<213> ORGANISM: Homo sapiens

<400> SEQUENCE: 144
```

Arg Arg Glu Asp Ser Phe Asp Tyr
1               5

```
<210> SEQ ID NO 145
<211> LENGTH: 351
<212> TYPE: DNA
<213> ORGANISM: Homo sapiens
```

<400> SEQUENCE: 145

```
caggttcagc tggttcagtc tggcgccgaa gtgaagaaac ctggcgcctc tgtgaaggtg      60
tcctgcaagg ctagcggcta cacattcacc gactactaca tccactgggt ccgacaggcc     120
cctggacagg gacttgaatg gatgggctgg atctaccctg gcagcggcaa caccaagtac     180
aacgagaagt tccagggcag agtgaccctg accgtggaca ccagcacaag caccgtgtac     240
atggaactga gcagcctgag aagcgacgac accgccgtgt actactgcgc cagaagaaga     300
gaggacagct tcgactactg gggccaggga acaactgtca ccgttagctc t             351
```

<210> SEQ ID NO 146
<211> LENGTH: 117
<212> TYPE: PRT
<213> ORGANISM: Homo sapiens

<400> SEQUENCE: 146

```
Gln Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asp Tyr
            20                  25                  30
Tyr Ile His Trp Val Arg Gln Ala Pro Gly Gln Gly Leu Glu Trp Met
        35                  40                  45
Gly Trp Ile Tyr Pro Gly Ser Gly Asn Thr Lys Tyr Asn Glu Lys Phe
    50                  55                  60
Gln Gly Arg Val Thr Leu Thr Val Asp Thr Ser Thr Ser Thr Val Tyr
65                  70                  75                  80
Met Glu Leu Ser Ser Leu Arg Ser Asp Asp Thr Ala Val Tyr Tyr Cys
                85                  90                  95
Ala Arg Arg Arg Glu Asp Ser Phe Asp Tyr Trp Gly Gln Gly Thr Leu
            100                 105                 110
Val Thr Val Ser Ser
        115
```

<210> SEQ ID NO 147
<211> LENGTH: 5
<212> TYPE: PRT
<213> ORGANISM: Homo sapiens

<400> SEQUENCE: 147

```
Asp Tyr Tyr Ile His
1               5
```

<210> SEQ ID NO 148
<211> LENGTH: 17
<212> TYPE: PRT
<213> ORGANISM: Homo sapiens

<400> SEQUENCE: 148

```
Trp Ile Tyr Pro Gly Ser Gly Asn Thr Lys Tyr Asn Glu Lys Phe Gln
1               5                   10                  15
Gly
```

<210> SEQ ID NO 149
<211> LENGTH: 8
<212> TYPE: PRT
<213> ORGANISM: Homo sapiens

<400> SEQUENCE: 149

Arg Arg Glu Asp Ser Phe Asp Tyr
1               5

<210> SEQ ID NO 150
<211> LENGTH: 351
<212> TYPE: DNA
<213> ORGANISM: Homo sapiens

<400> SEQUENCE: 150
caggttcagc tggtgcagtc tggacccgag ctgaagaaac ctggcgcctc tgtgaaggtg     60
tcctgcaagg ctagcggcta cacattcacc gactactaca tccactgggt ccgacaggcc    120
cctggacagg gacttgaatg gatgggctgg atctaccctg gcagcggcaa caccaagtac    180
aacgagaagt tccagggcag agtgaccctg accgtggaca ccagcacaag caccgtgtac    240
atggaactga gcagcctgag aagcgacgac accgccgtgt actactgcgc cagaagaaga    300
gaggacagct cgactactg gggccaggga acactggtca ccgttagctc t              351

<210> SEQ ID NO 151
<211> LENGTH: 117
<212> TYPE: PRT
<213> ORGANISM: Homo sapiens

<400> SEQUENCE: 151

Gln Ile Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Leu Thr Val Asp Thr Ser Ser Ser Thr Val Tyr
65                  70                  75                  80

Met Glu Leu Ser Ser Leu Arg Ser Asp Asp Thr Ala Val Tyr Phe Cys
                85                  90                  95

Ala Arg Arg Arg Glu Asp Ser Phe Asp Tyr Trp Gly Gln Gly Thr Leu
                100                 105                 110

Val Thr Val Ser Ser
        115

<210> SEQ ID NO 152
<211> LENGTH: 5
<212> TYPE: PRT
<213> ORGANISM: Homo sapiens

<400> SEQUENCE: 152

Asp Tyr Tyr Ile His
1               5

<210> SEQ ID NO 153
<211> LENGTH: 17
<212> TYPE: PRT
<213> ORGANISM: Homo sapiens

<400> SEQUENCE: 153

Trp Ile Tyr Pro Gly Ser Gly Asn Thr Lys Tyr Asn Glu Lys Phe Gln
1               5                   10                  15

Gly

<210> SEQ ID NO 154
<211> LENGTH: 8
<212> TYPE: PRT
<213> ORGANISM: Homo sapiens

<400> SEQUENCE: 154

Arg Arg Glu Asp Ser Phe Asp Tyr
1               5

<210> SEQ ID NO 155
<211> LENGTH: 351
<212> TYPE: DNA
<213> ORGANISM: Homo sapiens

<400> SEQUENCE: 155

```
cagattcagc tggtgcagtc tggcgccgaa ctgaagaaac ctggcgcctc tgtgaaggtg      60
tcctgcaagg ctagcggcta cacattcacc gactactaca tccactgggt ccgacaggcc     120
cctggacagg gacttgaatg gatgggctgg atctaccctg cagcggcaa caccaagtac      180 aacgagaagt tccagggcag agtgaccctg accgtggaca agcagcag caccgtgtac       240 atggaactga gcagcctgag aagcgacgat accgccgtgt acttctgtgc cagaagaaga    300
gaggacagct cgactactg gggccaggga acactggtca ccgttagctc t               351
```

<210> SEQ ID NO 156
<211> LENGTH: 113
<212> TYPE: PRT
<213> ORGANISM: Homo sapiens

<400> SEQUENCE: 156

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Arg Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Arg Tyr Pro Leu Thr Phe Gly Gln Gly Thr Lys Val Glu Ile
            100                 105                 110

Lys

<210> SEQ ID NO 157
<211> LENGTH: 17
<212> TYPE: PRT
<213> ORGANISM: Homo sapiens

<400> SEQUENCE: 157

Lys Ser Ser Gln Ser Leu Leu Tyr Ser Ser Asn Gln Lys Asn Tyr Leu
1               5                   10                  15

Ala

<210> SEQ ID NO 158
<211> LENGTH: 7
<212> TYPE: PRT

```
<213> ORGANISM: Homo sapiens

<400> SEQUENCE: 158

Trp Ala Ser Asn Arg Glu Ser
1               5

<210> SEQ ID NO 159
<211> LENGTH: 9
<212> TYPE: PRT
<213> ORGANISM: Homo sapiens

<400> SEQUENCE: 159

Gln Gln Phe Tyr Arg Tyr Pro Leu Thr
1               5

<210> SEQ ID NO 160
<211> LENGTH: 339
<212> TYPE: DNA
<213> ORGANISM: Homo sapiens

<400> SEQUENCE: 160
gacatcgtga tgacacagag ccctgatagc ctggccgtgt ctctgggaga gagagccacc    60
atcaactgca agagcagcca gagcctgctg tactccagca accagaagaa ctacctggcc   120
tggtatcaga aaagcccgg ccagcctcct aagctgctga tctactgggc cagcaacaga   180
gaatccggcg tgcccgatag attcagcggc tctggatctg caccgactt cacccctgaca   240 atcagctccc tgcaggccga ggatgtggcc gtgtactact gccagcagtt ctacagatac   300
cctctgacct tcggccaggg caccaaggtg gaaatcaag                          339

<210> SEQ ID NO 161
<211> LENGTH: 113
<212> TYPE: PRT
<213> ORGANISM: Homo sapiens

<400> SEQUENCE: 161

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Asn Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Arg Tyr Pro Leu Thr Phe Gly Gln Gly Thr Lys Val Glu Ile
            100                 105                 110

Lys

<210> SEQ ID NO 162
<211> LENGTH: 17
<212> TYPE: PRT
<213> ORGANISM: Homo sapiens

<400> SEQUENCE: 162

Lys Ser Ser Gln Ser Leu Leu Tyr Ser Ser Asn Gln Lys Asn Tyr Leu
1               5                   10                  15
```

<210> SEQ ID NO 163
<211> LENGTH: 7
<212> TYPE: PRT
<213> ORGANISM: Homo sapiens

<400> SEQUENCE: 163

Trp Ala Ser Asn Arg Glu Ser
1               5

<210> SEQ ID NO 164
<211> LENGTH: 9
<212> TYPE: PRT
<213> ORGANISM: Homo sapiens

<400> SEQUENCE: 164

Gln Gln Phe Tyr Arg Tyr Pro Leu Thr
1               5

<210> SEQ ID NO 165
<211> LENGTH: 339
<212> TYPE: DNA
<213> ORGANISM: Homo sapiens

<400> SEQUENCE: 165
gacatcgtga tgacacagag ccctgatagc ctggccgtgt ctctgggaga gagagccacc      60
atcaactgca agagcagcca gagcctgctg tactccagca accagaagaa ctacctggcc     120
tggtatcagc agaagcccgg ccagcctcct aagctgctga tctactgggc cagcaacaga     180
gaaagcggcg tgcccgatag attcagcggc tctggatctg caccgactt caccctgaca      240 atcagctccc tgcaggccga ggatgtggcc gtgtactact gccagcagtt ctacagatac     300
cctctgacct tcggccaggg caccaaggtg gaaatcaag                             339

<210> SEQ ID NO 166
<211> LENGTH: 113
<212> TYPE: PRT
<213> ORGANISM: Homo sapiens

<400> SEQUENCE: 166

Asp Ile Val Met Thr Gln Ser Pro Asp Ser Leu Thr Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Arg Tyr Pro Leu Thr Phe Gly Gln Gly Thr Lys Val Glu Ile
            100                 105                 110

Lys

<210> SEQ ID NO 167
<211> LENGTH: 17

```
<212> TYPE: PRT
<213> ORGANISM: Homo sapiens

<400> SEQUENCE: 167

Lys Ser Ser Gln Ser Leu Leu Tyr Ser Ser Asn Gln Lys Asn Tyr Leu
1               5                   10                  15

Ala

<210> SEQ ID NO 168
<211> LENGTH: 7
<212> TYPE: PRT
<213> ORGANISM: Homo sapiens

<400> SEQUENCE: 168

Trp Ala Ser Asn Arg Glu Ser
1               5

<210> SEQ ID NO 169
<211> LENGTH: 9
<212> TYPE: PRT
<213> ORGANISM: Homo sapiens

<400> SEQUENCE: 169

Gln Gln Phe Tyr Arg Tyr Pro Leu Thr
1               5

<210> SEQ ID NO 170
<211> LENGTH: 339
<212> TYPE: DNA
<213> ORGANISM: Homo sapiens

<400> SEQUENCE: 170
gacatcgtga tgacacagag ccctgatagc ctgactgtgt ctctgggaga gagagccacc      60
atcaactgca agagcagcca gagcctgctg tactccagca accagaagaa ctacctggcc     120
tggtatcagc agaagcccgg ccagcctcct aagctgctga tctactgggc cagcaacaga     180
gaaagcggcg tgcccgatag attcagcggc tctggatctg caccgactt caccctgaca      240 atcagctccc tgcaggccga ggatgtggcc gtgtactact gccagcagtt ctacagatac     300
cctctgacct tcggccaggg caccaaggtg gaaatcaag                            339

<210> SEQ ID NO 171
<211> LENGTH: 113
<212> TYPE: PRT
<213> ORGANISM: Homo sapiens

<400> SEQUENCE: 171

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Arg Tyr Pro Leu Thr Phe Gly Gln Gly Thr Lys Leu Glu Ile
```

Lys

<210> SEQ ID NO 172
<211> LENGTH: 17
<212> TYPE: PRT
<213> ORGANISM: Homo sapiens

<400> SEQUENCE: 172

Lys Ser Ser Gln Ser Leu Leu Tyr Ser Ser Asn Gln Lys Asn Tyr Leu
1               5                   10                  15

Ala

<210> SEQ ID NO 173
<211> LENGTH: 7
<212> TYPE: PRT
<213> ORGANISM: Homo sapiens

<400> SEQUENCE: 173

Trp Ala Ser Asn Arg Glu Ser
1               5

<210> SEQ ID NO 174
<211> LENGTH: 9
<212> TYPE: PRT
<213> ORGANISM: Homo sapiens

<400> SEQUENCE: 174

Gln Gln Phe Tyr Arg Tyr Pro Leu Thr
1               5

<210> SEQ ID NO 175
<211> LENGTH: 339
<212> TYPE: DNA
<213> ORGANISM: Homo sapiens

<400> SEQUENCE: 175
gacatcgtga tgacacagag ccctgatagc ctggccgtgt ctctgggaga gagagccacc      60
atcaactgca agagcagcca gagcctgctg tactccagca accagaagaa ctacctggcc     120
tggtatcagc agaagcccgg ccagcctcct aagctgctga tctactgggc cagcaacaga     180
gaaagcggcg tgcccgatag attcagcggc tctggatctg caccgactt caccctgaca      240
atcagctccc tgcaggccga ggatgtggcc gtgtactact gccagcagtt ctacagatac     300
cctctgacct cggccaggg caccaagctg gaaatcaag                              339

<210> SEQ ID NO 176
<211> LENGTH: 113
<212> TYPE: PRT
<213> ORGANISM: Homo sapiens

<400> SEQUENCE: 176

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe Tyr Arg Tyr Pro Leu Thr Phe Gly Gln Gly Thr Lys Val Glu Leu
            100                 105                 110

Lys

<210> SEQ ID NO 177
<211> LENGTH: 17
<212> TYPE: PRT
<213> ORGANISM: Homo sapiens

<400> SEQUENCE: 177

Lys Ser Ser Gln Ser Leu Leu Tyr Ser Ser Asn Gln Lys Asn Tyr Leu
  1               5                  10                  15

Ala

<210> SEQ ID NO 178
<211> LENGTH: 7
<212> TYPE: PRT
<213> ORGANISM: Homo sapiens

<400> SEQUENCE: 178

Trp Ala Ser Asn Arg Glu Ser
  1               5

<210> SEQ ID NO 179
<211> LENGTH: 9
<212> TYPE: PRT
<213> ORGANISM: Homo sapiens

<400> SEQUENCE: 179

Gln Gln Phe Tyr Arg Tyr Pro Leu Thr
  1               5

<210> SEQ ID NO 180
<211> LENGTH: 339
<212> TYPE: DNA
<213> ORGANISM: Homo sapiens

<400> SEQUENCE: 180
gacatcgtga tgacacagag ccctgatagc ctggccgtgt ctctgggaga gagagccacc      60
atcaactgca agagcagcca gagcctgctg tactccagca accagaagaa ctacctggcc     120
tggtatcagc agaagcccgg ccagcctcct aagctgctga tctactgggc cagcaacaga     180
gaaagcggcg tgcccgatag attcagcggc tctggatctg gcaccgactt cacccctgaca    240 atcagctccc tgcaggccga ggatgtggcc gtgtactact gccagcagtt ctacagatac     300
cctctgacct tcggccaggg caccaaggtg gaactgaag                            339
```

ANTIBODY CAPABLE OF BLOCKING CD47-SIRPA INTERACTION AND APPLICATION THEREOF

CROSS-REFERENCE TO RELATED APPLICATIONS

This application is a National Stage application under 35 U.S.C. § 371 of International Application No. PCT/CN2019/090587, having an International Filing Date of Jun. 10, 2019, which claims priority to Chinese Application Serial No. 201810593389.3, filed on Jun. 11, 2018. The disclosure of the prior application is considered part of the disclosure of this application, and is incorporated in its entirety into this application.

TECHNICAL FIELD

The present disclosure relates to specific antibodies that target CD47, a manufacturing method therefor and use thereof.

BACKGROUND ART

CD47 (UniProt Q08722) is a transmembrane glycoprotein consisting of an N-terminal IgV-like extracellular region, a quintuple transmembrane region, and a short intracellular region. Since it was cloned from ovarian cancer tissue initially, CD47 was once considered to be a tumor antigen and its expression level was also associated with tumor progression. CD47 was later also found to be expressed on most normal cell surface, but is normally highly expressed in tumor cells.

CD47 exerts biological functions through interaction with its ligands. The inhibitory receptor signal regulatory protein SIRPα (CD172a, UniProt P78324) is one of the most important ligands of CD47. The interaction between CD47 and SIRPα is considered to be an important mechanism for macrophages to recognize self and non-self in the innate immune system. Oldenborg et al. found that the red blood cells of mice lacking CD47 were quickly cleared from the blood by splenic macrophages, while CD47 on normal red blood cells inhibited this phagocytosis by binding to SIRPα. Han et al. proved that anti-CD47 monoclonal antibody or CD47 fusion protein can block the fusion of macrophages.

Tumor cells also use the same mechanism to escape the killing of macrophages. Tumor cells usually express a high level of CD47 molecules on the cell membrane surface, so they are recognized as "self" by the body. Jaiswal et al. found that in tumor-bearing mice, human leukemia cells that highly expressed mouse CD47 molecules, can effectively escape the phagocytosis of mouse macrophages. In a mouse model of acute myeloid leukemia, Majeti et al. used the CD47 monoclonal antibodies that blocked the interaction of CD47 and SIRP, and found that, the leukemia cells in the bone marrow and peripheral blood of the mice in the treatment group were significantly reduced, and the long-term survival rate was also greatly improved. Chao et al. found that the combination of CD47 monoclonal antibody and rituximab has a significant synergistic effect. Weiskopf et al. found that high-affinity human SIRPα can effectively antagonize CD47 on cancer cells, and it also showed a synergistic effect with tumor-specific monoclonal antibodies.

CD47 antibodies can be used to treat a variety of CD47-positive hematomas and solid tumors, including non-Hodgkin's lymphoma (NHL), acute lymphocytic leukemia (ALL), acute myelogenous leukemia (AML), and chronic lymphocytic leukemia (CLL), chronic myelogenous leukemia (CML), multiple myeloma (MM), breast cancer, ovarian cancer, prostate cancer, head and neck cancer, bladder cancer, melanoma, colorectal cancer, pancreatic cancer, lung cancer, esophageal cancer, liver cancer, kidney cancer, smooth muscle cancer, leiomyosarcoma, glioma, glioblastoma, etc.

The occurrence of atherosclerosis may be related to the up-regulation of CD47. Apoptotic cells can resist the elimination of macrophages by up-regulating the expression of CD47. Kojima et al. found that CD47 blocking antibodies can normalize the clearance of diseased vascular tissue and improve the atherosclerosis in a variety of mouse models.

By the view of the role and function of CD47 in various related diseases, there is still a need in the art to develop improved anti-CD47 specific antibodies that suitable for treating patients. On the one hand, the antibody provided in this patent can specifically bind to the extracellular region of human CD47. On the other hand, the anti-CD47 antibody can hinder the binding between CD47 and SIRPα and promote the phagocytosis of macrophages, and said antibody doesn't cause the hemagglutination reaction, and has no obvious toxic effect in humanized transgenic mice.

SUMMARY OF THE INVENTION

In one aspect, the disclosure relates to an antibody or a functional fragment thereof that specifically binds to CD47.

An antibody or a functional fragment thereof according to the preceding aspect, comprising a heavy chain CDR selected from amino acid sequences SEQ ID NO: 2-4, 12-14, 22-24, 32-34, 42-44, 52-54, 62-64, 72-74, 82-84, 92-94, 102-104, 107-109, 112-114, 117-119, 122-124, 132-134, 137-139, 142-144, 147-149, 152-154 or any variant thereof, and/or a light chain CDR selected from amino acid sequences SEQ ID NO: 7-9, 17-19, 27-29, 37-39, 47-49, 57-59, 67-69, 77-79, 87-89, 97-99, 157-159, 162-164, 167-169, 172-174, 177-179 or any variant thereof.

An antibody or a functional fragment thereof according to the preceding aspect, comprising a heavy chain CDR1 selected from amino acid sequences SEQ ID NO: 2, 12, 22, 32, 42, 52, 62, 72, 82, 92, 102, 107, 112, 117, 122, 127, 132, 137, 142, 147, 152 or any variant thereof, a heavy chain CDR2 selected from amino acid sequences SEQ ID NO: 3, 13, 23, 33, 43, 53, 63, 73, 83, 93, 103, 108, 113, 118, 123, 128, 133, 138, 143, 148, 153 or any variant thereof, a heavy chain CDR3 selected from amino acid sequences SEQ ID NO: 4, 14, 24, 34, 44, 54, 64, 74, 84, 94, 104, 114, 119, 124, 129, 134, 139, 144, 149, 154 or any variant thereof; and/or a light chain CDR1 selected from amino acid sequences SEQ ID NO: 7, 17, 27, 37, 47, 57, 67, 77, 87, 97, 157, 162, 167, 172, 177 or any variant thereof, a light chain CDR2 selected from amino acid sequences SEQ ID NO: 8, 18, 28, 38, 48, 58, 68, 78, 88, 98, 158, 163, 168, 173, 178 or any variant thereof, a light chain CDR3 selected from amino acid sequences SEQ ID NO: 9, 19, 29, 39, 49, 59, 69, 79, 89, 99, 159, 164, 169, 174, 179 or any variant thereof.

The antibody or a functional fragment thereof according to the preceding aspect, comprising a heavy chain variable region selected from amino acid sequences SEQ ID NO: 1, 11, 21, 31, 41, 51, 61, 71, 81, 91, 101, 106, 111, 116, 121, 126, 131, 136, 141, 146, 151 or any variant thereof, and/or a light chain variable region selected from amino acid sequences SEQ ID NO: 6, 16, 26, 36, 46, 56, 66, 76, 86, 96, 156, 161, 166, 171, 176 or any variant thereof.

In one aspect, the present disclosure relates to an antibody or functional fragment thereof, comprising a heavy chain variable region selected from amino acid sequence SEQ ID NO:101 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:106 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:111 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:116 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:121 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:126 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:131 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:136 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:141 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:146 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:151 or any variant thereof, and/or a light chain variable region selected from amino acid sequences SEQ ID NO:156 or any variant thereof.

In one aspect, the present disclosure relates to an antibody or functional fragment thereof, comprising a heavy chain variable region selected from amino acid sequence SEQ ID NO:101 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:106 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:111 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:116 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:121 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:126 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:131 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:136 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:141 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:146 or any variant thereof, and/or a light chain variable region selected from amino acid sequences SEQ ID NO:161 or any variant thereof.

In one aspect, the present disclosure relates to an antibody or functional fragment thereof, comprising a heavy chain variable region selected from amino acid sequence SEQ ID NO:151 or any variant thereof, and/or a light chain variable region selected from amino acid sequences SEQ ID NO:161 or any variant thereof.

The antibody or functional fragment thereof of any of the preceding aspects, wherein the antibody is an antibody fragment.

The antibody or functional fragment thereof of any of the preceding aspects, wherein the antibody or functional fragment thereof inhibits the interaction of CD47 and SIRPα.

The antibody or functional fragment thereof of any of the preceding aspects, wherein the antibody or functional fragment thereof is humanized.

The antibody or functional fragment thereof, having at least 60%, 65%, 70%, 75%, 80%, 85%, 90%, 95%, 96%, 97%, 98%, 99% or more sequence identity to the antibody or functional fragment thereof of any of the preceding aspects.

A nucleic acid molecule encoding the antibody or functional fragment thereof of any of the preceding aspects, or a nucleic acid molecule having at least 60%, 65%, 70%, 75%, 80%, 85%, 90%, 95%, 96%, 97%, 98%, 99% or more sequence identity thereto.

A vector comprising the nucleic acid of any of the preceding aspects.

A cell comprising the vector of any of the preceding aspects.

A pharmaceutical composition comprising the antibody or functional fragment thereof, or the nucleic acid encoding same of any of the preceding aspects, and a pharmaceutically acceptable carrier.

A method for treating cancers, comprising the step of administering to the mammal a therapeutically effective amount of the antibody or functional fragment thereof, or the nucleic acid molecule, or the vector, or the cell or the pharmaceutical composition of any of the preceding aspects.

A method for treating diseases associated with abnormal production of CD47 in a mammal, comprising the step of administering to the mammal a therapeutically effective amount of the antibody or functional fragment thereof, or the nucleic acid molecule, or the vector, or the cell or the pharmaceutical composition of any of the preceding aspects.

Use of an antibody or functional fragment or nucleic acid molecule or vector or cell or pharmaceutical composition of any of the preceding aspects in the preparation of a medicament for the treatment of a disease associated with abnormal production of CD47 in a mammal.

Use of an antibody or functional fragment or nucleic acid molecule or vector or cell or pharmaceutical composition of any of the preceding aspects in the preparation of a medicament for the treatment of cancer in a mammal.

BRIEF DESCRIPTION OF THE DRAWINGS

FIG. 6-1. Using ELISA method to detect the binding of CD47 chimeric antibody to hCD47 at the antigen level; FIG. 6-2. Using ELISA method to detect the blocking detection of CD47-SIRPα by CD47 chimeric antibody at the antigen level; FIG. 6-3. Using FACS method to detect the binding of CD47 chimeric antibody to CD47 receptor on the cell surface at the cell level; FIG. 6-4. Using FACS method to detect the blocking detection of CD47-SIRPα by CD47 chimeric antibody at the cell level.

FIG. 12-1. ELISA results show that the humanized CD47 antibody binds to hCD47 at the antigen level; FIG. 12-2. ELISA results show that the humanized CD47 antibody has the biological activity of blocking the CD47-SIRPα at the antigen level; FIG. 12-3. FACS results show that the humanized CD47 antibody binds to the CD47 expressed by the cells at the cell level; FIG. 12-4. FACS results show that the humanized CD47 antibody has the biological activity of blocking the CD47-SIRPα at the cell level.

SEQUENCE LISTING

Figures 1, 2:
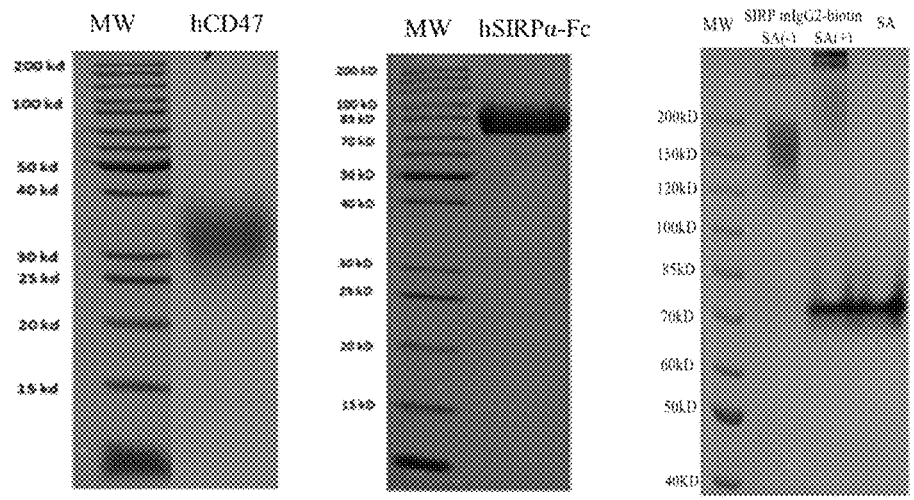
FIG. 1. N-terminal extracellular structural domain protein of recombinant human CD47 molecule, due to glycosylation, shows size of about 35 KDa on reduced SDS-PAGE; the size of the human SIRPα-Fc fusion protein is about 80 KDa after reduction.
FIG. 2. Non-reducing SDS-PAGE shows an overall upward migration after biotinylated SIRPα-Fc fusion protein binding with streptavidin, the biotinylation efficiency is 100%.

This application contains a sequence listing submitted electronically in ASCII format file named sequence.txt. The ASCII file, created on Dec. 11, 2020, is 74,219 bytes in size. The material in the txt file is hereby incorporated by reference

DETAILED DESCRIPTION OF EMBODIMENTS

I. Definitions

In the present invention, all scientific and technical terms used herein have the meanings commonly understood by a person skilled in the art unless specified otherwise. In addition, terms and laboratory operation steps related to the protein and nucleic acid chemistry, molecular biology, cell and tissue culture, microbiology and immunology as used herein are terms and conventional steps that are widely used in the corresponding art. To better understand the present invention, definitions and explanations of related terms are provided below.

In one aspect, provided herein are antibodies (e.g., monoclonal antibodies) and antigen-binding fragments thereof that specifically bind to CD47 (e.g., human CD47). In specific aspects, such anti-CD47 antibodies block the binding of CD47 to SIRPα, promote phagocytosis, have reduced Fc effector function or no Fc effector function (for example, binding to FcγR, ADCC or CDC), and/or have little or no agglutination (eg, hemagglutination) activity.

In specific aspects, provided herein is a monoclonal anti-CD47 antibody that specifically binds to human CD47, wherein the anti-CD47 antibody is a variant of the parent antibody. In specific aspects, the anti-CD47 antibodies expressed in the CF system provided herein are non-glycosylated. In specific aspects, provided herein are antibodies that specifically bind CD47 (e.g., human CD47). In a specific aspect, provided herein is an anti-CD47 antibody comprising one or more modifications in amino acid residues (for example, 5-13 amino acid substitutions in the framework region of the heavy chain variable region), and compared with the parent antibody without such modifications, it maintains the affinity to the antigen. In certain aspects, in vivo or in vitro, or both in vivo and in vitro, such anti-CD47 antibodies inhibit the interaction of SIRPα and CD47, are non-glycosylated, promote phagocytosis, and have anti-tumor activities (e.g., do not promote agglutination (eg, hemagglutination)), and/or have low or no Fc effector function (eg, binding to FcγR, ADCC, or CDC).

In certain embodiments, the antibody or antigen-binding fragment described herein may comprise sequences that do not naturally exist within the antibody germline repertoire in animals or mammals (e.g., humans).

As used herein and unless otherwise stated, the term "about" or "approximately" means within plus or minus 10% of a given value or range. The term refers to within plus or minus 10% of a given value or range, rounded up or down to the nearest integer, when an integer is required.

As used herein, the terms "CD47" or "integrin-related protein" or "IAP" or "ovarian cancer antigen" or "OA3" or "Rh-related antigen" or "MERG" refer to a multi-spanning transmembrane receptor belonging to the immunoglobulin superfamily that can be interchangeably used.

The terms "red blood cell" and "erythrocyte" are synonymous and are used interchangeably herein.

The term "agglutination" refers to cellular clumping, while the term "hemagglutination" refers to clumping of a specific subset of cells, i.e., red blood cells. Therefore, hemagglutination is a kind of agglutination.

The phrase "substantially identical" with respect to an antibody chain polypeptide sequence may be construed as an antibody chain exhibiting at least 60%, 65%, 70%, 75%, 80%, 85%, 90%, 95%, 96%, 97%, 98%, 99% or more sequence identity to the reference polypeptide sequence. The term with respect to a nucleic acid sequence may be construed as a sequence of nucleotides exhibiting at least about 60%, 65%, 70%, 75%, 80%, 85%, 90%, 95%, 96%, 97%, 98%, 99% or more sequence identity to the reference nucleic acid sequence.

The terms, "identity" or "homology" may mean the percentage of nucleotide bases or amino acid residues in the candidate sequence that are identical to the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are readily available and well known in the art. Sequence identity may be measured using sequence analysis software.

The phrases and terms "functional fragment, variant, derivative or analog" and the like, as well as various forms thereof, of an antibody or antigen is a compound or molecule having qualitative biological activity in common with a full-length antibody or antigen of interest. For example, a functional fragment or analog of an anti-CD47 antibody is one which can bind to an CD47 molecule or one which can prevent or substantially reduce the ability of a ligand or an agonistic or antagonistic antibody, to bind to CD47.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The multiple substitutions may be at consecutive sites. Also, one amino acid can be substituted with multiple residues, in which case such a variant comprises both a substitution and an insertion. "Insertional" variants are those with one or more amino acids inserted immediately adjacent to an amino acid at a particular position in a native sequence. Immediately adjacent to an amino acid means linked to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

As used herein, the term "antibodies" is used in the broadest sense, and specifically covers monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. "Antibodies" can also refer to immunoglobulins and immunoglobulin fragments, whether produced naturally or partially or fully synthetically (e.g., recombinantly), including any fragment thereof which comprises at least a partial variable region of an immunoglobulin molecule and retains the binding specificity of the full length of the immunoglobulin molecule. Thus, antibodies include any protein having a binding domain which is homologous or substantially homologous to an immunoglobulin antigen binding domain (an antibody binding site). Antibodies include antibody fragments, such as anti-tumor stem cell antibody fragments. As used herein, the term antibody thus includes synthetic antibodies, recombinantly-produced antibodies, multispecific antibodies (e.g., bispecific antibodies), human antibodies, non-human antibodies, humanized antibodies, chimeric antibodies, intrabodies, and antibody fragments, for example without limitation, Fab fragments, Fab' fragments, F(ab')2 fragments, Fv fragments, disulfide-linked Fv (dsFv), Fd fragments, Fd' fragments, single-chain Fv (scFv), single-chain Fab (scFab), diabodies, anti-idiotypic (anti-Id) antibodies, or antigen-binding fragments of any of the above-mentioned antibodies. The antibodies provided herein include any immunoglobulin class (e.g., IgG, IgM, IgD, IgE, IgA, and IgY), and members of any type (e.g., IgG1, IgG2, IgG3, IgG4, IgA1, and IgA2) or subtype (e.g., IgG2a and IgG2b).

The antibodies of the present invention may be antibodies of any class (e.g., IgG, IgE, IgM, IgD, IgA, etc.), or subclass (e.g., $IgG_1$, $IgG_2$, $IgG_{2a}$, $IgG_3$, $IgG_4$, $IgA_1$, $IgA_2$, etc.) ("type" and "class", as well as "subtype" and "subclass" are used interchangeably herein). Native or wildtype (that is, obtained from a non-artificially manipulated member of a population) antibodies and immunoglobulins are usually heterotetrameric glycoproteins of about 150,000 daltons, which are composed of two identical light (L) chains and two identical heavy (H) chains. Each heavy chain has at one end a variable domain (VH) followed by a number of constant domains. Each light chain has a variable domain at one end (VL) and a constant domain at the other end. By "non-artificially manipulated" is meant not treated to contain or express a foreign antigen binding molecule. Wild type can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-CD47 antibody" means an antibody or polypeptide derived therefrom (a derivative) which binds specifically to CD47 as defined herein, including, but not limited to, molecules which inhibit or substantially reduce the binding of CD47 to its ligands or inhibit CD47 activity.

The term "variable" in the context of a variable domain of antibodies, refers to certain portions of the pertinent molecules which differ extensively in sequences between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) or hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, linked by three CDRs, wherein the CDRs form loops connecting, and in some cases form part of, the β-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, MD (1987)). As used herein, numbering of immunoglobulin amino acid residues is done using the immunoglobulin amino acid residue numbering system of Kabat et al., unless otherwise indicated. One CDR can carry the ability to bind specifically to the cognate epitope.

The term "hinge" or "hinge region" as used herein refers to a flexible polypeptide comprising amino acids between the first and second constant domains of an antibody.

As used herein, "antibody fragments" or "antigen-binding fragments" of antibodies refer to any portion of a full length antibody that is less than the full length, but comprises at least a portion of the variable region of the antibody that binds to the antigen (e.g., one or more CDRs and/or one or more antibody binding sites), and thus retain binding specificity as well as at least partial specific binding ability of the full length antibody. Thus, antigen-binding fragments refer to antibody fragments comprising an antigen-binding portion that binds to the same antigen as the antibody from which the antibody fragments are derived. Antibody fragments include antibody derivatives produced by enzymatic treatment of full length antibodies, and derivatives produced by the synthesis, such as recombinantly-produced derivatives. Antibodies include antibody fragments. Examples of antibody fragments include, but are not limited to, Fab, Fab', F(ab')2, single chain Fv (scFv), Fv, dsFv, diabodies, Fd and Fd' fragments, and other fragments, including modified fragments (see, for example, Methods in Molecular Biology, Vol 207: Recombinant Antibodies for Cancer Therapy Methods and Protocols (2003); Chapter 1; p 3-25, Kipriyanov). The fragments may comprise a plurality of chains joined together, for example via a disulfide bond and/or via a peptide linker. Antibody fragments usually comprise at least or about 50 amino acids, and typically at least or about 200 amino acids. Antigen-binding fragments include any antibody fragments, upon the antibody fragments are inserted into an antibody framework (e.g., by substitution of a corresponding region), an antibody that immunospecifically binds (i.e., exhibiting at least or at least about $10^7$-$10^8$ $M^{-1}$ of Ka) antigens is obtained. "Functional fragments" or "analogs of anti-CD47 antibodies" are fragments or analogs which prevent or substantially reduce the ability of the receptors to bind to ligands or initiate signal transduction. As used herein, functional fragments generally have the same meaning as "antibody fragments" and, in the case of antibodies, may refer to fragments which prevent or substantially reduce the ability of the receptors to bind to ligands or initiate signal transduction, such as $F_v$, $F_{ab}$ and $F_{(ab')2}$ et al. "$F_v$" fragments consist of dimers ($V_H$-$V_L$ dimers) formed by a variable domain of a heavy chain and a variable domain of a light chain by non-covalent binding. It is in this configuration that the three CDRs of each variable domain interact to define a target binding site on the surface of the $V_H$-$V_L$ dimer, as is the case with an intact antibody. Collectively, the six CDRs confer antigen-binding specificity to the intact antibody. However, even a single variable domain (or half of an $F_v$ comprising only 3 CDRs specific for a target) has the ability to recognize and bind targets.

"Single-chain $F_v$", "s$F_v$" or "scab" antibody fragments comprise $V_H$ and $V_L$ domains of antibodies, wherein these domains are present in a single polypeptide chain. Generally, the $F_v$ polypeptide further comprises a polypeptide linker between the $V_H$ and $V_L$, which is typically a flexible molecule that enables the sFv to form the desired structure for target binding.

The term "diabody" refers to antibody fragments having two antigen-binding sites, the antibody fragments can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with the binding domains of another chain and create two antigen-binding sites.

$F_{ab}$ fragments comprise the variable and constant domains of the light chain as well as the variable and first constant domain ($C_{H1}$) of the heavy chain. $F_{ab}$ fragments differ from $F_{ab}$ fragments by the addition of a few residues at the carboxyl terminus of the $C_{H1}$ domain to include one or more cysteines from the antibody hinge region. $F_{ab}$ fragments can be produced by cleavage of the disulfide bond at the hinge cysteines of the pepsin digestion product of $F_{(ab')2}$. Additional enzymatic and chemical treatments of antibodies can yield other functional fragments of interest.

The term "linear Fab" refers to a tetravalent antibody as described by Miller et al. (Miller et al. (2003), J Immunol. 170: 4854-4861). The "linear Fab" is composed of a tandem of the same CH1-VH domain, paired with the identical light chain at each CH1-VH position. These molecules have been developed in order to increase the valency of an antibody to enhance its functional affinity through the avidity effect, but they are monospecific.

As used herein, the "monoclonal antibody" refers to a population of identical antibodies, i.e., each individual antibody molecule in the population of the monoclonal antibody is identical to other antibody molecules. This property is in contrast to the property of a polyclonal population of antibodies, which comprises antibodies having a plurality of different sequences. Monoclonal antibodies can be prepared by many well-known methods (Smith et al. (2004) J. Clin. Pathol. 57, 912-917; and Nelson et al., J Clin Pathol (2000), 53, 111-117). For example, monoclonal antibodies can be prepared by immortalizing B cells, e.g., by fusion with myeloma cells to produce a hybridoma cell line or by infecting B cells with a virus such as EBV. Recombinant techniques can also be used to prepare antibodies from a clonal population of host cells by in vitro transforming the host cells with a plasmid carrying an artificial sequence of a nucleotide encoding the antibodies.

As used herein, the term "hybridoma" or "hybridoma cell" refers to a cell or cell line (typically a myeloma or lymphoma cell) produced by the fusion of antibody-producing lymphocytes and antibody-producing cancer cells. As is known to one of ordinary skill in the art, hybridomas can proliferate and continue to supply to produce specific monoclonal antibodies. Methods for producing hybridomas are known in the art (see, for example, Harlow & Lane, 1988). The term "hybridoma" or "hybridoma cell" when referred herein also includes subclones and progeny cells of the hybridoma.

As used herein, "conventional antibody" refers to an antibody comprising two heavy chains (which may be designated H and H') and two light chains (which may be designated L and L') and two antigen-binding sites, wherein each heavy chain can be a full length immunoglobulin heavy chain or any functional region thereof that retain the antigen binding ability (for example, the heavy chains include, but not limited to, VH chains, VH-CH1 chains, and VH-CH1-CH2-CH3 chains), and each light chain can be a full length light chain or any functional region (e.g., light chains include, but not limited to, VL chains and VL-CL chains). Each heavy chain (H and H') is paired with a light chain (L and L', respectively).

As used herein, a full length antibody is an antibody comprising two full length heavy chains (e.g., VH-CH1-CH2-CH3 or VH-CH1-CH2-CH3-CH4) and two full length light chains (VL-CL) and a hinge region, for example, an antibody naturally produced by secretion of the antibody by B cells, and a synthetically-produced antibody having the same domain.

As used herein, dsFv refers to an Fv having an engineered intermolecular disulfide bond which stabilizes the VH-VL pair.

As used herein, a Fab fragment is an antibody fragment that results from digestion of a full-length immunoglobulin with papain, or a fragment having the same structure, which is synthesized or produced, for example, by recombinant methods. The Fab fragment comprises a light chain (comprising VL and CL) and another chain comprising a variable domain (VH) of the heavy chain and a constant region domain (CH1) of the heavy chain.

As used herein, an F(ab')2 fragment is an antibody fragment that results from digestion of an immunoglobulin with pepsin at pH 4.0-4.5, or a fragment having the same structure, which is synthesized or produced, for example, by recombinant methods. A F(ab')2 fragment essentially comprises two Fab fragments, wherein each heavy chain portion comprises an additional few amino acids, including cysteines that forms a disulfide bond connecting the two fragments.

As used herein, a Fab' fragment is a fragment comprising half of a F(ab')2 fragment (comprising ne heavy chain and one light chain).

As used herein, a scFv fragment refers to an antibody fragment comprising a variable light chain (VL) and a variable heavy chain (VH) covalently linked by a polypeptide linker in any order. The linker is of a length such that the two variable domains are bridged without substantial interference. Exemplary linkers are (Gly-Ser)n residues with some Glu or Lys residues dispersed throughout to increase solubility.

The term "chimeric antibody" refers to an antibody in which the variable region sequence is derived from one species and the constant region sequence is derived from another species, for example, in which the variable region sequence is derived from a mouse antibody and the constant region sequence is derived from a human antibody.

"Humanized" antibody refers to a non-human (e.g., mouse) antibody form that is a chimeric immunoglobulin, immunoglobulin chain, or a fragment thereof (e.g., Fv, Fab, Fab', F(ab')2 or other antigen-binding subsequences of antibodies), and contains minimal sequences derived from non-human immunoglobulins. Preferably, the humanized antibody is a human immunoglobulin (recipient antibody) in which residues of the complementarity determining region (CDR) of the recipient antibody are replaced by residues of the CDR of a non-human species (donor antibody) having the desired specificity, affinity, and capacity, such as mouse, rat, rabbit.

Furthermore, it is also possible in humanization process to mutate amino acid residues within the CDR1, CDR2 and/or CDR3 regions of VH and/or VL, thereby improving one or more binding properties (e.g., affinity) of the antibody. Mutations can be introduced, for example, by PCR-mediation, the effect of the mutations on antibody binding or other functional properties can be assessed using in vitro or in vivo assays as described herein. Typically, conservative mutations are introduced. Such mutations may be amino acid substitutions, additions or deletions. In addition, the number of mutations within the CDRs is usually one or at most two. Thus, the humanized antibodies of the present invention also encompass antibodies comprising one or two amino acid mutations within the CDRs.

As used herein, the term "epitope" refers to any antigenic determinant on an antigen to which the paratope of an antibody binds. Epitopic determinants usually comprise chemically active surface groupings of molecules such as amino acids or sugar side chains, and typically have specific three dimensional structural characteristics, as well as specific charge characteristics.

As used herein, a variable domain or variable region is a specific Ig domain of the heavy or light chain of an antibody, comprising an amino acid sequence that varies between different antibodies. Each light chain and each heavy chain have a variable region domain VL and VH, respectively. The variable domain provides antigen specificity and is therefore responsible for antigen recognition. Each variable region comprises a CDR and a framework region (FR), wherein the CDR is a part of an antigen-binding site domain.

As used herein, "antigen-binding domain" and "antigen-binding site" are used synonymously to refer to a domain within an antibody that recognizes and physically interacts with a cognate antigen. Native conventional full length antibody molecules have two conventional antigen-binding sites, each comprising a heavy chain variable region portion and a light chain variable region portion. Conventional antigen-binding sites comprise a loop connecting the anti-parallel beta strands within the variable region domain. The antigen-binding site may comprise other portions of the variable region domain. Each conventional antigen-binding site comprises 3 hypervariable regions from the heavy chain and 3 hypervariable regions from the light chain. The hypervariable regions are also referred to as complementarity determining regions (CDRs).

As used herein, "hypervariable region", "HV", "complementarity determining region" and "CDR" and "antibody CDR" are used interchangeably to refer to one of a plurality of portions within each variable region that together form an antigen binding site of the antibody. Each variable region domain contains 3 CDRs, designated as CDR1, CDR2 and CDR3. For example, the light chain variable region domain comprises 3 CDRs, designated as VL CDR1, VL CDR2 and VL CDR3; the heavy chain variable region domain comprises 3 CDRs, designated as VH CDR1, VH CDR2 and VH CDR3. 3 CDRs in the variable region are discontinuous along the linear amino acid sequence, but are in close proximity in the folded polypeptide. The CDRs are located within the loop connecting the parallel strand of the beta sheet of the variable domains. As described herein, a person skilled in the art are aware of and can identify CDRs based on Kabat or Chothia numbering (see, for example, Kabat, E. A. et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917).

As used herein, a framework region (FR) is a domain in an antibody variable region domain in a beta sheet; in terms of amino acid sequence, the FR region is relatively more conserved than the hypervariable region.

As used herein, a "constant region" domain is a domain in an antibody heavy or light chain that comprises an amino acid sequence that is relatively more conserved than the amino acid sequence of the variable region domain. In a conventional full length antibody molecule, each light chain has a single light chain constant region (CL) domain, and each heavy chain comprises one or more heavy chain constant region (CH) domains, including CH1, CH2, CH3 and CH4. The full length IgA, IgD and IgG isotypes comprise CH1, CH2, CH3 and the hinge region, whereas IgE and IgM comprise CH1, CH2, CH3 and CH4. The CH1 and CL domains extend the $F_{ab}$ arm of the antibody molecule, thus facilitating interaction with the antigen and rotation of the antibody arm. The constant region of an antibody can perform an effector function, for example, but not limited to, clearance of antigens, pathogens, and toxins to which the antibody specifically binds, such as by interaction with various cells, biomolecules, and tissues.

As used herein, a functional region of an antibody is an antibody portion comprising at least VH, VL, CH (e.g., CH1, CH2 or CH3), CL or a hinge region domain or at least a functional region thereof of the antibody.

As used herein, a functional region of a VH domain is at least a portion of an intact VH domain that retains at least part of the binding specificity of the entire VH domain (e.g., by retaining one or more CDRs of the entire VH domain), such that the functional region of the VH domain binds to the antigen either alone or in combination with another antibody domain (e.g., a VL domain) or a region thereof. The functional region of an exemplary VH domain is a region comprising CDR1, CDR2 and/or CDR3 of the VH domain.

As used herein, a functional region of a VL domain is at least a portion of an intact VL domain that retains at least part of the binding specificity of the entire VL domain (e.g., by retaining one or more CDRs of the entire VL domain), such that the functional region of the $V_L$ domain binds to the antigen either alone or in combination with another antibody domain (e.g., a $V_H$ domain) or a region thereof. The functional region of an exemplary $V_L$ domain is a region comprising CDR1, CDR2 and/or CDR3 of the $V_L$ domain.

As used herein, "specifically bind" or "immunospecifically binding" with respect to an antibody or antigen-binding fragment thereof is used interchangeably herein and refers to the ability of an antibody or antigen-binding fragment to form one or more non-covalent bonds with an alloantigen via non-covalent interactions between the antibody and the antibody-binding site of the antigen. The antigen can be an isolated antigen or present in a tumor cell. Typically, an antibody that immunospecifically binds (or specifically binds) to an antigen binds to the antigen with an affinity constant Ka of about $1\times10^7 M^{-1}$ or $1\times10^8 M^{-1}$ or more (or with a dissociation constant (Kd) of $1\times10^{-7} M$ or $1\times10^{-8} M$ or less). Affinity constants can be determined by standard kinetic methods of antibody responses, for example, immunoassays, surface plasmon resonance (SPR) (Rich and Myszka (2000) Curr. Opin. Biotechnol 11:54; Englebienne (1998) Analyst. 123:1599), isothermal titration calorimetry (ITC) or other kinetic interaction assays known in the art (see, for example, Paul, ed., Fundamental Immunology, 2nd ed., Raven Press, New York, pages 332-336 (1989); see also U.S. Pat. No. 7,229,619, which describes exemplary SPR and ITC methods for calculating the binding affinity of antibodies). Instruments and methods for detecting and monitoring the rate of binding in real time are known and commercially available (see, BiaCore 2000, Biacore AB, Upsala, Sweden and GE Healthcare Life Sciences; Malmqvist (2000) Biochem. Soc. Trans. 27:335).

As used herein, the term "competing" with respect to an antibody means that a first antibody or antigen-binding fragment thereof binds to an epitope in a manner sufficiently similar to a second antibody or antigen-binding fragment thereof, and thus the binding result of the first antibody to the associated epitope thereof is detectably reduced in the presence of the second antibody compared to that in the absence of the second antibody; alternatively, the binding of the second antibody to the associated epitope thereof may be, but not necessarily, detectably reduced in the presence of the first antibody compared to that in the absence of the first antibody. That is to say, the first antibody can inhibit the binding of the second antibody to the epitope thereof, however, the second antibody is not necessarily to inhibit the binding of the first antibody to the corresponding epitope thereof. However, in the case where each antibody can detectably inhibit the binding of another antibody to the associated epitope or ligand thereof, whether in an identical, higher or lower degree, the antibodies are referred to as "cross-competitively" binding to the corresponding epitope thereof. Both competing and cross-competing antibodies are encompassed by the present invention. Regardless of the mechanism of such competing or cross-competing (e.g., steric hindrance, conformational change, or binding to a common epitope or a fragment thereof), a person skilled in the art will recognize that, based on the teachings provided in the present invention, that such competing and/or cross-competing antibodies are encompassed by the present invention and can be used in the methods disclosed herein.

As used herein, "polypeptide" refers to two or more amino acids which are linked covalently. The terms "polypeptide" and "protein" are used interchangeably herein.

"Isolated protein", "isolated polypeptide" or "isolated antibody" refers to a protein, polypeptide or antibody: (1) is not associated with naturally associated components that accompany it in its native state; (2) is free of other proteins from the same species; (3) is expressed by a cell from a different species; or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, i.e., using the protein purification technique well known in the art.

Suitable conservative amino acid substitutions in peptides or proteins are known to a person skilled in the art and can generally be carried out without altering the biological activity of the resulting molecule. Typically, a person skilled in the art will recognize that a single amino acid substitution in a non-essential region of a polypeptide does not substantially alter the biological activity (see, for example, Watson et al., Molecular Biology of the Gene, 4th Edition, 1987, The Benjamin/Cummings Pub. co., p. 224).

As used herein, the terms "polynucleotide" and "nucleic acid molecule" refer to an oligomer or polymer comprising at least two linked nucleotides or nucleotide derivatives, including deoxyribonucleic acid (DNA) and ribonucleic acid (RNA), which are usually linked by a phosphodiester bond.

As used herein, an isolated nucleic acid molecule is a nucleic acid molecule which is isolated from other nucleic acid molecules present in the natural source of the nucleic acid molecule. An "isolated" nucleic acid molecule of, for example, a cDNA molecule, can be substantially free of other cellular material or culture medium when prepared by recombinant techniques, or substantially free of chemical precursors or other chemical components during the chemical synthesis. Exemplary isolated nucleic acid molecules provided herein include isolated nucleic acid molecules encoding the provided antibodies or antigen-binding fragments.

"identical" or "identity" with respect to a sequence has well-recognized meaning in the art, and the percentage of sequence identity between two nucleic acid or polypeptide molecules or regions can be calculated using the disclosed techniques. Sequence identity can be measured along the entire length of a polynucleotide or polypeptide or along a region of the molecule. (See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Although there are many methods for measuring the identity between two polynucleotides or polypeptides, the term "identity" is well known to a person skilled person (Carrillo, H. & Lipman, D., SIAM J Applied Math 48:1073(1988)).

As used herein, "operably linked" with respect to a nucleic acid sequence, region, element or domain means that the nucleic acid regions are functionally related to each other. For example, a promoter can be operably linked to a nucleic acid encoding a polypeptide which enables the promoter to regulate or mediate the transcription of the nucleic acid.

As used herein, "expression" refers to the process by which a polypeptide is produced by transcription and translation of a polynucleotide. The expression level of a polypeptide can be assessed using any method known in the art, including, for example, methods for determining the amount of polypeptides produced from a host cell. Such methods can include, but not limited to, quantification of polypeptides in cell lysates by ELISA, Coomassie blue staining after gel electrophoresis, Lowry protein assays, and Bradford protein assays.

As used herein, a "host cell" refers to a cell used to receive, maintain, replicate, and amplify a vector. Host cells can also be used to express the polypeptide encoded by the vector. The nucleic acid contained in the vector replicates when the host cell divides, thereby amplifying the nucleic acid. Host cells can be eukaryotic cells or prokaryotic cells. Suitable host cells include, but not limited to, CHO cells, various COS cells, HeLa cells, HEK cells such as HEK 293 cells.

"Codon optimization" refers to a method for modifying a nucleic acid sequence for enhanced expression in a host cell of interest by replacing at least one codon (e.g., about or more than about 1, 2, 3, 4, 5, 10, 15, 20, 25, 50 or more codons) of the native sequence with codons that are more frequently or most frequently used in the genes of the host cell while maintaining the native amino acid sequence. Various species exhibit particular bias for certain codons of a particular amino acid. Codon preference (a difference in codon usage between organisms) usually correlates with the efficiency of translation of messenger RNA (mRNA), which is in turn believed to be dependent on the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the Codon Usage Database available at www.kazusa.orjp/codon/, and these tables can be adapted in different ways. See, Nakamura Y. et al., "Codon usage tabulated from the international DNA sequence databases: status for the year 2000. Nucl. Acids Res., 28:292(2000).

As used herein, a "vector" is a replicable nucleic acid and when a vector is transformed into a suitable host cell, one or more heterologous proteins can be expressed from the vector. The vector as used herein includes the vector into which a nucleic acid encoding a polypeptide or a fragment thereof can be introduced, typically, by restriction digestion and ligation. The vector as used herein also includes the vector comprising a nucleic acid encoding a polypeptide. The vector is used to introduce a nucleic acid encoding a polypeptide into a host cell, to amplify the nucleic acid, or to express/display a polypeptide encoded by a nucleic acid. The vector typically remains free, but can be designed to integrate the gene or a part thereof into the chromosome of the genome. The vectors of artificial chromosomes, such as yeast artificial vectors and mammalian artificial chromosomes, are also taken into consideration. The selection and use of such vehicles are well known to a person skilled in the art.

As used herein, vectors also include "viral vectors" or "vectors of viruses". The vector of virus is an engineered virus, which can be operably linked to an exogenous gene to transfer (as a vehicle or shuttle) the exogenous gene into a cell.

As used herein, an "expression vector" includes a vector capable of expressing DNA, which can be operably linked to a regulatory sequence, such as a promoter region, that is capable of affecting expression of such DNA fragments. Such additional fragments may include promoter and terminator sequences, and may optionally include one or more origins of replication, one or more selectable markers, an enhancer, a polyadenylation signal, etc. Expression vectors are generally derived from plasmid or viral DNA, or may contain elements of both. Thus, an expression vector refers to a recombinant DNA or RNA construct, such as a plasmid, phage, recombinant virus, or other vector which, when introduced into a suitable host cell, results in expression of the cloned DNA. Suitable expression vectors are well known to a person skilled in the art and include expression vectors which are replicable in eukaryotic cells and/or prokaryotic cells, and expression vectors which retain free or expression vectors which are integrated into the genome of a host cell.

As used herein, "treating" an individual having a disease or condition means that the symptoms of the individual are partially or totally relieved, or unchanged after treatment. Thus, treating includes preventing, treating, and/or curing. Preventing refers to the prevention of underlying diseases and/or prevention of worsening symptoms or disease progression. Treating also includes any pharmaceutical use of any of the provided antibodies or antigen-binding fragments thereof and the compositions provided herein.

As used herein, "therapeutic effect" refers to an effect caused by the treatment in an individual that alters, generally ameliorates or improves the symptoms of diseases or conditions, or cures diseases or conditions.

As used herein, "therapeutically effective amount" or "therapeutically effective dose" refers to an amount of a substance, compound, material, or composition comprising the compound which is at least sufficient to produce a therapeutic effect when administered to a subject. Thus, it is an amount essential for preventing, curing, ameliorating, blocking or partially blocking the symptoms of a disease or condition.

As used herein, "prophylactically effective amount" or "prophylactically effective dose" refers to an amount of a substance, compound, material or composition comprising the compound which exerts the desired prophylactic effect when administered to a subject, e.g., to prevent or delay the onset or recurrence of a disease or symptom, reduce the likelihood of the occurring or recurring of a disease or symptom. The complete prophylacti effective dose does not necessarily occur by administration of one dose and can occur upon administration of a series of doses. Thus, a prophylactically effective amount can be administered in one or more administrations.

As used herein, the term "patient" refers to a mammal, such as human.

In one aspect, the disclosure relates to an antibody or a functional fragment thereof, comprising a heavy chain CDR selected from the amino acid sequences SEQ ID NO: 2-4, 12-14, 22-24, 32-34, 42-44, 52-54, 62-64, 72-74, 82-84, 92-94, 102-104, 107-109, 112-114, 117-119, 122-124, 132-134, 137-139, 142-144, 147-149, 152-154 or any variant thereof, and/or a light chain CDR selected from the amino acid sequences of SEQ ID NO: 7-9, 17-19, 27-29, 37-39, 47-49, 57-59, 67-69, 77-79, 87-89, 97-99, 157-159, 162-164, 167-169, 172-174, 177-179 or any variant thereof.

In one aspect, the disclosure relates to an antibody or a functional fragment thereof, comprising a heavy chain CDR1 selected from the amino acid sequences SEQ ID NO: 2, 12, 22, 32, 42, 52, 62, 72, 82, 92, 102, 107, 112, 117, 122, 127, 132, 137, 142, 147, 152 or any variant thereof, a heavy chain CDR2 selected from the amino acid sequences of SEQ ID NO: 3, 13, 23, 33, 43, 53, 63, 73, 83, 93, 103, 108, 113, 118, 123, 128, 133, 138, 143, 148, 153 or any variant thereof, a heavy chain CDR3 selected from the amino acid sequences of SEQ ID NO: 4, 14, 24, 34, 44, 54, 64, 74, 84, 94, 104, 114, 119, 124, 129, 134, 139, 144, 149, 154 or any variant thereof; and/or a light chain CDR1 selected from amino acid sequences of SEQ ID NO: 7, 17, 27, 37, 47, 57, 67, 77, 87, 97, 157, 162, 167, 172, 177 or any variant thereof, a light chain CDR2 selected from amino acid sequences of SEQ ID NO: 8, 18, 28, 38, 48, 58, 68, 78, 88, 98, 158, 163, 168, 173, 178 or any variant thereof, a light chain CDR3 selected from amino acid sequences SEQ ID NO: 9, 19, 29, 39, 49, 59, 69, 79, 89, 99, 159, 164, 169, 174, 179 or any variant thereof.

In one aspect, the disclosure relates to an antibody or a functional fragment thereof, comprising a heavy chain variable region selected from the amino acid sequences SEQ ID NO: 1, 11, 21, 31, 41, 51, 61, 71, 81, 91, 101, 106, 111, 116, 121, 126, 131, 136, 141, 146, 151 or any variant thereof, and/or a light chain variable region selected from amino acid sequences SEQ ID NO: 6, 16, 26, 36, 46, 56, 66, 76, 86, 96, 156, 161, 166, 171, 176 or any variant thereof.

In one aspect, the disclosure relates to an antibody or a functional fragment thereof, comprising a heavy chain CDR1 selected from the amino acid sequence SEQ ID NO: 2, a heavy chain CDR2 selected from the amino acid sequence SEQ ID NO: 3, and a heavy chain CDR3 selected from the amino acid sequence SEQ ID NO: 4; and/or a light chain CDR1 selected from the amino acid sequence SEQ ID NO: 7, a light chain CDR2 selected from the amino acid sequence SEQ ID NO: 8, and a light chain CDR3 selected from the amino acid sequence SEQ ID NO: 9.

In one aspect, the disclosure relates to an antibody or a functional fragment thereof, comprising a heavy chain CDR1 selected from the amino acid sequence SEQ ID NO: 12, a heavy chain CDR2 selected from the amino acid sequence SEQ ID NO: 13, and a heavy chain CDR3 selected from the amino acid sequence SEQ ID NO: 14; and/or a light chain CDR1 selected from the amino acid sequence SEQ ID NO: 17, a light chain CDR2 selected from the amino acid sequence SEQ ID NO: 18, and a light chain CDR3 selected from the amino acid sequence SEQ ID NO: 19.

In one aspect, the disclosure relates to an antibody or a functional fragment thereof, comprising a heavy chain CDR1 selected from the amino acid sequence SEQ ID NO: 22, a heavy chain CDR2 selected from the amino acid sequence SEQ ID NO: 23, and a heavy chain CDR3 selected from the amino acid sequence SEQ ID NO: 24; and/or a light chain CDR1 selected from the amino acid sequence SEQ ID NO: 27, a light chain CDR2 selected from the amino acid sequence SEQ ID NO: 28, and a light chain CDR3 selected from the amino acid sequence SEQ ID NO: 29.

In one aspect, the disclosure relates to an antibody or a functional fragment thereof, comprising a heavy chain CDR1 selected from the amino acid sequence SEQ ID NO: 32, a heavy chain CDR2 selected from the amino acid sequence SEQ ID NO: 33, and a heavy chain CDR3 selected from the amino acid sequence SEQ ID NO: 34; and/or a light chain CDR1 selected from the amino acid sequence SEQ ID NO: 37, a light chain CDR2 selected from the amino acid sequence SEQ ID NO: 38, and a light chain CDR3 selected from the amino acid sequence SEQ ID NO: 39.

In one aspect, the disclosure relates to an antibody or a functional fragment thereof, comprising a heavy chain CDR1 selected from the amino acid sequence SEQ ID NO: 42, a heavy chain CDR2 selected from the amino acid sequence SEQ ID NO: 43, and a heavy chain CDR3 selected from the amino acid sequence SEQ ID NO: 44; and/or a light chain CDR1 selected from the amino acid sequence SEQ ID NO: 47, a light chain CDR2 selected from the amino acid sequence SEQ ID NO: 48, and a light chain CDR3 selected from the amino acid sequence SEQ ID NO: 49.

In one aspect, the disclosure relates to an antibody or a functional fragment thereof, comprising a heavy chain CDR1 selected from the amino acid sequence SEQ ID NO: 52, a heavy chain CDR2 selected from the amino acid sequence SEQ ID NO: 53, and a heavy chain CDR3 selected from the amino acid sequence SEQ ID NO: 54; and/or a light chain CDR1 selected from the amino acid sequence SEQ ID NO: 57, a light chain CDR2 selected from the amino acid sequence SEQ ID NO: 58, and a light chain CDR3 selected from the amino acid sequence SEQ ID NO: 59.

In one aspect, the disclosure relates to an antibody or a functional fragment thereof, comprising a heavy chain CDR1 selected from the amino acid sequence SEQ ID NO: 62, a heavy chain CDR2 selected from the amino acid sequence SEQ ID NO: 63, and a heavy chain CDR3 selected from the amino acid sequence SEQ ID NO: 64; and/or a light chain CDR1 selected from the amino acid sequence SEQ ID NO: 67, a light chain CDR2 selected from the amino acid sequence SEQ ID NO: 68, and a light chain CDR3 selected from the amino acid sequence SEQ ID NO: 69.

In one aspect, the disclosure relates to an antibody or a functional fragment thereof, comprising a heavy chain CDR1 selected from the amino acid sequence SEQ ID NO: 72, a heavy chain CDR2 selected from the amino acid sequence SEQ ID NO: 73, and a heavy chain CDR3 selected from the amino acid sequence SEQ ID NO: 74; and/or a light chain CDR1 selected from the amino acid sequence SEQ ID NO: 77, a light chain CDR2 selected from the amino acid sequence SEQ ID NO: 78, and a light chain CDR3 selected from the amino acid sequence SEQ ID NO: 79.

In one aspect, the disclosure relates to an antibody or a functional fragment thereof, comprising a heavy chain CDR1 selected from the amino acid sequence SEQ ID NO: 82, a heavy chain CDR2 selected from the amino acid sequence SEQ ID NO: 83, and a heavy chain CDR3 selected from the amino acid sequence SEQ ID NO: 84; and/or a light chain CDR1 selected from the amino acid sequence SEQ ID NO: 87, a light chain CDR2 selected from the amino acid sequence SEQ ID NO: 88, and a light chain CDR3 selected from the amino acid sequence SEQ ID NO: 89.

In one aspect, the disclosure relates to an antibody or a functional fragment thereof, comprising a heavy chain CDR1 selected from the amino acid sequence SEQ ID NO: 92, a heavy chain CDR2 selected from the amino acid sequence SEQ ID NO: 93, and a heavy chain CDR3 selected from the amino acid sequence SEQ ID NO: 94; and/or a light chain CDR1 selected from the amino acid sequence SEQ ID NO: 97, a light chain CDR2 selected from the amino acid sequence SEQ ID NO: 98, and a light chain CDR3 selected from the amino acid sequence SEQ ID NO: 99.

In one aspect, the disclosure relates to an antibody or a functional fragment thereof, comprising a heavy chain CDR1 selected from the amino acid sequence SEQ ID NO: 102, a heavy chain CDR2 selected from the amino acid sequence SEQ ID NO: 103, and a heavy chain CDR3 selected from the amino acid sequence SEQ ID NO: 104; and/or a light chain CDR1 selected from the amino acid sequence SEQ ID NO: 157, a light chain CDR2 selected from the amino acid sequence SEQ ID NO: 158, and a light chain CDR3 selected from the amino acid sequence SEQ ID NO: 159.

In one aspect, the disclosure relates to an antibody or a functional fragment thereof, comprising a heavy chain variable region selected from the amino acid sequence SEQ ID NO: 1 or any variant thereof, and/or a light chain variable region selected from the amino acid sequence SEQ ID NO: 6 or any variant thereof.

In one aspect, the disclosure relates to an antibody or a functional fragment thereof, comprising a heavy chain variable region selected from the amino acid sequence SEQ ID NO: 11 or any variant thereof, and/or a light chain variable region selected from the amino acid sequence SEQ ID NO: 16 or any variant thereof.

In one aspect, the disclosure relates to an antibody or a functional fragment thereof, comprising a heavy chain variable region selected from the amino acid sequence SEQ ID NO: 21 or any variant thereof, and/or a light chain variable region selected from the amino acid sequence SEQ ID NO: 26 or any variant thereof.

In one aspect, the disclosure relates to an antibody or a functional fragment thereof, comprising a heavy chain variable region selected from the amino acid sequence SEQ ID NO: 31 or any variant thereof, and/or a light chain variable region selected from the amino acid sequence SEQ ID NO: 36 or any variant thereof.

In one aspect, the disclosure relates to an antibody or a functional fragment thereof, comprising a heavy chain variable region selected from the amino acid sequence SEQ ID NO: 41 or any variant thereof, and/or a light chain variable region selected from the amino acid sequence SEQ ID NO: 46 or any variant thereof.

In one aspect, the disclosure relates to an antibody or a functional fragment thereof, comprising a heavy chain variable region selected from the amino acid sequence SEQ ID NO: 51 or any variant thereof, and/or a light chain variable region selected from the amino acid sequence SEQ ID NO: 56 or any variant thereof.

In one aspect, the disclosure relates to an antibody or a functional fragment thereof, comprising a heavy chain variable region selected from the amino acid sequence SEQ ID NO: 61 or any variant thereof, and/or a light chain variable region selected from the amino acid sequence SEQ ID NO: 66 or any variant thereof.

In one aspect, the disclosure relates to an antibody or a functional fragment thereof, comprising a heavy chain variable region selected from the amino acid sequence SEQ ID NO: 71 or any variant thereof, and/or a light chain variable region selected from the amino acid sequence SEQ ID NO: 76 or any variant thereof.

In one aspect, the disclosure relates to an antibody or a functional fragment thereof, comprising a heavy chain variable region selected from the amino acid sequence SEQ ID NO: 81 or any variant thereof, and/or a light chain variable region selected from the amino acid sequence SEQ ID NO: 86 or any variant thereof.

In one aspect, the disclosure relates to an antibody or a functional fragment thereof, comprising a heavy chain variable region selected from the amino acid sequence SEQ ID NO: 91 or any variant thereof, and/or a light chain variable region selected from the amino acid sequence SEQ ID NO: 96 or any variant thereof.

In one aspect, the disclosure relates to an antibody or a functional fragment thereof, comprising a heavy chain variable region selected from the amino acid sequence SEQ ID NO: 101 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 106 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 116 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 121 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 126 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 131 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 136 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 141 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 146 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 151 or any variant thereof, and/or a light chain variable region selected from the amino acid sequence SEQ ID NO: 156 or any variant thereof.

In one aspect, the disclosure relates to an antibody or a functional fragment thereof, comprising a heavy chain variable region selected from the amino acid sequence SEQ ID NO: 101 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 106 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 116 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 121 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 126 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 131 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 136 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 141 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 146 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 151 or any variant thereof, and/or a light chain variable region selected from the amino acid sequence SEQ ID NO: 161 or any variant thereof.

In one aspect, the disclosure relates to an antibody or a functional fragment thereof, comprising a heavy chain variable region selected from the amino acid sequence SEQ ID NO: 101 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 106 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 116 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 121 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 126 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 131 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 136 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 141 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 146 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 151 or any variant thereof, and/or a light chain variable region selected from the amino acid sequence SEQ ID NO: 166 or any variant thereof.

In one aspect, the disclosure relates to an antibody or a functional fragment thereof, comprising a heavy chain variable region selected from the amino acid sequence SEQ ID NO: 101 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 106 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 116 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 121 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 126 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 131 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 136 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 141 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 146 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 151 or any variant thereof, and/or a light chain variable region selected from the amino acid sequence SEQ ID NO: 171 or any variant thereof.

In one aspect, the disclosure relates to an antibody or a functional fragment thereof, comprising a heavy chain variable region selected from the amino acid sequence SEQ ID NO: 101 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 106 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 111 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 116 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 121 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 126 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 131 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 136 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 141 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 146 or any variant thereof, and/or a light chain variable region selected from the amino acid sequence SEQ ID NO: 176 or any variant thereof.

In one aspect, the disclosure relates to an antibody or a functional fragment thereof, comprising a heavy chain variable region selected from the amino acid sequence SEQ ID NO: 151 or any variant thereof, and/or a light chain variable region selected from the amino acid sequence SEQ ID NO: 176 or any variant thereof.

In one aspect, the disclosure relates to an isolated nucleic acid sequence encoding the antibody or the functional fragment or variant thereof as disclosed herein, a vector construct comprising a nucleotide sequence encoding the antibody or an CD47 binding portion of the functional fragment of the antibody of the present invention, a host cell containing the vector and a recombinant technology for producing polypeptides.

In one aspect, the disclosure relates to an isolated nucleic acid sequence encoding the antibody or the functional fragment or variant thereof as disclosed herein, selected from the nucleic acid sequences SEQ ID NO: 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180.

In one aspect, the disclosure further includes kits, e.g., the kits comprises the antibodies and fragments, homologs, and derivatives thereof, etc. of the disclosure, such as labeled or cytotoxic conjugates, and instructions for use of the antibody, conjugates that kills certain types of cells, etc. The instructions may comprise guidance for in vitro, in vivo, or ex vivo use of the antibodies and the conjugates, etc. The antibody may be in a liquid form or in a solid form, typically in a lyophilized form. The kit may contain other suitable agents such as buffers, reconstitution solutions, and other essential ingredients for the intended use. The packaged combination with predetermined amounts of agents and instructions for use are contemplated, wherein the use is, for example, for therapeutic use or for performing diagnostic assays. Where the antibody is labeled, for example, labeled with an enzyme, the kit may comprise a substrate and a cofactor required for the enzyme (e.g., a substrate precursor which provides a detectable chromophore or fluorophore). In addition, other additives such as stabilizers and buffers (e.g., blocking buffers or lysis buffers) may also be comprised. The relative amounts of the various agents can be varied to provide a concentrate of the agent solution, which provides user flexibility, space savings, agent savings, etc. These agents may also be provided in a dry powder form, typically in a lyophilized form, including excipients which, when dissolved, provide a agent solution with an appropriate concentration.

The antibodies of the present invention are useful in the treatment of mammals. In one embodiment, for example, an antibody of interest or an equivalent is administered to a non-human mammal for the purpose of obtaining preclinical data. Exemplary non-human mammals to be treated include non-human primates, dogs, cats, rodents, and other mammals, on which preclinical studies are performed. Such mammals may be used to establish animal models for a disease to be treated with the antibody or may be used to study toxicity of the antibody of interest. In each of these embodiments, dose escalation studies may be performed on the mammal.

The antibody, whether or not with a second component (such as a therapeutic agent component conjugated thereto), can be used as a therapeutic agent, either alone or in combination with a cytotoxic factor. The present invention relates to antibody-based therapies which comprise administering the antibodies of the present invention to an animal, mammal or human to treat an CD47 mediated disease, disorder or condition.

The term "treating/treatment/treat" as used in the present invention refers to therapeutic treatment and prophylactic or preventive measures. It refers to preventing, curing, reversing, attenuating, ameliorating, minimizing, inhibiting or stopping the harmful effects of the disease state, disease progression, disease-causing factors (e.g., bacteria or viruses) or other abnormal conditions.

Accordingly, the present invention also encompasses multivalent antibodies, including bispecific anti-CD47 antibodies having attached effector molecules, atoms or other substances with diagnostic or therapeutic functions. For example, an antibody may have a radiodiagnostic tag or a radioactive cytotoxic atom or a metal or cytotoxic substance such as a ricin chain, which are attached to the antibody for in vivo diagnosis or treatment of cancer.

Furthermore, the antibodies of the present invention may also be used in immunoassays, purification methods, and other methods in which immunoglobulins or fragments thereof are used. Such uses are well known in the art.

Accordingly, the present invention also provides compositions comprising the anti-CD47 antibody or a fragment thereof of the present invention, wherein the antibody is conveniently combined with pharmaceutically acceptable carriers, diluents or excipients, which is a common means in the art.

The term "pharmaceutical composition" as used herein refers to formulations of various preparations. Formulations containing therapeutically effective amounts of multivalent antibodies are sterile liquid solutions, liquid suspensions or lyophilized forms, and optionally contain stabilizers or excipients.

As used herein, the term "disorder" refers to any condition that would benefit from treatment with the antibody of the present invention. This includes chronic and acute disorders or diseases including those pathological conditions that predispose a mammal, especially a human to the disorder. Examples of non-limiting disorders to be treated herein include cancer, inflammation, autoimmune diseases, infections, cardiovascular diseases, respiratory diseases, neurological diseases, and metabolic diseases.

As used herein, the term "cancer" refers to or describes the physiological condition of a mammal, particularly a human, and is typically characterized by examples of unregulated growth of cancer cells including, but not limited to, carcinoma, lymphoma, blastoma, sarcoma, and leukemia.

The antibodies of the present invention may be used as compositions for administration alone or may be used in combination with other active agents.

A nucleic acid encoding the antibody or functional fragment thereof of any of the preceding aspects.

A vector comprising the nucleic acid of any of the preceding aspects.

A cell comprising the vector of any of the preceding aspects.

A pharmaceutical composition comprising the antibody or functional fragment thereof, or the nucleic acid encoding same of any of the preceding aspects, and a pharmaceutically acceptable carrier.

A method for treating cancers, comprising the step of administering to the mammal a therapeutically effective amount of the antibody or functional fragment thereof, or the nucleic acid encoding same of any of the preceding aspects.

A method for treating diseases associated with abnormal production of CD47 in a mammal, comprising the step of administering to the mammal a therapeutically effective amount of the antibody or functional fragment thereof, or the nucleic acid encoding same of any of the preceding aspects.

It will be appreciated that therapeutics in accordance with the described embodiments will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate for use in treatments and therapies in accordance with the present disclosure, provided that the active ingredient in the formulation is not inactivated by the formulation and the formulation is physiologically compatible and tolerable with the route of administration.

In one embodiment, the described antibodies may be used as therapeutic agents. Such agents will generally be employed to treat, alleviate, and/or prevent a disease or pathology associated with aberrant CD47 expression, activity and/or signaling in a subject. A therapeutic regimen is carried out by identifying a subject, e.g., a human patient suffering from (or at risk of developing) a disease or disorder associated with aberrant CD47 expression, activity and/or signaling, e.g., a cancer or other neoplastic disorder, using standard methods. An antibody preparation, preferably one having high specificity and high affinity for its target antigen, is administered to the subject and will generally have an effect due to its binding with the target. Administration of the antibody may abrogate or inhibit or interfere with the expression, activity and/or signaling function of the target (e.g., CD47). Administration of the antibody may abrogate or inhibit or interfere with the binding of the target (e.g., CD47) with an endogenous ligand (e.g., SIRP alpha) to which it naturally binds. For example, the antibody binds to the target and modulates, blocks, inhibits, reduces, antagonizes, neutralizes, or otherwise interferes with CD47 expression, activity and/or signaling. In some embodiments an antibody having heavy and light chain CDRs with the amino acid sequences described in Table 2 may be administered to a subject in order to treat a disease or disorder associated with aberrant CD47 expression. In one embodiment the disease or disorder associated with aberrant CD47 expression may be cancer.

As a non-limiting example, diseases or disorders associated with abnormal CD47 expression, activity, and/or signaling include hematological cancers and/or solid tumors. Hematological cancers include, for example, leukemia, lymphoma and myeloma. As a non-limiting example, certain types of leukemia include acute lymphocytic leukemia (ALL); acute myeloid leukemia (AML); chronic lymphocytic leukemia (CLL); chronic myelogenous leukemia (CML); myeloproliferative Disorder/neoplasm (MPDS); and myelodysplastic syndrome. As non-limiting examples, certain types of lymphoma include Hodgkin's lymphoma, low-grade and aggressive non-Hodgkin's lymphoma, Burkitt's lymphoma, and follicular lymphoma (small cell and Large cells). As a non-limiting example, certain types of myeloma include multiple myeloma (MM), giant cell myeloma, heavy chain myeloma, and light chain or Bence-Jones myeloma. Solid tumors include, for example, breast tumors, ovarian tumors, lung tumors, pancreatic tumors, prostate tumors, melanomas, colorectal tumors, lung tumors, head and neck tumors, bladder tumors, esophageal tumors, liver tumors, and kidney tumors.

Symptoms associated with cancer and other neoplastic disorders include, for example, inflammation, fever, general malaise, fever, pain, often localized to the inflamed area, loss of appetite, weight loss, edema, headache, fatigue, rash, anemia, muscle weakness, muscle fatigue, and abdomen Symptoms such as abdominal pain, diarrhea or constipation.

Therapeutically effective amounts of the antibodies described herein generally relate to amounts necessary to achieve therapeutic purposes. As indicated above, that may be binding interaction between the antibody and its target antigen, hindering the function of the target under certain situations. Additionally, the amount administered depends on the binding affinity of the antibody for its specific antigen, and also depends on the rate of clearance of the administered antibodies from the body. As a non-limiting example, a common range of therapeutically effective doses of the antibodies or antibody fragments described herein, may be from about 0.1 mg/kg body weight to about 100 mg/kg body weight. In one embodiment, a therapeutically effective dosage of the antibodies described herein is from about 0.1 mg/kg body weight to about 0.3 mg/kg body weight. In one embodiment, a therapeutically effective dosage of the antibodies described herein is from about 0.4 mg/kg body weight to about 0.6 mg/kg body weight. In one embodiment, a therapeutically effective dosage of the antibodies described herein is from about 0.7 mg/kg body weight to about 0.9 mg/kg body weight. In one embodiment, a therapeutically effective dosage of the antibodies described herein is from about 1.0 mg/kg body weight to about 2.0 mg/kg body weight. In one embodiment, a therapeutically effective dosage of the antibodies described herein is from about 2.0 mg/kg body weight to about 3.0 mg/kg body weight. In one embodiment, a therapeutically effective dosage of the antibodies described herein is from about 3.0 mg/kg body weight to about 4.0 mg/kg body weight. In one embodiment, a therapeutically effective dosage of the antibodies described herein is from about 4.0 mg/kg body weight to about 5.0 mg/kg body weight. In one embodiment, a therapeutically effective dosage of the antibodies described herein is from about 5.0 mg/kg body weight to about 6.0 mg/kg body weight. In one embodiment, a therapeutically effective dosage of the antibodies described herein is from about 6.0 mg/kg body weight to about 7.0 mg/kg body weight. In one embodiment, a therapeutically effective dosage of the antibodies described herein is from about 7.0 mg/kg body weight to about 8.0 mg/kg body weight. In one embodiment, a therapeutically effective dosage of the antibodies described herein is from about 8.0 mg/kg body weight to about 9.0 mg/kg body weight. In one embodiment, a therapeutically effective dosage of the antibodies described herein is from about 9.0 mg/kg body weight to about 10.0 mg/kg body weight. In one embodiment, a therapeutically effective dosage of the antibodies described herein is from about 10.0 mg/kg body weight to about 15.0 mg/kg body weight. In one embodiment, a therapeutically effective dosage of the antibodies described herein is from about 15.0 mg/kg body weight to about 20.0 mg/kg body weight. Common dosing frequencies may range, for example, from once a day to twice daily to once every other day to once a week.

The effectiveness of the treatment can be determined in conjunction with any known method for diagnosing or treating a specific inflammatory-related disorder. The reduction of one or more symptoms of an inflammatory-related disorder can indicate that the antibody confers clinical benefit.

In another embodiment, antibodies directed against CD47 may be used in methods known within the art relating to the localization and/or quantitation of CD47 (e.g., for use in measuring levels of CD47 and/or both CD47 and SIRP alpha within appropriate physiological samples, for use in diagnostic methods, for use in imaging the protein, and the like). In a given embodiment, antibodies specific to CD47, or derivative, fragment, analog or homolog thereof, that contain the antibody derived antigen binding domain, are utilized as pharmacologically active compounds (referred to hereinafter as "therapeutics").

In another embodiment, an antibody specific for CD47 can be used to isolate a CD47 polypeptide, by standard techniques, such as immunoaffinity, chromatography or immunoprecipitation. Antibodies directed against the CD47 protein (or a fragment thereof) can be used to detect the protein in a biological sample. In some embodiments CD47 may be detected in a biological sample as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive materials include $^{125}$I $^{131}$I, $^{35}$S, or $^{3}$H.

In yet another embodiment, an antibody according to this disclosure can be used as an agent for detecting the presence of CD47 and/or both CD47 and SIRP alpha protein (or a protein fragment thereof) in a sample. In some embodiments, the antibody contains a detectable label. Antibodies are polyclonal, or more preferably, monoclonal. An intact antibody, or a fragment thereof (e.g., Fab, scFv, or F(ab')2) is used. The term "labeled", with regard to an antibody, is intended to encompass direct labeling of the antibody by coupling (i.e., physically linking) a detectable substance to the antibody, as well as indirect labeling of the antibody by reactivity with another reagent that is directly labeled. Examples of indirect labeling include detection of a primary antibody using a fluorescently-labeled secondary antibody and end-labeling of an antibody with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of a described embodiment can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The antibodies described herein and derivatives, fragments, analogs and homologs thereof, can be incorporated into pharmaceutical compositions suitable for administration. Principles and considerations involved in preparing such compositions, as well as guidance in the choice of components are well known in the art, for example, see Remington's Pharmaceutical Sciences: The Science And Practice Of Pharmacy 19th ed. (Alfonso R. Gennaro, et al, editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where antibody fragments are used, the smallest inhibitory fragment that specifically binds to the binding domain of the target protein may be preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al, Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, etc., which are compatible with pharmaceutical administration. Suitable carriers are described in the most recent edition of Remington's Pharmaceutical Sciences, a standard reference text in the field, which is incorporated herein by reference. Preferred examples of such carriers or diluents include, but not limited to, water, saline, Ringer's solutions, dextrose solution, and 5% human serum albumin. Liposomes and non-aqueous carriers such as fixed oils may also be used. The use of such media and agents with pharmaceutically active substances is well known in the art. Except insofar as any conventional media or agent is incompatible with the antibody, use thereof in the compositions is contemplated.

The formulations to be used for in vivo administration must be sterile. This is readily accomplished by filtration through sterile filtration membranes.

The pharmaceutical compositions of the embodiments are formulated to be compatible with their intended route of administration. Examples of routes of administration include parenteral, such as intravenous, intradermal, subcutaneous, oral (e.g., inhalation), transdermal (i.e., topical), transmucosal, and rectal administration. Solutions or suspensions used for parenteral, intradermal or subcutaneous administration may include the following components: sterile diluents for injection such as water, saline solution, fixed oil, polyethylene glycols, glycerol, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates and phosphates; and agents for the adjustment of osmotic pressure such as sodium chloride or dextrose. The pH can be adjusted with an acid or a base such as hydrochloric acid or sodium hydroxide. The parenteral formulation can be enclosed in ampoules, disposable syringes or multiple dose vials made of glass or plastic.

Pharmaceutical compositions suitable for injectable use include sterile aqueous solutions (water soluble herein) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It should be stable under the conditions of manufacture and storage and must be preserved against the contaminating action of microorganisms such as bacteria and fungi. The carrier may be a solvent or dispersion medium containing, for example, water, ethanol, polyol (e.g., glycerol, propylene glycol, liquid polyethylene glycol, etc.), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, etc. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the antibody or antibodies in the required amount in an appropriate solvent with one or a combination of ingredients enumerated above, as required, followed by filtered sterilization. Generally, dispersions are prepared by incorporating the antibody or antibodies into a sterile carrier which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a sterile-filtered solution of the above ingredients.

For administration by inhalation, the compound is delivered in the form of an aerosol spray from a pressurized container or dispenser or nebulizer, which contains a suitable propellant such as carbon dioxide.

Systemic administration can also be performed by transmucosal or transdermal means. For transmucosal or transdermal administration, penetrants appropriate for barrier permeation are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, one or more of the antibodies can be formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the antibodies can be prepared with carriers that will protect the antibodies against rapid elimination from the body, such as a sustained release/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to a person skilled in the art.

For example, these active ingredients can be encapsulated in microcapsules prepared, for example, by coacervation techniques or by interfacial polymerization methods, for example hydroxymethylcellulose or gelatin microcapsules and poly(methylmethacrylate) microcapsules, respectively in colloidal drug delivery systems (e.g., liposomes, albumin microspheres, microemulsions, nanoparticles, and nanocapsules) or in macroemulsions.

A sustained release formulation can be prepared. Examples of suitable sustained release formulations include semipermeable matrices of solid hydrophobic polymers containing the antibodies, which matrices are in form of shaped articles, e.g., films, or microcapsules. Examples of sustained release matrices include polyesters, hydrogels (e.g., poly(2-hydroxyethyl-methylpropionate), or poly(vinyl alcohol)), polylactide (U.S. Pat. No. 3,773,919), copolymers of L-glutamic acid and γ ethyl-L-glutamate, non-degradable ethylene-vinyl acetate, degradable lactic acid-glycollic acid copolymers such as LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Liposomal suspensions (including liposomes targeted to infected cells with monoclonal antibodies against viral antigens) can also be used as pharmaceutically acceptable carriers. These can be prepared according to methods known to a person skilled in the art, for example, methods described in U.S. Pat. No. 4,522,811.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of one or more of the antibodies calculated to produce the desired therapeutic effect in association with the required pharmaceutical carriers. The specifications for the dosage unit forms of the embodiments are dictated by and directly dependent on: the unique characteristics of the antibodies and the particular therapeutic effect to be achieved; and the limitations inherent in the art of formulating such antibodies for the treating individuals.

The pharmaceutical composition can be placed in a container, package, or dispenser together with instructions for administration.

The formulation herein may also contain more than one antibody as necessary for the particular indication being treated, preferably those with complementary activities that do not adversely affect each other. Alternatively, or in addition, the composition may comprise an agent that enhances its function, such as a cytotoxic agent, cytokine, chemotherapeutic agent, or growth-inhibitory agent. Such molecules are suitably present in combination in amounts that are effective for the purpose intended.

In one embodiment, one or more of the antibodies can be administered in a combination therapy, i.e., in combination with other agents, such as therapeutic agents (which can be used to treat pathological conditions or disorders, such as various forms of cancer, autoimmune disorders, and inflammatory disorders). The term "in combination with" as used herein refers to administrating agents substantially simultaneously, simultaneously or sequentially. If administered sequentially, the first compound of two compounds is still preferably detected at an effective concentration at the treatment site upon initiation of administration of the second compound.

For example, a combination therapy may comprise one or more antibodies described herein that are co-formulated and/or co-administered with one or more additional therapeutic agents (e.g., one or more cytokine and growth factor inhibitors, immunosuppressants, anti-inflammatory agents, metabolic inhibitors, enzyme inhibitors, and/or cytotoxin or cytostatic agents, as described in more detail below). Such combination therapies may advantageously utilize lower dosages of the administered therapeutic agents, thus avoiding possible toxicities or complications associated with the various monotherapies.

Preferred therapeutic agents for use in combination with the antibodies described herein are those that interfere with different stages of the inflammatory response. In one embodiment, one or more antibodies described herein can be co-formulated and/or co-administered with one or more additional agents such as other cytokines or growth factor antagonists (e.g., soluble receptors, peptide inhibitors, small molecules, ligand fusions); or antibodies or antigen-binding fragments which bind to other targets (e.g., antibodies which bind to other cytokines or growth factors, receptors thereof, or other cell surface molecules); and anti-inflammatory cytokines or agonists thereof.

In other embodiments, the antibodies described herein are used as vaccine adjuvants for autoimmune disorders, inflammatory diseases, etc. Combinations of adjuvants for treating these types of disorders are suitable for use in combination with various antigens, wherein the antigens are derived from the targeted autoantigens, i.e., autoantigens involved in autoimmunity, such as myelin basic protein; inflammatory autoantigens, such as amyloid peptide protein; or transplantation antigens, such as alloantigens. Antigens may include peptides or polypeptides derived from proteins and fragments of any of the following: sugars, proteins, polynucleotides or oligonucleotides, autoantigens, amyloid peptide proteins, transplantation antigens, allergens or other macromolecular components. In some examples, more than one antigen is comprised in an antigenic composition.

For the purpose of clarity and a concise description, features are described herein as part of the same or separate embodiments, however, it will be understood that the scope of the present invention may include some embodiments having combinations of all or some of the features described.

EMBODIMENTS

1. Expression of CD47 and SIRPα Fusion Protein in Eukaryotic Cells

Using the human CD47 cDNA plasmid (Sino Biological, Cat: HG12283-G) as a template, PCR amplifies the N-terminal extracellular region fragment (19-135) of human CD47 molecule, in which Cys33 was mutated to Gly, and the PCR primers were as follows:

```
Upstream primer:
5'CTGAGAGGTGCCAGATGTCAGCTACTATTTAATAAACAAAATCTGTA

GAATTCACGTTTGGTAATGACACTGTCGT 3'

Downstream primer:
5'TCCGCCTCCGCCGCTAGCTGAAACAACACGATA 3'
```

The amplified product was cloned into a house-constructed eukaryotic expression plasmid system (including C-terminal His6 tag for easy purification). After transfecting HEK293.6E cells for 5-7 days, the culture supernatant was collected and purified by Ni affinity column to obtain recombinant the N-terminal extracellular domain protein of human CD47 molecule (hCD47).

Using human SIRPα cDNA plasmid (Sino Biological, Cat: HG11612-M) as a template, and it was cloned into a house-constructed eukaryotic expression plasmid system with mouse IgG2aFc fragment, and HEK293.6E cells were transfected with these plasmids for 5-7 days, the culture supernatant was collected and purified by Protein A affinity column to obtain recombinant human SIRPα-Fc fusion proteins. 1 mg SIRPα-Fc fusion protein was taken out, the concentration was adjusted to 1 mg/ml with PBS; 1 mg EZ-LinkSulfo-NHS-LC-LC-Biotin (Thermofisher, Cat: 21338) reagent was weighed, and quickly dissolved with 150 uL ddH$_2$O; 13.2 uL dissolved Sulfo-NHS-LC-LC-Biotin reagent was added into the protein solution and uniformly mixed upside down; incubated for 2 hours on the ice; after the reaction, the proteins were transferred into 10,000 Dalton (Da) ultrafiltration tube, concentrated and exchanged to PBS; after measuring OD280, r-streptavidin (Puxin Bio, Cat: 1005-01) was used to detect the protein biotinylation efficiency, and then the proteins were stored in aliquots. The results were shown in FIG. 1 and FIG. 2, respectively.

2. Construction of Human CD47 Gene Stably Transfected Cell Lines

A lentiviral vector containing the full-length sequence of human CD47 was constructed, HEK293T cells were co-transfected with the constructed lentivirus and the packaging plasmids for lentivirus packaging according to the instructions of the lentivirus packaging kit (Lenti-Pac HIV Expression Packaging Kit, GeneCopoeia, Cat No. HPK-LvTR-20). After transfecting for 48 hours, the culture medium was collected, centrifuged at 500*g for 10 minutes to remove cell debris, and the culture supernatant containing lentivirus was obtained. After filtration with a 0.45 um PES filter membrane, aliquoted into 1.5 ml EP tubes (200 ul per tube), and 10 ul was taken out to infect 1×10$^6$ CHO cells, and the rest was stored at −80° C. After infection, 10 ug/ml puromycin was added into the culture medium for screening, and the positive clones were subjected to limiting dilution to obtain the hCD47-CHO-1B10 cell lines stably expressing human full-length CD47 molecules. The results were shown in FIG. 3.

3. Hybridoma Preparation

Human recombinant CD47 protein or hCD47-CHO-1B10 cells were used as an antigen and mixed with an equal amount of immune adjuvant (Freund's adjuvant), and each group of 6 female Balb/c mice of 6-8 weeks were immunized. Two weeks after the prime immunization, a boost immunization was performed. After three times immunizations, blood was taken from the orbit to test the serum titer. Before fusion, 1×10$^6$ hCD47-CHO stable transfected cells were injected into the tail vein challenging. Three days later, the mice were sacrificed by neck dissection. The mouse spleen and some peripheral lymph nodes were taken, centrifuged after milling in DMEM medium; after the supernatant was poured, the spleen cell mass was gently dispersed, and 5 ml of red blood cell lysis buffer was added. 40 ml DMEM was added after lysis for 50 s to centrifuge, a spleen cell suspension without red blood cells was obtained. After mixing an appropriate amount of lymph node and the spleen cell suspension with SP2/0, the BTX electrofusion instrument was used for cell fusion. The fusion cells were seeded in a 96-well plate, and cultured in a complete DMEM medium containing HAT under 5% CO$_2$ condition at 37° C. The growth of hybridoma cells was observed in about a week, and the supernatant was taken out for antibody detection when the hybridoma cells grew to more than 60%.

4. Screening of hybridoma supernatants 1 ug/ml hCD47 antigen (hCD47R-ECD chis) was prepared with 0.05M pH9.0 bicarbonate buffer solution, added to a 96-well microtiter plate (Costar, Cat: 9018) at 100 ul per well volume was, incubated overnight at 4° C., washed 3 times with PBS the next day, sealed with 200 ul 2% skimmed milk powder/PBS for 2 hours at room temperature, washed 3 times with PBS, 50 ul hybridoma supernatant was added, washed with PBST and PBS 3 times after incubating for 1 hour at room temperature, secondary antibody (Anti-mouse IgG-Fc-HRP, Jackson ImmunoResearch Cat: 115-035-071) was added and incubated for 1 hour, 50 ul color developing solution (TMB solution, Sigma Cat: T2885) was added after washing 3 times, 50 ul 2M concentrated sulfuric acid solution was added after standing at 37° C. for 5 minutes to terminate the reaction, and immediately putted in the microplate reader to read the OD450 value.

The positive clones supernatant binding to CD47 antibody detected by ELISA was further verified for binding to CD47-positive cells. CCRF-CEM cells (ATCC®CRM-CCL-119™) were taken out and added into a 96-well plate at 5×10$^4$/well, 50 ul hybridoma supernatant was added to each well, incubated at 4° C. for 60 minutes, centrifuged and the supernatant was pipetted, washed with 0.5% BSA/PBS, and then 50 ul secondary antibody solution (anti-mouse IgG-Fc-AF647, Jackson ImmunoResearch Cat: 115-606-071) was added, incubated at 4° C. for 45 minutes, then the excess secondary antibody was washed off with 0.5% BSA/PBS, and finally 60 ul PBS solution containing 1 ug/ml fluorescent dye (propidium iodide, PI, Sigma, Cat: P4170) was used to resuspend the cells and detected on a flow cytometer. The results were shown in FIG. 4.

5. Assay of CD47-SIRPα Blocking

Figure 5:
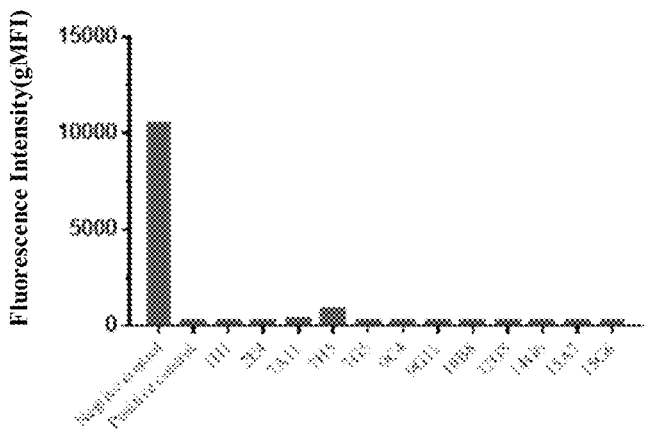
FIG. 5. CD47-SIRPα blocking experiment, that hybridoma positive clones 1H1, 2E4, 7A11, 7G5, 7H5, 9C4, 9G11, 10B8, 12G8, 14G6, 15A7 and 15G6 can effectively inhibit the binding of SIRPα and CD47 after binding to the surface of CD47 positive cells.

CCRF-CEM cells are added to a 96-well plate at 5×10⁴/well, 50 ul hybridoma supernatant to each well was added, incubated at 4° C. for 30 mins, 50 ul 1 ug/ml biotinylated SIRPα-Fc fusion proteins was added, incubated at 4° C. for 30 mins, washed with 0.5% BSA/PBS, 50 ul secondary antibody solution (SA-PE, Jackson ImmunoResearch Cat: 016-110-084) was added, and finally 60 ul PBS solution containing 1 ug/ml fluorescent dye (propidium iodide, PI, Sigma, Cat: P4170) was used to resuspend the cells, and detected on a flow cytometer. The results are shown in FIG. 5. Hybridoma positive clones 1H1, 2E4, 7A11, 7G5, 7H5, 9C4, 9G11, 10B8, 12G8, 14G6, 15A7 and 15G6 can effectively prevent the binding of SIRPα to CD47 after binding to the surface of CD47 positive cells.

6. Cloning of Candidate Antibody Genes

According to the results of the preliminary screening, we extracted RNA from hybridoma cells and reverse transcribed it into cDNA. The cDNA template was used for PCR amplification. After sequencing, the variable region sequences of the heavy chain and light chain of the candidate positive clones were obtained as:

Clone 2E4-C7:

```
Heavy chain
                                        (SEQ ID No: 1-4)
<-------------FR1-------------> CDR1<----FR2----->
QIQLQQSGPEVVKPGASVKISCKASGYTFTDDYINWVKQKPGQGLEWIG CDR2          <------------FR3---------------->
WIYPGSGNAKYNEKFKGKATLIVDTSSTTAYMQLSSLTSEDTAVYFCSR

CDR3    <---FR4--->
RREDSFDYWGQGTTLTVSS

Nucleic acid sequences
                                          (SEQ ID NO: 5)
CAGATCCAGCTGCAGCAGTCTGGACCTGAGGTGGTGAAGCCTGGGCTTC

AGTGAAGATATCCTGCAAGGCTTCTGGCTACACCTTCACTGACGACTATA

TAAACTGGGTGAAGCAGAAGCCTGGACAGGGACTTGAGTGGATTGGATGG

ATTTATCCTGGAAGCGGTAATCCTAAGTACAATGAGAAGTTCAAGGGCAA

GGCCACATTGATTGTAGACACATCCTCCACCACAGCCTACATGCAGCTCA

GCAGCCTGACATCTGAGGACACTGCTGTCTATTTCTGTTCAAGAAGGAGG

GAGGATTCCTTTGACTACTGGGGCCAAGGCACCACTCTCACAGTCTCCTC

A

Light chain
                                        (SEQ ID NO: 6-9)
<----------FR1--------->       CDR1      <------FR2
DFVMSQSPSSLAVSVGEKVTMSCKSSQSLLYSSNQKNYLAWYQQKPGQS ----> CDR2   <--------FR3--------------------->
PKLLIYWASTRESGVPDRFTGSGSGTDFTLTISSVKPEDLAVYYC

CDR3    <---FR4--->
QQFYRYPLTFGAGTKLELK
```

```
Nucleic acid sequences
                                        (SEQ ID NO: 10)
GACTTTGTGATGTCACAGTCTCCATCCTCCCTAGCTGTGTCAGTCGGAGA

GAAAGTTACTATGAGCTGCAAGTCCAGTCAGAGCCTTTTATATAGTAGCA

ATCAAAAGAATTACTTGGCCTGGTACCAGCAGAAACCAGGGCAGTCTCCT

AAACTGCTGATTTACTGGGCATCCACTAGGGAATCTGGGGTCCCTGATCG

CTTCACAGGCAGTGGATCTGGGACAGATTTCACTCTCACCATCAGCAGTG

TGAAGCCTGAAGACCTGGCAGTTTATTACTGTCAGCAATTTTATAGGTAC

CCGCTCACGTTCGGTGCTGGGACCAAGCTGGAGCTGAAA
```

Clone 7A11-C2

```
Heavy chain
                                        (SEQ ID NO: 11-14)
<-------------FR1-------------> CDR1<----FR2----->
QIQLQQSGPELVKPGASVKISCKASGYTFTDYYLHWVKQRPGQGLEWIG CDR2          <-----------FR3---------------->
WIYPGSGNTKYNEKFKGKATLTVDTSSSTAYMQLSSLTSEDTAVYFCAR

CDR3   <----FR4--->
RREDSFDYWGQGTTLTVSS

Nucleic acid sequences
                                       (SEQ ID NO: 15)
CAGATCCAGCTGCAGCAGTCTGGACCTGAGCTGGTGAAGCCTGGGGCTTC

AGTGAAGATATCCTGCAAGGCTTCTGGCTACACCTTCACTGACTACTATC

TACACTGGGTGAAGCAGAGGCCTGGACAGGGACTTGAGTGGATTGGATGG

ATTTATCCTGGAAGCGGTAATACTAAGTACAATGAGAAGTTCAAGGGCAA

GGCCACATTGACTGTAGACACATCCTCCAGCACAGCCTACATGCAGCTCA

GCAGCCTGACATCTGAGGACACTGCTGTCTATTTCTGTGCAAGAAGGAGG

GAGGATTCCTTTGACTACTGGGGCCAAGGCACCACTCTCACAGTCTCCTC
A

Light chain
                                       (SEQ ID NO: 16-19)
<----------FR1-------->       CDR1      <------FR2
DIVMSQSPSSLAVSVGEKVTMSCKSSQSLLYSSNQKNYLTWYQQKPGQS ----> CDR2   <------FR3---------------------->
PKLLIYWASTRESGVPDRFTGSGSGTDFTLTISSVKAEDLAVYYC

CDR3   <---FR4--->
QQYYSYPLTFGAGTKLELK

Nucleic acid sequences
                                        (SEQ ID NO: 20)
GACATTGTGATGTCACAGTCTCCATCCTCCCTAGCTGTGTCAGTTGGAGA

GAAGGTTACTATGAGCTGCAAGTCCAGTCAGAGCCTTTTATATAGTAGCA

ATCAAAAGAACTACTTGACCTGGTACCAGCAGAAACCAGGGCAGTCTCCT

AAACTGCTGATTTACTGGGCATCCACTAGGGAATCTGGGGTCCCTGATCG
```

```
CTTCACAGGCAGTGGATCTGGGACAGATTTCACTCTCACCATCAGCAGTG

TGAAGGCTGAAGACCTGGCAGTTTATTACTGTCAGCAATATTATAGCTAT

CCGCTCACGTTCGGTGCTGGGACCAAGCTGGAGCTGAAA
```

Cloning 7G5-D10

```
Heavy chain
                                       (SEQ ID NO: 21-24)
<-------------FR1------------> CDR1<----FR2----->
QVQLQQPGPELVKPGTSVKISCKASGYTFTDDYINWVKQKPGQGLEWIG CDR2            <------------FR3---------------->
WIYPGSGNTKYNEKFKGKATLTVDTSSSTAYMQLSSLTSEDTAVYFCAR

CDR3     <---FR4--->
RREDSFDYWGQGTTLTVSS

Nucleic acid sequences
                                            (SEQ ID NO: 25)
CAGGTCCAACTGCAGCAGCCTGGACCTGAGCTGGTGAAGCCTGGGACTTC

AGTGAAGATATCCTGCAAGGCTTCTGGCTACACCTTCACTGACTACTATA

TAAACTGGGTGAAGCAGAAGCCTGGACAGGGACTTGAGTGGATTGGATGG

ATTTATCCTGGAAGCGGTAATACTAAGTACAATGAGAAGTTCAAGGGCAA

GGCCACATTGACTGTAGACACATCCTCCAGCACAGCCTACATGCAGCTCA

GCAGCCTGACATCTGAGGACACTGCTGTCTATTTCTGTGCAAGAAGGAGG

GAGGATTCCTTTGACTACTGGGGCCAAGGCACCACTCTCACAGTCTCCTC

A

Light chain
                                       (SEQ ID NO: 26-29)
<----------FR1--------->        CDR1         <------FR2
DIVMSQSPSSLAVSVGEKVAMSCKSSQSLLYSSNQKNYLTWYQQKPGQS ----> CDR2   <------FR3---------------------->
PKLLIYWASTRESGVPDRFTGSGSGTDFTLTISSVKAEDLAVYYC

CDR3    <---FR4--->
QQYYSYPLTFGAGTKLELK

Nucleic acid sequences
                                            (SEQ ID NO: 30)
GACATTGTGATGTCACAGTCTCCATCCTCCCTAGCTGTGTCAGTGGAGA

GAAGGTTGCTATGAGCTGCAAGTCCAGTCAGAGCCTTTTATATAGTAGCA

ATCAAAAGAACTACTTGACCTGGTACCAGCAGAAACCAGGGCAGTCTCCT

AAACTGCTGATTTACTGGGCTTCCACTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAACAATATTATAGCTAT

CCGCTCACGTTCGGTGCTGGGACCAAGCTGGAGCTGAAA
```

Cloning 7115-B12

```
Heavy chain
                                       SEQ ID NO: 31-34
<-------------FR1------------> CDR1<----FR2----->
QVQLQQPGAELVKPGASVKMSCKASGYTFTNYNFHWVKQTPGQGLEWIG CDR2            <-----------FR3---------------->
TFYPVNGDTSYNQKFDGKATVTADKSSSTAYMQLSSLTSEDSAVYYCA

CDR3   <---FR4---->
RGGTRAMDYWGQGTSVTVSS

Nucleic acid sequences
                                            (SEQ ID NO: 35)
CAGGTCCAACTGCAGCAGCCTGGGGCTGAGCTGGTGAAGCCTGGGGCCTC

AGTGAAGATGTCCTGCAAGGCTTCTGGCTACACATTTACCAATTACAATT

TTCACTGGGTAAAGCAGACACCTGGACAGGGCCTGGAATGGATTGGAACA

TTTTATCCAGTAAATGGTGATACTTCCTACAATCAGAAGTTCGATGGCAA

GGCCACAGTGACTGCAGACAAATCCTCCAGCACAGCCTACATGCAGCTCA

GCAGCCTGACATCTGAGGACTCTGCGGTCTATTACTGTGCAAGAGGGGGT

ACGAGGGCTATGGACTACTGGGGTCAAGGGACCTCAGTCACCGTCTCCTC

A

Light chain
                                       (SEQ ID NO: 36-39)
<----------FR1--------->        CDR1
DVLMTQTPLSLPVSLGDQASISCRSSQGIVHSNGNTYLA <------FR2-----> CDR2 <------FR3------------------
WYLQKPGQSPKLLIYKVSNRFSGVPDRFSGSGSGTDFTLKISRVEAEDLG

--->CDR3   <---FR4--->
VYYCFQGSHVPYTFGGGTKLEIK

Nucleic acid sequences
                                            (SEQ ID NO: 40)
GATGTTTTGATGACCCAAACTCCACTCTCCCTGCCTGTCAGTCTTGGAGA

TCAAGCCTCCATCTCTTGCAGATCTAGTCAGGGCATTGTACATAGTAATG

GAAACACCTATTTAGCATGGTACCTGCAGAAACCAGGCCAGTCTCCAAAA

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TACACGTTCGGAGGGGGGACCAAGCTGGAAATAAAA
```

Cloning 9G11-D2

```
Heavy chain
                                       (SEQ ID NO:41-44)
<-------------FR1------------> CDR1<----FR2----->
QILLQQSGPDLVKFGASVKISCKASGYTFTDYYIHWVKQKPGQGLEWIG CDR2            <-----------FR3---------------->
WIYPGSGNTKYNEKFKGKATLTVDTSSSTPYMQLSSLTSEDTAVYFCTR

CDR3   <----FR4--->
RREDSFDYWGQGTTLTVSS
```

Nucleic acid sequences
(SEQ ID NO: 45)
CAGATCCTGCTGCAGCAGTCTGGACCTGACCTGGTGAAGCCTGGGCTTC

AGTGAAGATTTCCTGCAAGGCTTCTGGATACACCTTCACTGACTACTATA

TACACTGGGTGAAGCAGAAGCCTGGACAGGGACTTGAGTGGATTGGATGG

ATTTATCCTCCAAGCGGTAATACTAACTACAATGAGAAATTCAAGGGCAA

GGCCACATTGACTSTAGACACATCCTCCAGCACACCCTACATGCAGCTCA

GCAGCCTGACATCTGAGGACACTCCTGTCTATTTCTGTACAAGAAGGAGG

GAGGATTCCTTTGACTACTGGGGCCAAGSCACCACTCTCACAGTCTCCTC

A

Light chain
(SEQ ID NO: 46-49)
<----------FR1-------->      CDR1       <------FR2-
DIVMSQSPSSLAVSVGEKVTMSCKSSQSLLYSSNQKNYLAWYQQKFGQSP ----> CDR2 <------ FR3--------------------->
KLLIYWASTRESGVPDRFTGSGSGTDFTLTISSVKAEDLAVYYC CDR3    <---FR4--->
QQFYSYPLTFGACTRLELK Nucleic acid sequences
(SEQ ID NO: 50)
GACATTGTGATGTCACAGTCTCCATCCTCCCTAGCTGTGTCAGTTGGAGA

GAAGGTTACTATGAGCTGCAAGTCCAGTCAGAGCCTTTTATATAGTAGCA

ATCAAAAGAACTACTTGGCCTGGTACCAGCAGAAACCAGGGCAGTCTCCT

AAACTGCTGATTTACTGGGCATCCACTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATTTTATAGCTAT

CCGCTCACGTTCGGTGCTGGGACCAAGCTGGAGCTGAAA

Clone 10B8-B8

Heavy chain
(SEQ ID NO: 51-54)
<-------------FR1-------------> CDR1<----FR2----->
QIQLQQSGPDLVKPGASVKISCKASGYTFTDYYIHWMKQKPGQGLEWIGW

CDR2           <----------FR3---------------->
IYPGSGNTKYNEKFKGKATLTVDTSSSTPYMQLSSLTSEDTAVYFCAR

CDR3    <----FR4--->
RREDSFDYWGQVTTLTVSS

Nucleic acid sequences
(SEQ ID NO: 55)
CAGATCCAGCTGCAGCAGTCTGGACCTGACCTGGTGAAGCCTGGGCTTC

AGTGAAGATTTCCTGCAAGGCTTCTGGATACACCTTCACTGACTACTATA

TACACTGGATGAAGCAGAAGCCTGGACAGGGACTTGAGTGGATTGGATGG

ATTTATCCTGGAAGCGGTAATACTAAGTACAATGAGAAGTTCAAGGGCAA

GGCCACATTGACTGTAGACACATCCTCCAGCACACCCTACATGCAGCTCA

GCAGCCTGACATCTGAGGACACTGCTGTCTATTTCTGTGCAAGAAGGAGG

GAAGATTCCTTTGACTACTGGGGCCAAGTCACCACTCTCACAGTCTCCTG

A

Light chain
(SEQ ID NO: 56-59)
<----------FR1-------->      CDR1       <------
DIVMSQSPSSLAVSVGEQVTMSCKSSQSLLYSSNQKNYLAWYQQKP FR2----> CDR2  <------ FR3--------------------->
GQSPKLLIYWASTRESGVPDRFTGSGSGTDFTLTISSVRAEDLAVYYC CDR3    <---FR4--->
QQFYSYPLTFGAGTKLELK Nucleic acid sequences
(SEQ ID NO: 60)
GACATTGTGATGTCACAGTCTCCATCCTCCCTAGCTGTGTCAGTTGGAGA

GCAGGTTACTATGAGCTGCAAGTCCAGTCAGAGCCTTTTATATAGTAGCA

ATCAAAAGAACTACTTGGCCTGGTACCAGCAGAAACCAGGGCAGTCTCCT

AAATTGTTGATTTACTGGGCATCCACTAGGGAATCTGGGGTCCCTGATCG

CTTCACAGGCAGTGGATCTGGGACAGATTTCACTCTCACCATCAGCAGTG

TGAGGGCTGAAGACCTGGCAGTTTATTACTGTCAGCAATTTTATAGCTAT

CCGCTCACGTTCGGTGCTGGGACCAAGCTGGAGCTGAAA

Cloning 12G8-A9

Heavy chain
(SEQ ID NO: 61-64)
<-------------FR1-------------> CDR1<----FR2----->
QIQLQQSGPELVKPGASVKISCKASGYIFTDYYIHWVKQRPGQGLEWIG CDR2           <----------FR3------------------>
WIYPGSGNTKYNEKFKGKATLTVDTSSSTAYMQLSSLTSEDTAVYFCAR CDR3    <----FR4--->
RREDSFDYWGHGTTLTVSS Nucleic acid sequences
(SEQ ID NO: 65)
CAGATCCAGCTGCAGCAGTCTGGACCTGAGCTGGTGAAGCCTGGGCTTC

AGTGAAGATATCCTGCAAGGCTTCTGGCTACATCTTCACTGACTACTATA

TACACTGGGTGAAGCAGAGGCCTGGACAGGGACTTGAGTGGATTGGATGG

ATTTATCCTGGAAGCGGTAATACTAAGTACAATGAGAAGTTCAAGGGCAA

GGCCACATTGACTGTAGACACATCCTCCAGCACAGCCTACATGCAGCTCA

GCAGCCTGACATCTGAGGACACTGCTGTCTATTTCTGTGCAAGAAGGAGG

GAAGATTCCTTTGACTACTGGGGCCATGGCACCACTCTCACAGTCTCCTC

A

Light chain
(SEQ ID NO: 66-69)
<----------FR1--------> CDR1 <------
DIVMSQSPSSLAVSVGEKVTMSCKSSQSLLYSSNQKNYLTWYQQKP FR2----> CDR2 <------ FR3--------------------->
GQSPKLLIYWASTRESGVPDRFTGSGSGTDFTLTISSVKAEDLAVYHC

CDR3 <---FR4--->
QQYYSYPLTFGAGTKLELK

Nucleic acid sequences
(SEQ ID NO: 70)
GACATTGTGATGTCACAGTCTCCATCCTCCCTAGCTGTGTCAGTTGGAGA
GAAGGTTACTATGAGCTGCAAGTCCAGTCAGAGCCTTTTATATAGTAGCA
ATCAAAAGAACTACTTGACCTGGTACCAGCAGAAACCAGGGCAGTCTCCT
AAACTGCTGATTTACTGGGCATCCACTAGGGAATCTGGGGRCCCTGATCG
CTTCACAGGCAGTGGATCTGGGACAGATTTCACTCTCACCATCAGCAGTG
TGAAGGCTGAAGACCTGGCAGTTTATCACTGTCAGCAATATTATAGCTAT
CCGCTCACGTTCGGTGCTGGGACCAAGCTGGAGCTGAAA Clone 14G6-C1

Heavy chain
(SEQ ID NO: 71-74)
<-------------FR1-------------> CDR1<----FR2----->
QIQLQQSGPELVKTGASVRISCKASGFTFTDSYINWVKQRPGQGLQWIG CDR2 <----------FR3---------------->
WIYPGSGNTKYNEKFKDKATLTVDTSSSTAYMQLNSLTSEDTAVFFCTR

CDR3 <----FR4--->
RREDSFDYWGQGTTLTVSS

Nucleic acid sequences
(SEQ ID NO: 75)
CAAATCCAGCTACAGCAGTCTGGACCTGAGCTGGTGAAGACTGGGGCTTC
AGTGAGGATATCCTGCAAGGCTTCTGGCTTCACCTTCACTGACTCCTATA
TAAACTGGGTGAAGCAGAGGCCTGGACAGGGACTTCAGTGGATTGGATGG
ATTTATCCTGGAAGCGGTAATACTAAGTACAATGAGAAGTTCAAGGACAA
GGCCACATTGACTGTAGACACATCTTCCAGCACAGCCTACATGCAGCTCA
ACAGCCTGACATCTGAGGACACTGCTGTCTTTTTCTGTACAAGAAGGAGG
GAGGATTCTTTTGACTATTGGGGCCAAGGCACCACTCTCACAGTCTCCTC
A Light chain
(SEQ ID NO: 76-79)
<----------FR1--------> CDR1 <------FR2
DIVMSQSPSSLAVSVGEKVTMSCKSSQSLLYSSNQKNYLTWYQQKPGQS ----> CDR2 <------FR3--------------------->
PKLLIYWASIRESGVPDRFTGSGSGTDFTLTISSVKAEDLAVYYC

CDR3 <---FR4--->
QQYYSYPLTFGAGTKLELK

Nucleic acid sequences
(SEQ ID NO: 80)
GACATTGTGATGTCACAGTCTCCATCCTCCCTAGCTGTGTCAGTTGGAGA
GAAGGTTACTATGAGCTGCAAGTCCAGTCAGAGCCTTTTATATAGTAGCA
ATCAAAAGAACTACTTGACCTGGTACCAGCAGAAACCAGGGCAGTCTCCT
AAACTGCTGATTTACTGGGCATCCATTAGGGAATCTGGGGTCCCTGATCG
CTTCACAGGCAGTGGATCTGGGACAGATTTCACTCTCACCATCAGCAGTG
TGAAGGCTGAAGACCTGGCAGTTTATTACTGTCAGCAATATTATAGCTAT
CCGCTCACGTTCGGTGCTGGGACCAAGCTGGAGCTGAAA Cloning 15G6-E8

Heavy chain
(SEQ ID NO: 81-84)
<-------------FR1-------------> CDR1<----FR2----->
QIQLQQSGPELVKPGASVKISCKASGYTFTDYYIHWVKQKPGQGLEWIG CDR2 <----------FR3---------------->
WIYPGSGNTKYNEKFKGKATLTVDTSSSTVYMQPSSLTSEDIAVYFCAR

CDR3 <----FR4--->
RREDSFDYWGQGTTLTVSS

Nucleic acid sequences
(SEQ ID NO: 85)
CAGATCCAGCTGCAGCAGTCTGGACCTGAGCTGGTGAAGCCTGGGGCTTC
AGTGAAGATATCCTGCAAGGCTTCTGGCTACACCTTCACTGACTACTATA
TACACTGGGTGAAGCAGAAGCCTGGACAGGGACTTGAGTGGATTGGATGG
ATTTATCCTGGAAGCGGTAATACTAAGTACAATGAGAAGTTCAAGGGCAA
GGCCACATTGACTGTAGACACATCCTCCAGCACAGTCTACATGCAGCCCA
GCAGCCTGACATCTGAGGACATTGCTGTCTATTTCTGTGCAAGAAGGAGG
GAGGATTCCTTTGACTACTGGGGCCAAGGCACCACTCTCACAGTCTCCTC
A Light chain
(SEQ ID NO: 86-89)
<----------FR1--------> CDR1 <------FR2
DIVMSQSPSSLTVSVGEKVTMSCKSSQSLLYSSNQKNYLAWYQRKPGQS ----> CDR2 <------FR3--------------------->
PKLLIYWASNRESGVPDRFTGSGSGTDFTLTISSVKAEDLAVYYC

CDR3 <---FR4--->
QQFYRYPLTFGAGTKLELK

Nucleic acid sequences
(SEQ ID NO: 90)
GACATTGTGATGTCACAGTCTCCATCCTCCCTAACTGTGTCAGTTGGAGA
GAAGGTTACTATGAGCTGCAAGTCCAGTCAGAGCCTTTTATATAGTAGCA
ATCADAAGAACTATTTGGCCTGGTACCAGCGGAAGCCAGGGCAGTCTCCT
AAACTCTTGATTTACTGGGCATCCAATAGGGAATCTCGGGTCCCCGATCG
CTTCACAGGCAGTGGATCTGCGACACATTCACGTTCGGTGCTGGGACCAA
GCTGGAGCTGAAA Cloning 15a7-a10

Heavy chain
(SEQ ID NO: 91-94)
```
<-------------FR1------------> CDR1<----FR2----->
QIQLQQSGPDLVKPGASVKISCKASGYTFTDNYIHWVKQKPGQGLEWIG CDR2          <----------FR3---------------->
WIYPGSGNAKYNEKFKGKATLTVDRSSSTPYMQPSSLTSEDTAVYFCTR

CDR3  <----FR4--->
RREDSFDYWGQGTTLTVSS
```

Nucleic acid sequences
(SEQ ID NO: 95)
```
CAGATCCTGCTGCAGCAGTCTGCACCTGACCTGGTGAAGCCTGGGGCTTC
AGTGAAGATTTCCTGCAAGGCTTCGGGATACACCTTCACTGACAACTATA
TACACTGGGTGAAGCAGAAGCCTGGACAGGGACTTGASTGGATTGGATGG
ATTTATCCTGGAAGTGGTAATGCTAAGTACAATGAGAAATTCAAGGGCAA
GGCCACATTGACTGTAGACAGATCCTCCAGCACACCCTACATGCAACTCA
GCAGCCTGACATCTGAGGACACTGCTGTCTATTTCTGTACAAGAAGGAGG
GAGGATTCCTTTGACTACTGGGGCCAAGGCACCACTCTCACAGTCTCCTC
A
```

Light chain
(SEQ ID NO: 96-99)
```
<----------FR1--------->      CDR1      <------FR2
DIVMSQSPSSLAVSVGEKVTMSCKSSQSLLYSSNQKNYLAWYQQKPGQS ----->  CDR2   <------FR3---------------------->
PKLLIYWASTRESGVPDRFTGSGSGTDFTLTISSVKAEDLAVYYC

CDR3  <---FR4--->
QQFYRYPLTFGAGTKLELK
```

Nucleic acid sequences
(SEQ ID NO: 100)
```
GACATTGTGATGTCACAGTCTCCATCCTCCCTAGCTGTGTCAGTTGGAGA
GAAGGTTACTATGAGCTGCAAGTCCAGTCAGAGCCTTTTATATAGTAGCA
ATCAAAAGAACTACTTGGCCTGGTACCAGCAGAAACCAGGGCAGTCTCCT
AAACTGCTGATTTACTGGGCATCCACTAGGGAATCTGGGGTCCCTGATCG
CTTCACAGGCAGTGGATCTGGGACAGATTTCACTCTCACCATCAGCAGTG
TGAAGGCTGAAGACCTGGCAGTTTATTACTGTCAGCAATTTTATAGGTAT
CCGCTCACGTTCGGCGCTGGGACCAAGCTGGAGCTGAAA
```

7. Construction and Expression of Chimeric Antibodies

The heavy chain and light chain variable region sequence fragments were amplified, and inserted into the corresponding plasmid vector expressing the complete antibody heavy and light chain via Gibson Assembly, where the heavy chain variable region was cloned into the vector containing the human heavy chain constant region, so that the complete IgG1 heavy chain can be expressed in mammalian cells. Similarly, the light chain variable region was cloned into a vector containing the human light chain constant region to express the complete IgG kappa light chain in mammalian cells. The plasmids after the correct sequencing were transiently expressed CD47 antibody candidates in the mammalian cell HEK293.6E, and the cell supernatant was collected 5-7 days later, filtered and purified. IgG is purified by Protein A chromatography, washed with 50 mM Tris-HCl pH8.0, 250 mM NaCl, and the bound IgG was eluted with 0.1M Glycine-HCl pH3.0. The proteins were concentrated by ultrafiltration by using a concentration tube (Millipore) and exchanged to PBS solution, and the IgG concentration was measured.

Binding and Blocking of CD47 by Chimeric Antibodies

The recombinantly expressed chimeric antibody was subjected to human CD47 molecular binding and CD47-SIRPα blocking experiments at the antigen and cellular levels by using ELISA and FACS, respectively.

Figure 6:
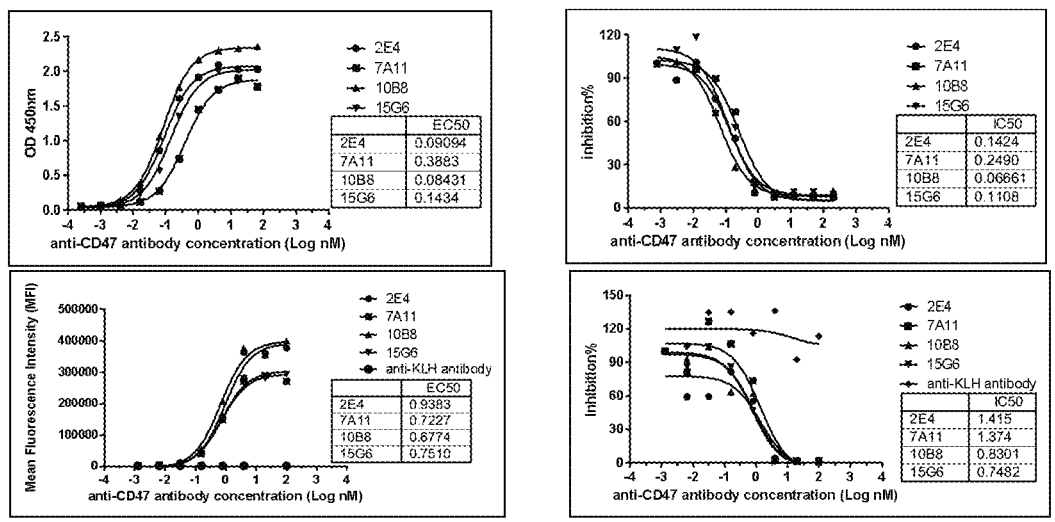

Detection of the Binding of Chimeric Antibody to CD47 with Recombinant CD47 Antigen 1 ug/ml hCD47 antigen was prepared with 0.05M pH9.0 bicarbonate buffer solution, added to 96-well microtiter plate at 100 ul per well volume, incubated overnight at 4° C., washed 3 times with PBS the next day, sealed with 200 ul 2% skimmed milk powder/PBS for 2 hours at room temperature, washed 3 times with PBS, 50 ul antibody diluted in equal proportions was added, washed 3 times with PBST and PBS after incubating for 1 hour at room temperature, secondary antibody anti-mouse IgG-Fc-HRP was added and incubated for 1 hour, 50 ul color developing solution (TMB solution, Sigma, Cat:T2885) was added after washing 3 times. 50 ul 2M concentrated sulfuric acid solution was added after standing at 37° C. for 5 minutes to terminate the reaction, and immediately putted into the microplate reader to read the OD450 value (FIG. 6-1);

Using Recombinant CD47 Antigen to Detect the Inhibitory Effect of Chimeric Antibody on CD47-SIRPα Binding 1 ug/ml recombinant protein hCD47 was coated overnight, washed 3 times with PBS the next day, sealed with 200 ul 2% skimmed milk powder/PBS for 2 hours at room temperature, washed 3 times with PBS, 50 ul of CD47 chimeric antibodies of different concentrations diluted in equal proportions was added. Then 50 ul biotinylated SIRPα-Fc fusion proteins was added, washed 3 times with PBST and PBS respectively after incubating at room temperature for 1 hour, secondary antibody (SA-HRP, Jackson ImmunoResearch Cat: 016-030-084) was added and incubated for 1 hour, 50 ul color developing solution was added after washing 3 times. 50 ul 2M concentrated sulfuric acid solution was added after standing at 37° C. for 5 minutes to terminate the reaction, and immediately putted into the microplate reader to read the OD450 value (FIG. 6-2).

Figure 3:
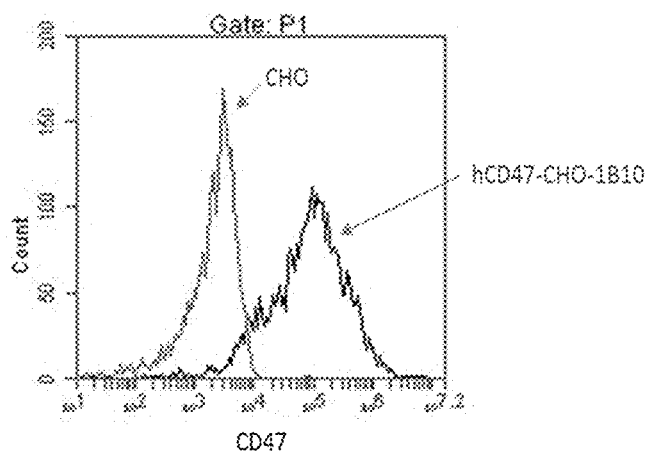
FIG. 3. Human CD47-CHO stably transfected cell lines and untransfected CHO blank cells.
Figure 4:
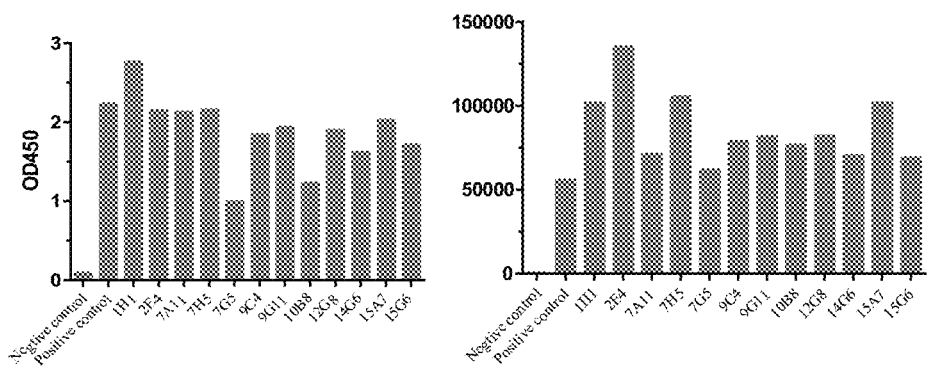
FIG. 4. The above Figure shows the positive hybridoma clones obtained by verification and screening with recombinant human CD47 antigen (left) and CD47 positive cells (right).

Detection of the Biological Activity of Binding the Chimeric Antibody to CD47 at the Cellular Level The hCD47-expressing tumor cells CCRF-CEM were selected, plated at $5 \times 10^4$ cells per well in a 96-well U-shaped plate, 50 ul CD47 chimeric antibodies of different concentrations diluted in equal proportions were added, incubated at 4° C. for 60 minutes, and then the excess primary antibody was washed off with 0.5% BSA/PBS, then 50 ul the secondary antibody solution anti-mouse IgGFc-AF647 was added, incubated at 4° C. for 45 minutes, then the excess secondary antibody was washed off with 0.5% BSA/PBS, and finally the cells were resuspend in 60 ul PBS solution containing 1 ug/ml of the fluorescent dye PI, and immediately detected on the flow cytometer (FIG. 6-3);

Detecting the Inhibitory Effect of Chimeric Antibody on CD47-SIRPα Binding at the Cellular Level The CCRF-CEM was plated at $5 \times 10^4$ cells per well in a 96-well U-shaped plate, 50 ul CD47 antibodies of different concentrations diluted in equal proportions were added, and incubated at 4° C. for 30 minutes, and then 50 ul 1 ug/ml biotinylated SIRPα-Fc fusion protein solution was added, incubated at 4° C. for 30 minutes, then excess primary antibodies with 0.5% BSA/PBS were washed off, 50 ul secondary antibody SA-PE solution was added, and finally the cells were resuspend with 60 ul PBS solution containing 1 ug/ml fluorescent dye PI, immediately detected on the flow cytometer (FIG. 6-4). Experimental results show that the constructed human-mouse chimeric antibody can bind to CD47 on antigen and cells, and has the biological activity of competitively inhibiting the binding of CD47-SIRPα receptor and ligand.

Figure 7:
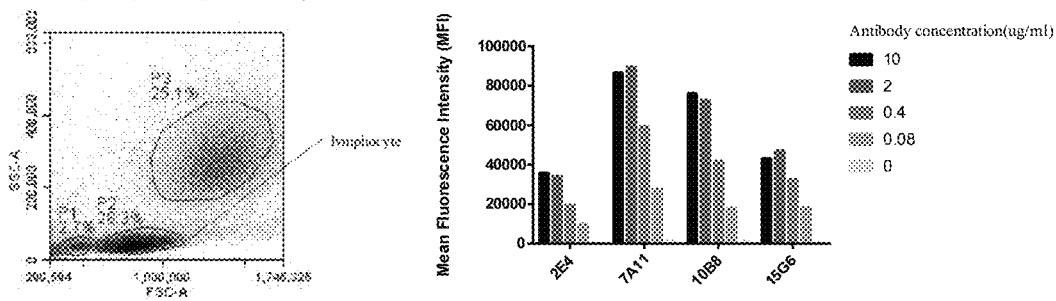
FIG. 7. shows CD47 antibody recognizes cynomolgus monkey lymphocytes.

8. Anti-CD47 Monoclonal Antibody Recognizes Cynomolgus Monkey Lymphocytes 4 ml fresh monkey blood was collected into a 50 ml centrifuge tube, 10 ml red blood cell lysate was added, stood at room temperature for 10 minutes, centrifuge at 1200 rpm for 10 minutes, washed twice with 20 ml PBS, the cells were counted before the second wash, the cells were prepared for staining at $2\times10^5$ cells/tube, centrifuged at 1200 rpm for 10 minutes, sealed with 100 ug/ml mouse IgG for 5-10 minutes, antibodies of different concentrations were added, incubated on ice for 60 minutes, washed twice to wash off the excess primary antibody, a second antibody (anti-human IgGFc-AF647, Jackson ImmunoResearch Cat: 109-606-170) was added, incubated on ice for 45 minutes, washed twice to wash off the excess secondary antibody, and finally the cells were resuspend with 1 ug/ml PI/PBS and detected with flow cytometry. The results are shown in FIG. 7.

9. Anti-CD47 Antibody-Mediated Phagocytosis

PBMC cells were isolated from fresh human blood with Ficoll (GE healtheare, Cat: 17-1440-03), then the supernatant of washed human PBMC cells was discarded, and the cells were resuspend with MACS Buffer ($1\times10^7$ Cells/80 uL), CD14 MicroBeads human-lyophilized ($10^7$ cells/20 uL) (MACS, Cat: 130097052) were added, non-mononuclear cells were eluted first through the sorting magnetic frame, and monocytes were finally eluted with MACS Buffer, and cultured with RPMI1640 culture medium (containing 40 ng/ml CSF-1) to induce into macrophages.

Figure 8:
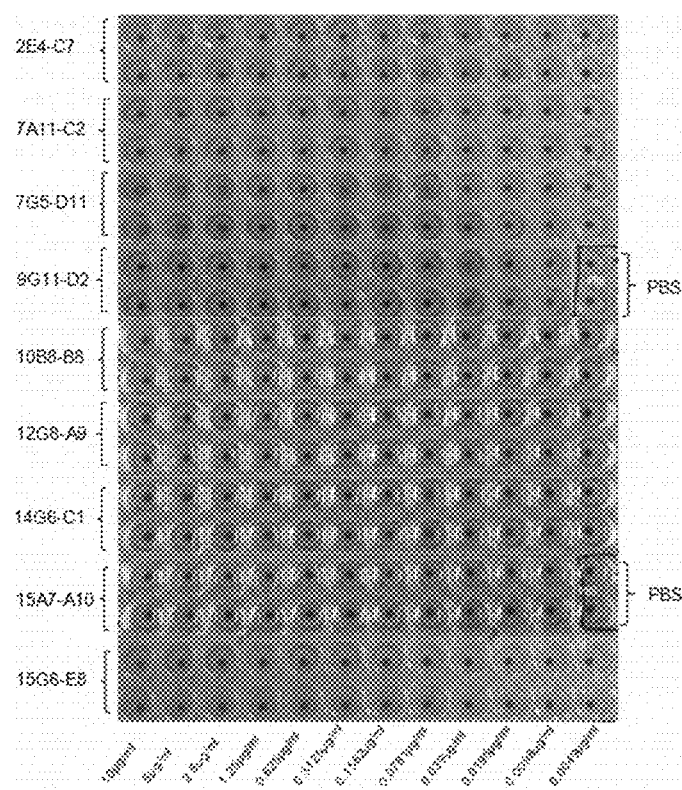
FIG. 8. shows anti-CD47 chimeric antibody has a concentration-dependent antibody-mediated phagocytosis.

CCRF-CEM cells labeled with 1 uM CFSE were used as CD47-positive target cells, 50 ul was inoculated into a 96-well plate at $1\times10^5$/well, then 50 ul antibody of 4 times the final concentration was added, and finally 100 ul mature macrophages of $2.5\times10^5$/ml density induced with CSF1 for 7-days were added, macrophages: CCRF-CEM=1:4, incubated in an incubator at 37° C. for 4 hours, and finally the collected cells were detected on a flow cytometer. The results were shown in FIG. 8.

Phagocytosis ratio % =

$$\frac{\text{Phagocytized cells number}}{\text{Phagocytized cells number} + \text{Non-phagocytized cells number}} \times 100\%$$

10. Assay of Erythrocyte Agglutination

Figure 9:
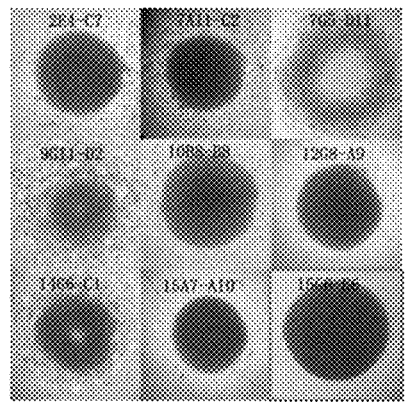
FIG. 9. The above picture shows the condition of the erythrocyte agglutination under the action of anti-CD47 monoclonal antibody in different concentrations, and the subclonal strains of hybridoma positive clones 7G5, 7A11, 9G11 and 14G6 can cause erythrocyte agglutination; the picture below shows the erythrocyte agglutination condition of anti-CD47 monoclonal antibody under microscope, and the hybridoma positive clones 2E4, 10B8, 12G8, 15A7 and 15G6 did not cause erythrocyte agglutination.

The antibody to be tested was diluted with twofold with PBS solution. the fact concentration was 10 ug/ml. Then 50 ul antibodies of different dilutions were added into the 96-well plate, then 50 ul fresh red blood cells with a density of $1\times10^8$/ml was added, visible aggregated particles appeared in some reaction holes after standing at room temperature for several minutes. The reaction wells without obvious agglutination phenomenon were confirmed whether there was erythrocyte agglutination by microscope after standing for 2 hours. The results are shown in FIG. 9.

11. Humanization of Antibodies

The humanization of the murine monoclonal antibody 15G6 was carried out according to the classic CDR transplantation strategy, which was, the CDR sequences of the light and heavy chain variable regions of the murine antibody 15G6 were transplanted to the high homology human germline sequence IGKV4-1*01 and IGHV1-3*01, framework region 4 selected IGKJ1*01 and IGHJ4*01, which had the highest homology with murine antibody; then, the computer was used for homology modeling at the same time to design back mutation sites.

The light and heavy chain derivatives were respectively synthesized (Suzhou Hongxun Biotechnology Company, Suzhou Jinweizhi Biotechnology Company), and cloned into a vector containing the antibody kappa chain constant region or human IgG1 constant region, and HEK293 0.6E cells were transfected after the plasmids were paired, expressed for 5-7 days, the supernatant was collected and purified with ProteinA column.

The humanized antibody heavy chain/light chain variable region sequence is as follows:

```
VH-v1:
                                        (SEQ ID NO: 101-104)
<-------------FR1------------> CDR1<----FR2----->
QIQLQQSGAEVKKPGASVKVSCKASGYTFTDYYIHWVRQAPGQGLEWMG

CDR2          <-----------FR3---------------->
WIYPGSGNTKYNEKFQGRVTLTVDTSSSTVYMELSSLRSDDTAVYFCAR

CDR3  <----FR4--->
RREDSFDYWGQGTLVTVSS

Nucleic acid sequence
                                             (SEQ ID NO: 105)
CAGATTCAGCTGGTCCAGTCTGGCGCCGAAGTGAAGAAACCTGGCGCCTC

TGTGAAGGTGTCCTGCAAGGCTAGCGGCTACACATTCACCCACTACTACA

TCCACTGGGTCCGACAGGCCCCTCGACACGGACTTGAATGGATGGGCTGG

ATCTACCCTGGCAGCGCCAACACCAAGTACAACGAGAAGTTCCAGGGCAC

AGTGACCCTGACCGTGGACACAAGCAGCAGCACCGTGTACATCGAACTGA

GCAGCCTGAGAAGCGACGATACCGCCGTGTACTTCTGTGCCAGAAGAAGA

GAGGACAGCTTCGACTACTGGGGCCAGGGAACACTGGTCACCGTTAGCTC
T

VH-v2:
                                        (SEQ ID NO: 106-109)
<-------------FR1------------> CDR1<----FR2----->
QVQLVQSGAEVKKPGASVKVSCKASGYTFTDYYIHWVRQAPGQGLEWMG

CDR2          <-----------FR3---------------->
WIYPGSGNTKYNEKFQGRVTLTVDTSTSTVYMELSSLRSDDTAVYYCAR

CDR3  <----FR4--->
RREDSFDYWGQGTLVTVSS

Nucleic acid sequence
                                             (SEQ ID NO: 110)
CAGGTTCAGCTGGTTCAGTCTGGCGCCGAAGTGAAGAAACCTGGCGCCTC

TGTGAAGGTGTCCTGCAAGGCTAGCGGCTACACATTCACCGACTACTACA

TCCACTGGGTCCGACAGGCCCCTGGACAGGGACTTGAATGGATGGGCTGG
```

-continued
```
ATCTACCCTGGCAGCGGCAACACCAAGTACAACGAGAAGTTCCAGGGCAG

AGTGACCCTGACCGTGGACACCAGCACAAGCACCGTGTACATGGAACTGA

GCAGCCTGAGAAGCGACGACACCGCCGTGTACTACTGCGCCAGAAGAAGA

GAGGACAGCTTCGACTACTGGGGCCAGGGAACACTGGTCACCGTTAGCTC

T
```

VH-v3:
(SEQ ID NO: 111-114)
```
<-------------FR1------------> CDR1<----FR2----->
QVQLVQSGAEVKKPGASVKVSCKASGYTFTDYYIHWVRQAFGQGLEWMG
      CDR2         <-----------FR3---------------->
WIYPGSGNTKYNEKFQGRVTMTVDTSTSTAYMELSSLRSDDTAVYYCAR
    CDR3  <----FR4--->
RREDSFDYWGQGTLVTVSS
```

Nucleic acid sequence
(SEQ ID NO: 115)
```
CAGGTTCAGCTGGTTCAGTCTGGCGCCGAAGTGAAGAAACCTGGCGCCTC

TGTGAAGGTGTCCTGCAASGCTAGCGGCTACACATTCACCGACTACTACA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCATGACCGTGGACACCAGCATCAGCACCGCCTACATGGAACTGA

GCAGCCTGAGAAGCGACGACACCGCCGTGTACTACTGCGCCAGAAGAAGA

GAGGACAGCTTCGACTACTGGGGCCAGGGAACACTGGTCACCGTTAGCTC

T
```

VH-v4:
(SEQ ID NO: 116-119)
```
<-------------FR1------------> CDR1<----FR2----->
QVQLVQSGAEVKKPGASVKVSCKASGYTFTDYYIHWVRQAPGQGLEWMG
      CDR2         <-----------FR3---------------->
WIYPGSGNTKYNEKFQGRVTMTRDTSISTVYMELSSLRSDDTAVYYCAR
    CDR3  <----FR4--->
RREDSFDYWGQGTLVTVSS
```

Nucleic acid sequence
(SEQ ID NO: 120)
```
CAGGTTCAGCTGGTTCAGTCTGGCGCCGAAGTGAAGAAACCTGGCGCCTC

TGTGAAGGTGTCCTGCAAGGCTAGCGGCTACACATTCACCGACTACTACA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCATGACCAGAGACACCAGCATCAGCACCGTGTACATGGAACTGA

GCAGCCTGAGAAGCGACGACACCGCCGTGTACTACTGCGCCAGAAGAAGA

GAGGACAGCTTCGACTACTGGGGCCAGGGAACACTGGTCACCGTTAGCTC

T
```

VH-v5:
(SEQ ID NO: 121-124)
```
<-------------FR1------------> CDR1<----FR2----->
QVQLVQSGAEVKKPGASVKVSCKASGYTFTDYYIHWVRQAPGQGLEWMG
      CDR2         <-----------FR3---------------->
WIYPGSGNTKYNEKFQGRVTMTRDTSISTAYMELSSLRSDDTAVYYCAR
    CDR3  <----FR4--->
RREDSFDYWGQGTLVTVSS
```

Nucleic acid sequence
(SEQ ID NO: 125)
```
CAGGTTCAGCTGGTTCAGTCTGGCGCCGAAGTGAAGAAACCTGGCGCCTC

TGTGAAGGTGTCCTGCAAGGCTAGCGGCTACACATTCACCGACTACTACA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCATGACCAGAGACACCAGCATCAGCACCGCCTACATGGAACTGA

GCAGCCTGAGAAGCGACGACACCGCCGTGTACTACTGCGCCAGAAGAAGA

GAGGACAGCTTCGACTACTGGGGCCAGGGAACACTGGTCACCGTTAGCTC

T
```

VH-v6:
(SEQ ID NO: 126-129)
```
<-------------FR1------------> CDR1<----FR2----->
QVQLVQSGPEVKKPGASVKVSCKASGYTFTDYYIHWVRQAPGQGLEWMG
      CDR2         <-----------FR3---------------->
WIYPGSGNTKYNEKFQGRVTLTVDTSTSTVYMELSSLRSDDTAVYYCAR
    CDR3  <----FR4--->
RREDSFDYWGQGTLVTVSS
```

Nucleic acid sequence
(SEQ ID NO: 130)
```
CAGGTTCAGCTGGTTCAGTCTGGCcctGAAGTGAAGAAACCTGGCGCCTG

TGTGAAGGTGTCCTGCAAGGCTAGCGGCTACACATTCACCGACTACTACA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCCTGACCGTGGACACCAGCACAAGCACCGTGTACATGGAACTGA

GCAGCCTGAGAAGCGACGACACCGCCGTGTACTACTGCGCCAGAAGAAGA

GAGGACAGCTTCGACTACTGGGGCCAGGGAACACTGGTCACCGTTAGCTC

T
```

VH-v7:
(SEQ ID NO: 131-134)
```
<-------------FR1------------> CDR1<----FR2----->
QVQLVQSGAELKKPGASVKVSCKASGYTFTDYYIHWVRQAPGQGLEWMG
      CDR2         <-----------FR3---------------->
WIYPGSGNTKYNEKFQGRVTLTVDTSTSTVYMELSSLRSDDTAVYYCAR
    CDR3  <----FR4--->
RREDSFDYWGQGTLVTVSS
```

Nucleic acid sequence (SEQ ID NO: 135)

CAGGTTCAGCTGGTTCAGTCTGGCGCCGAActgAAGAAACCTGGCGCCTC

TGTGAAGGTGTCCTGCAAGGCTAGCGGCTACACATTCACCGACTACTCA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCCTGACCGTGGACACCAGCACAAGCACCGTGTACATGGAACTGA

GCAGCCTGAGAAGCGACGACACCGCCGTGTACTACTGCGCCAGAAGAAGA

GAGGACAGCTTCGACTACTGGGGCCAGGGAACAACTGTCACCGTTAGCTC

T

VH-v8:

(SEQ ID NO: 136-139)

<-------------FR1------------> CDR1<----FR2----->
QVQLVQSGAEVKKPGASVKVSCKASGYTFTDYYIHWVRQAPGQGLEWMG

CDR2        <-----------FR3---------------->
WIYPGSGNTKYNEKFQGRVTLTVDTSTSTVYMELSSLRSDDIAVYYCAR

CDR3  <----FR4--->
RREDSFDYWGQGTLVTVSS

Nucleic acid sequence (SEQ ID NO: 140)

CAGGTTCAGCTGGTTCAGTCTGGCGCCGAAGTGAAGAAACCTGGCGCCTG

TGTGAAGGTGTCCTGCAAGGCTAGCGGCTACACATTCACCGACTACTCA

TCCACTGGGTCCGACAGGCCCCTGGACAGGGACTTGAATGGATGGGCTGG

ATCTACCCTGGCACCGGCAACACCAAGTACAACGAGAACTTCCAGGGCAG

AGTGACCCTGACCGTGGACACCAGCACAAGCACCGTGTACATGGAACTGA

GCAGCCTGAGAAGCGACGACATTGCCGTGTACTACTGCGCCAGAAGAAGA

GAGGACAGCTTCGACTACTGGGGCCAGGGAACACTGGTCACCGTTAGCTC

T

VH-v9:

(SEQ ID NO: 141-144)

<-------------FR1------------> CDR1<----FR2----->
QVQLVQSGAEVKKPGASVKVSCKASGYTFTDYYIHWVRQAPGQGLEWMG

CDR2        <-----------FR3---------------->
WIYPGSGNTKYNEKFQGRVTLTVDTSTSTVYMELSSLRSDDTAVYYCAR

CDR3  <----FR4--->
RREDSFDYWGQGTLVTVSS

Nucleic acid sequence (SEQ ID NO: 145)

CAGGTTCAGCTGGTTCAGTCTGGCGCCGAAGTGAAGAAACCTGGCGCCTC

TGTGAAGGTGTCCTGCAAGGCTAGCGGCTACACATTCACCGACTACTCA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCCTGACCGTGGACACCAGCACAAGCACCGTGTACATGGAACTGA

GCAGCCTGAGAAGCGACGACACCGCCGTGTACTACTGCGCCAGAAGAAGA

GAGGACAGCTTCGACTACTGGGGCCAGGGAACAACTGTCACCGTTAGCTC

T

VH-v10:

(SEQ ID NO: 146-149)

<-------------FR1------------> CDR1<----FR2----->
QVQLVQSGPELKKPGASVKVSCKASGYTFTDYYIHWVRQAPGQGLEWMG

CDR2        <-----------FR3---------------->
WIYPGSGNTKYNEKFQGRVTLTVDTSTSTVYMELSSLRSDDTAVYYCAR

CDR3  <----FR4--->
RREDSFDYWGQGTLVTVSS

Nucleic acid sequence (SEQ ID NO: 150)

CAGGTTCAGCTGGTGCAGTCTGGACCCGAGCTGAAGAAACCTGGCGCCTC

TGTGAAGGTGTCCTGCAAGGCTAGCGGCTACACATTCACCGACTACTCA

TCCACTGGGTCCGACAGGCCCCTGGACAGGGACTTGAATGGATGGGCTGG

ATCTACCCTGGCAGCGGCAACAGGAAGTACAACGAGAAGTTCCAGGGCAG

AGTGACCCTGACCGTGGACACCAGCACAAGCACCGTGTACATGGAACTGA

GCAGCCTGAGAAGCGACGACACCGCCGTGTACTACTGCGCCAGAAGAAGA

GAGGACAGCTTCGACTACTGGGGCCAGGGAACACTGGTCACCGTTACGTC

T

VH-v11:

(SEQ ID NO: 151-154)

<-------------FR1------------> CDR1<----FR2----->
QIQLVQSGAELKKPGASVKVSCKASGYTFTDYYIHWVRQAPGQGLEWMG

CDR2        <-----------FR3---------------->
WIYPGSGNTKYNEKFQGRVTLTVDTSSSTVYMELSSLRSDDTAVYPCAR

CDR3  <----FR4--->
RREDSFDYWGQGTLVTVSS

Nucleic acid sequence (SEQ ID NO: 155)

CAGATTCAGCTGGTGCAGTCTGGCGCCGAACTGAAGAAACCTGGCGCCTC

TGTGAAGGTGTCCTGCAAGGCTAGCGGCTACACATTCACCGACTACTCA

TCCACTGGGTCCGACAGGCCCCTGGACAGGGACTTGAATGGATGGGCTGG

ATCTACCCTGGCAGCGGCAACACCAAGTACAACGAGAAGTTCCAGGGCAG

AGTGACCCTGACCGTGGACAAGCAGCAGCACCGTGTACATGGAACTGA

GCAGCCTGAGAAGCGACGATACCGCCGTGTACTTCTGTGCCAGAAGAAGA

GAGGACAGCTTCGACTACTGGGGCCAGGGAACACTGGTCACCGTTAGCTC

T

Vk-v1:
(SEQ ID NO: 156-159)
```
<----------FR1--------->      CDR1       <------
DIVMTQSPDSLAVSLGERATINCKSSQSLLYSSNQKNYLAWYQRKPG

FR2----> CDR2  <------FR3---------------------->
QPPKLLIYWASNRESGVPDRFSGSGSGTDFTLTISSLQAEDVAVYYC

CDR3   <---FR4--->
QQFYRYPLTFGQGTKVEIK
```

Nucleic acid sequence
(SEQ ID NO: 160)
GACATCGTGATGACACAGAGCCCTGATAGCCTGGCCGTGTCTCTGGGAGA

GAGAGCCACCATCAACTGCAAGAGCAGCCAGAGCCTGCTGCTACTCCAGC

AACCAGAAGAACTACCTGGCCTGGTATCAGAGAAAGCCCGCCAGCCTCCT

AAGCTGCTGATCTACTGGGCCAGCAACAGAGAATCCGGCGTGCCCGATAG

ATTCAGCGGCTCTGGATCTGGACACGACTTCACCCTGACAATCAGCTCCC

TGCAGGCCGAGGATGTGGCCGTGTACTACTGCCAGCAGTTCTACAGATAC

CCTCTCACCTTCGGCCAGGGCACCAAGGTGGAAATCAAG

Vk-v2:
(SEQ ID NO: 161-164)
```
<----------FR1--------->      CDR1       <------
DIVMTQSPDSLAVSLGERATINCKSSQSLLYSSNQKNYLAWYQQKP

FR2-----> CDR2  <------FR3--------------------->
GQPPKLLIYWASNRESGVPDRFSGSGSGTDFTLTISSLQAEDVAVYYC

CDR3   <---FR4--->
QQFYRYPLTFGQGTKVEIK
```

Nucleic acid sequence
(SEQ ID NO: 165)
GACATCGTGATGACACAGAGCCCTGATAGCCTGGCCGTGTCTCTGGGAGA

GAGAGCCACCATCAACTGCAAGAGCAGCCAGAGCCTGCTGTACTCCAGCA

ACCAGAAGAACTACCTGGCCTGGTATCAGCAGAAGCCCGGCCAGCCTCCT

AAGCTGCTGATCTACTGGGCCAGCAACAGAGAAAGCGGCGTGCCCGATAG

ATTCAGCGGCTCTGGATCTGGCACCGACTTCACCCTGACAATCAGCTCCC

TGCAGGCCGAGGATGTGGCCGTGTACTACTGCCAGCACTTCTACAGATAC

CCTCTGACCTTCGGCCAGGGCACCAAGGTGGAAATCAAG

Vk-v3:
(SEQ ID NO: 166-169)
```
<----------FR1--------->      CDR1       <------
DIVMTQSPDSLTVSLGERATINCKSSQSLLYSSNQKNYLAWYQQKPG

FR2----> CDR2  <------FR3---------------------->
QPPKLLIYWASNRESGVPDRFSGSGSGTDFTLTISSLQAEDVAVYYC

CDR3   <---FR4--->
QQFYRYPLTFGQGTKVEIK
```

Nucleic acid sequence
(SEQ ID NO: 170)
GACATCGTGATGACACAGAGCCCTGATAGCCTGactGTGTCTCTGGGAGA

GAGAGCCACCATCAACTGCAAGAGCAGCCAGAGCCTGCTGTACTCCAGCA

ACCAGAAGAACTACCTGGCCTGGTATCAGCAGAAGCCCGGCCAGCCTCCT

AAGCTGCTGATCTACTGGGCCAGCAACAGAGAAAGCGGCGTGCCCGATAG

ATTCAGCGGCTCTGGATCTGGCACCGACTTCACCCTGACAATCAGCTCCC

TGCAGGCCGAGGATGTGGCCGTGTACTACTGCCAGCAGTTCTACAGATAC

CCTCTGACCTTCGGCCAGGGCACCAAGGTGGAAATCAAG

Vk-v4:
(SEQ ID NO: 171-174)
```
<----------FR1--------->      CDR1       <------
DIVMTQSPDSLAVSLGERATINCKSSQSLLYSSNQKNYLAWYQQKPG

FR2----> CDR2  <------FR3---------------------->
QPPKLLIYWASNRESGVPDRFSGSGSGTDFTLTISSLQAEDVAVYYC

CDR3   <---FR4--->
QQFYRYPLTFGQGTKVEIK
```

Nucleic acid sequence
(SEQ ID NO: 175)
GACATCGTGATGACACAGAGCCCTGATAGCCTGGCCGTGTCTCTGGGAGA

GAGAGCCACCATCAACTGCAAGAGCAGCCAGAGCCTGCTGTACTCCAGCA

ACCAGAAGAACTACCTGGCCTGGTATCAGCAGAAGCCCGGCCAGCCTCCT

AAGCTGCTGATCTACTGGGCCAGCAACAGAGAAAGCGGCGTGCCCGATAG

ATTCAGCGGCTCTGGATCTGGCACCGACTTCACCCTGACAATCAGCTCCC

TGCAGGCCGAGGATGTGGCCGTGTACTACTGCCAGCAGTTCTACAGATAC

CCTCTGACCTTCGGCCAGGGCACCAAGCTGGAAATCAAG

Vk-v5:
(SEQ ID NO: 176-179)
```
<----------FR1--------->      CDR1       <------
DIVMTQSPDSLAVSLGERATINCKSSQSLLYSSNQKNYLAWYQQKP

FR2----> CDR2  <------FR3---------------------->
GQPPKLLIYWASNRESGVPDRFSGSGSGTDFTLTISSLQAEDVAVYYC

CDR3   <---FR4--->
QQFYRYPLTFGQGTKVELK
```

Nucleic acid sequence
(SEQ ID NO: 180)
GACATCGTGATGACACAGAGCCCTGATAGCCTGGCCGTGTCTCTGGGAGA

GAGAGCCACCATCAACTGCAAGAGCAGCCAGAGCCTGCTGTACTCCAGCA

ACCAGAAGAACTACCTGGCCTGGTATCAGCAGAAGCCCGGCCAGCCTCCT

AAGCTGCTGATCTACTGGGCCAGCAACAGAGAAAGCGGCGTGCCCGATAG

ATTCAGCGGCTCTGGATCTGGCACCGACTTCACCCTGACAATCAGCTCCC

TGCAGGCCGAGGATGTGGCCGTGTACTACTGCCAGCAGTTCTACAGATAC

CCTCTGACCTTCGGCCAGGGCACCAAGGTGGAACTGAAG

12. Binding of Humanized Antibody h15G6 to CD47 and Blocking of CD47-SIRP α

Figure 10:
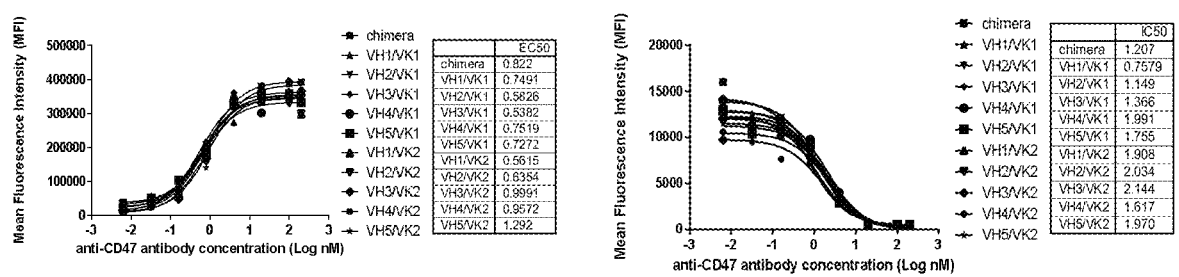
FIG. 10. The affinity of humanized antibodies on cells and the blocking effect on CD47-SIRPα binding.

All heavy and light chains were constructed on a eukaryotic expression vector, all heavy and light chains were paired with each other, and the transiently expressed antibodies were used for affinity detection and receptor ligand blocking experiments. The results show that the affinity of the humanized antibody to CD47 and the ability of blocking receptor ligands did not change significantly. The red blood cell agglutination test was further carried out, and the result was shown in FIG. 10, which showed that there was no coagulation phenomenon.

13. Determination of Affinity of Humanized Antibody h15G6

The affinity of anti-CD47 monoclonal antibody and human CD47 molecule was determined by Fortbio, ELISA and FACS.

Fortbio Affinity Characterization

Figures 11A, 11B:
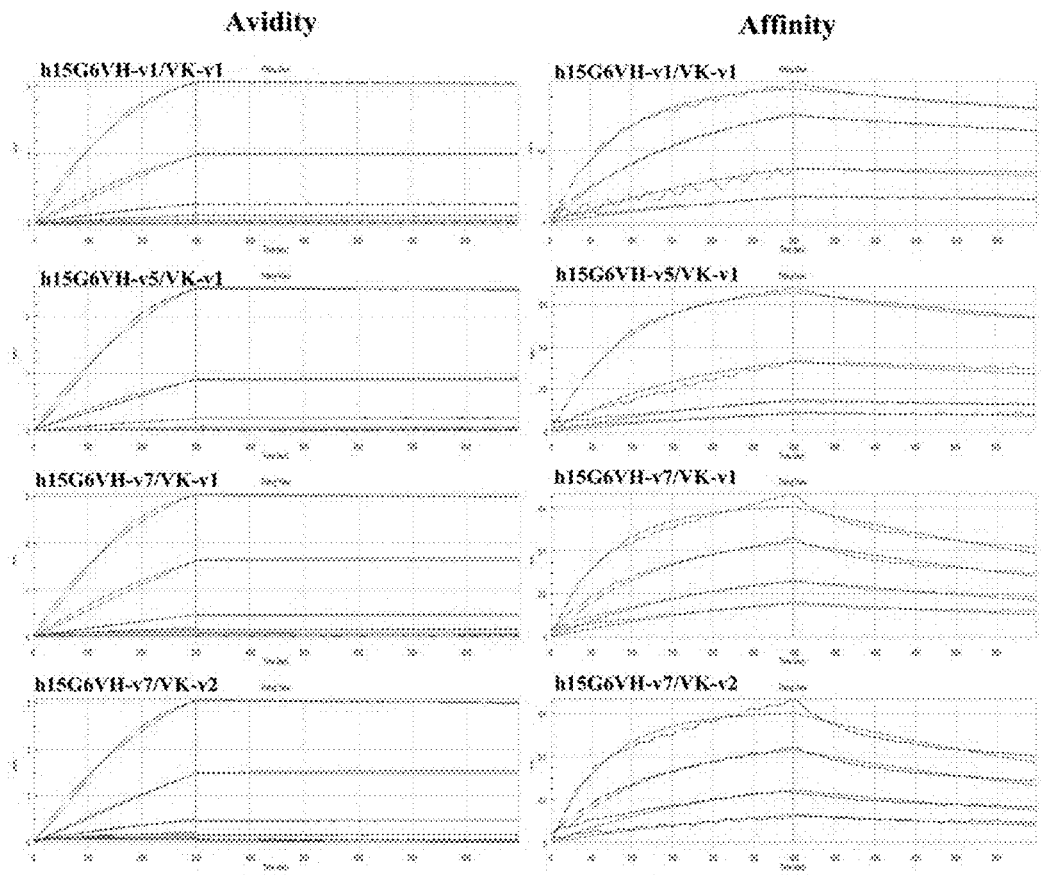
FIG. 11. The above figure shows detection of the avidity of h15G6VH-v1NK-v1, VH-v5/VK-v1, VH-v7/VK-v1, VH-v7/VK-v2 with coated biotin antigen; the figure below shows the detection of the affinities of h15G6VH-v1/VK-v1, VH-v5/VK-v1, VH-v7/VK-v1, VH-v7/VK-v2 with coated biotin antibody.

Protein A probes were coated with 5 ug/ml antibody to be tested, and the recombinant protein hCD47 was serially diluted, and the concentration was set to 5 ug/ml, 2.5 ug/ml, 1.25 ug/ml, 0.625 ug/ml, 0 ug/ml, and then the samples were detected with Fortbio instrument. The results were shown in FIG. 11.

Figure 12:
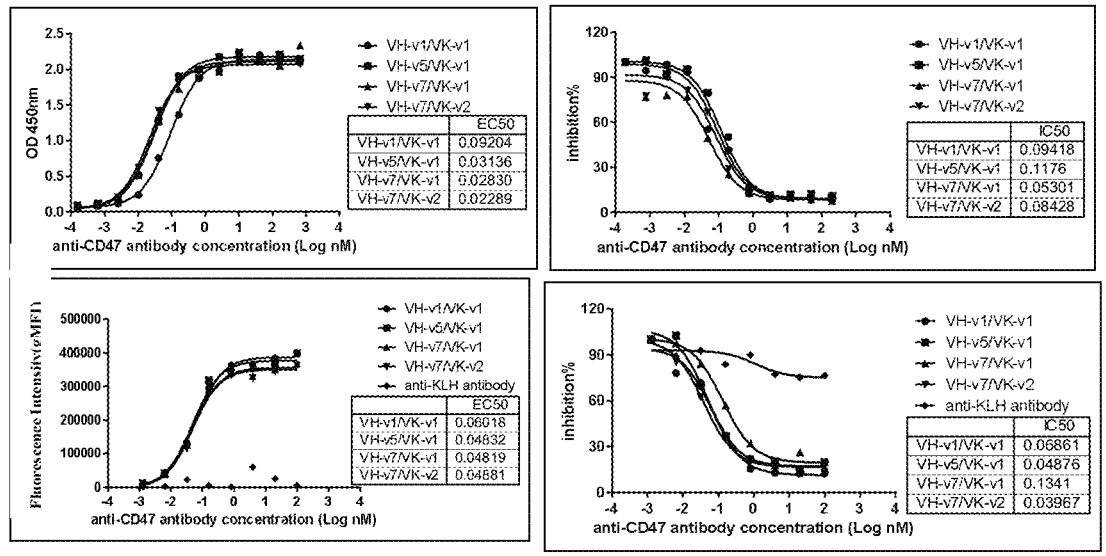

ELISA and FACS methods were further used to detect at the antigen level and cell level that the humanized antibody could bind to human CD47 molecules and inhibit the binding of receptor ligand CD47-SIRPα. The results were shown in FIG. 12.

14. Humanized h15G6-IgG4 Antibody-Mediated Cellular Phagocytosis (ADCP)

PBMC cells were separated from fresh human blood with Ficoll (GE healtheare, Cat: 17-1440-03), the supernatant of washed human PBMC cells was discarded, and the cells were resuspend with MACS Buffer ($1 \times 10^7$ Cells/80 uL), CD14 MicroBeads human-lyophilized ($10^7$ cells/20 uL) (MACS, Cat: 130097052) were added, non-mononuclear cells were eluted first through the sorting magnetic frame, and monocytes were finally eluted with MACS Buffer, cultured with RPMI1640 culture medium (containing 40 ng/ml CSF-1) to induce into macrophages.

The humanized h15G6 variable region was inserted into a plasmid vector expressing a complete human IgG4 antibody heavy chain, for expressing h15G6-IgG4 in mammalian cells. After the correct sequencing, the plasmid was transiently expressed candidate antibody CD47 in the mammalian cell HEK293.6E, and the cell supernatant was collected 5-7 days later, filtered and purified. IgG was purified by Protein A chromatography, and washed with 50 mM Tris-HCl pH8.0, 250 mM NaCl, and the bound IgG was eluted with 0.1M Glycine-HCl, pH3.0. The proteins were concentrated by ultrafiltration by using a concentration tube (Millipore), and exchanged to a PBS solution, and the IgG concentration was measured.

Figure 13:
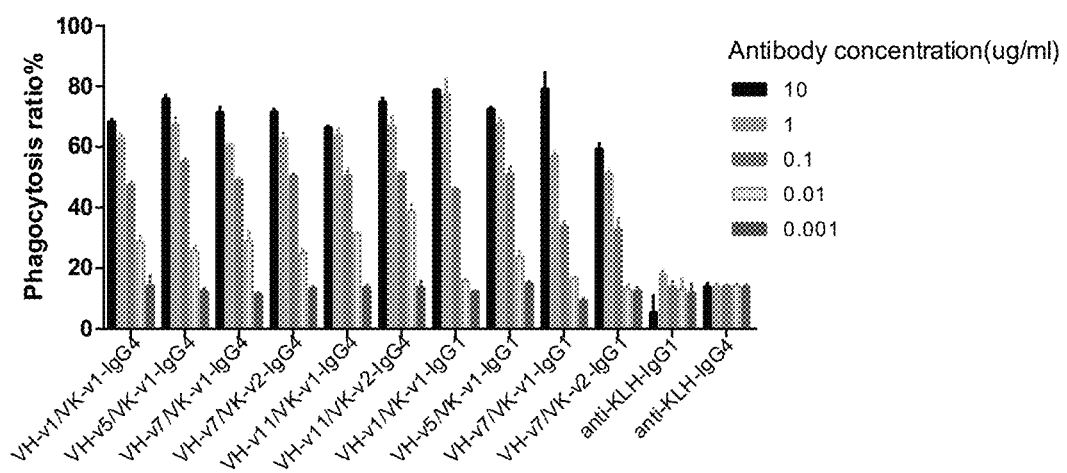
FIG. 13. The results above show that the humanized h15G6 antibody has ADCP biological activity.

CCRF-CEM cells labeled with 1 uM CFSE were used as CD47-positive target cells, 50 ul inoculated into a 96-well plate at $1 \times 10^5$/well, then 50 ul h15G6 humanized antibody (IgG4) diluted 4 times of the final concentration was added, and finally 100 ul mature macrophages of density $2.5 \times 10^5$/ml induced with CSF-1 for 7-days were added, macrophages: CCRF-CEM=1:4, incubated at 37° C. for 4 hours, and finally the collected cells were detected on flow cytometer. The results were shown in FIG. 13.

15. The Synergistic Effect of Humanized Antibody h15G6 and Rituximab

Figure 14:
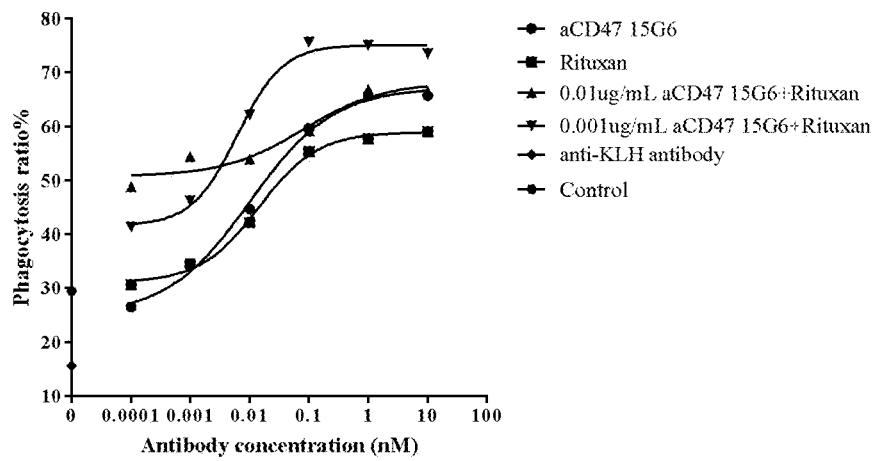
FIG. 14. The results show that the combination of the h15G6 antibody and rituximab significantly increases the macrophage phagocytosis.

Daudi cells labeled with 1 uM CFSE were used as CD47+ target cells, 50 ul was inoculated into a 96-well plate at $1 \times 10^5$/well, then 50 ul humanized h15G6-IgG4 antibody diluted 4 times of the final concentration was added, and finally 100 ul mature macrophages of density $2.5 \times 10^5$/ml induced with CSF-1 for 7-days were added, macrophages: Daudi cells=1:4, incubated at 37° C. for 4 hours, and finally the collected cells were detected on flow cytometer. The results were shown in FIG. 14.

Phagocytosis ratio % =

$$\frac{\text{Phagocytized cells number}}{\text{Phagocytized cells number} + \text{Non-phagocytized cells number}} \times 100\%$$

16. Fc Function Test of Humanized h15G6 Antibody

Antibody-Dependent Cell-Mediated Cytotoxicity (ADCC)

Figure 15:
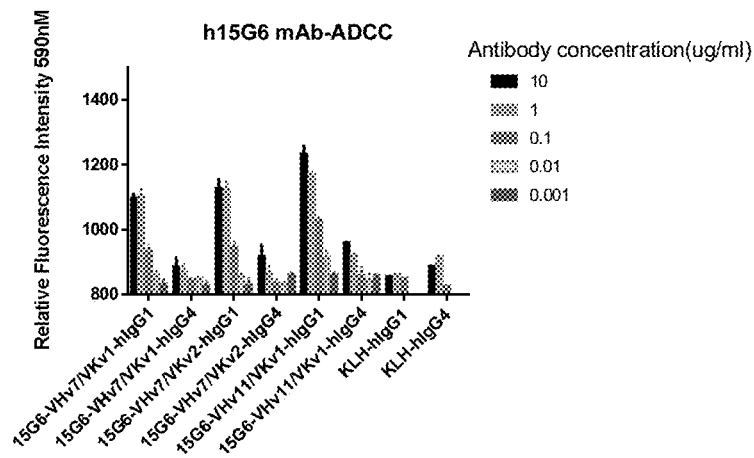
FIG. 15. Antibody Fc function detection shows that the humanized h15G6-IgG1 antibody has a strong ADCC effect, and the ADCC effect of h15G6-IgG4 is absent.

An appropriate amount of effector cells (NK-92MI-CD16) was taken out, and the cells were resuspend to a density of $4 \times 10^6$/ml with RPMI1640 culture medium containing 2.5% FBS. Similarly, the target cells (CCRF-CEM) were resuspend to the density of $4 \times 10^5$/ml. The initial concentration of the antibody was set to 40 ug/ml, and then diluted by 10 times. 50 ul ($2 \times 10^5$/well) of effector cells was taken into a 96-well U-shaped plate, 25 ul antibodies with different dilution ratios were added, and incubated in 5% $CO_2$ incubator for 30 minutes at 37° C. After the incubation was completed, 25 ul ($1 \times 10^4$/well) target cells were added, centrifuged at 1000 rpm for 1 minute, and incubated at 37° C. in a 5% $CO_2$ incubator for 4 hours. 30 minutes before the detection, 2 ul lysis buffer (10×) was added to the largest well of the target cell, and put back to continue culturing. After 30 minutes, centrifuged at 1000 rpm for 3 minutes, 50 ul cell supernatant was taken out to the black microplate plate, the same amount of LDH detection substrate (Cyto-Tox-ONE Homogeneous Membrane Integrity Assay, Promega Cat: G7892) was added, gently shaken and uniformly mixed for 10 minutes, then the reaction was terminated with 25 ul terminated-solution, oscillated for 10 s, Fluorescence wavelength excitation: 560 nm, emission: 590 nm were selected to detect chemiluminescence. The results were shown in FIG. 15.

Complement-Mediated Cytotoxicity (CDC)

Figure 16:
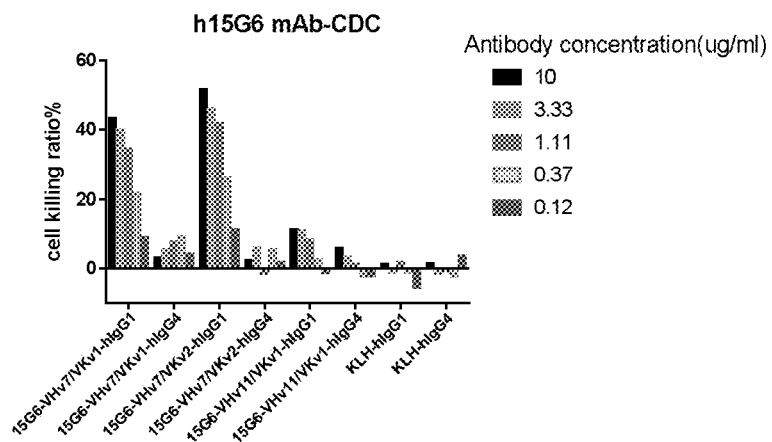
FIG. 16. Antibody Fc function detection shows that the humanized h15G6-IgG1 antibody has a strong CDC effect, and the CDC effect of h15G6-IgG4 is absent.

The target cells (CCRF-CEM) were resuspended to a density of $2 \times 10^6$/ml. The initial antibody concentration was set to 30 ug/ml, and the antibody was diluted in an equal ratio with RPMI1640 culture medium in a ratio of 1:3. 30% complement was prepared with RPMI1640 medium. 50 ul ($1 \times 10^5$/well) cell suspension was taken into a 96-well plate, then 50 ul antibodies of different dilution concentrations were added, and then 50 ul was added to dilute into 30% complement, and incubated in 5% $CO_2$ incubator at 37° C. for 2 hours. A detection solution containing 40% CCK8 was prepared with RPMI medium (containing 0.1% BSA). After cell-antibody-complement incubation for 2 hours, 50 ul CCK8 solution was added to each well for staining, shaken for 10 seconds, and incubated in the 5% $CO_2$ incubator at 37° C. for 4 hours. After the incubation is completed, the plate was shaken for 10 seconds, and the OD value was read with a microplate reader at 450 nm detection wavelength, and 630 nm as the reference wavelength. The results were shown in FIG. 16.

17. Toxicity Test of Anti-CD47 Monoclonal Antibody in CD47 Humanized Mice

CD47 humanized mouse C57BL/6-Cd47$^{tm1(hCD47)}$/Bcgen (Biocytogen, Cat:B-CM-021) was selected, and the antibodies (10 mg/kg body weight) were administered by intraperitoneal injection for 2 rounds, 3 test mice each group. On the day 2, 6, 9, and 13 after the first administration, blood was collected from the test mice for routine blood testing. On the 7th day, the second administration was performed.

Figure 17:
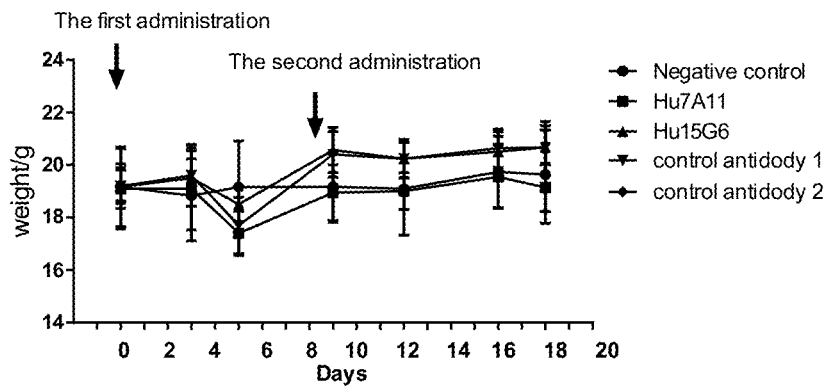
FIG. 17. Changes of the body weight of humanized mice after twice administrations of CD47 antibodies.

On the 9, 13, and 18 days, the tested mice were undergone routine blood testing. The results were shown in FIG. 17.

The weight results of the tested mice showed that the weight of the mice began to decrease on the 3rd day after the first administration, and the weight of the mice recovered on the 6th day. The second administration was performed the next day, the body weight of the mice did not change significantly on the 3rd day after the second administration, and the body weight of the tested mice remained stable within the normal range in the following 11 days. In the positive control group control 2, the three groups of mice died on the third day after the first injection of CD47 antibody, and the remaining mice were normal.

Figure 18:
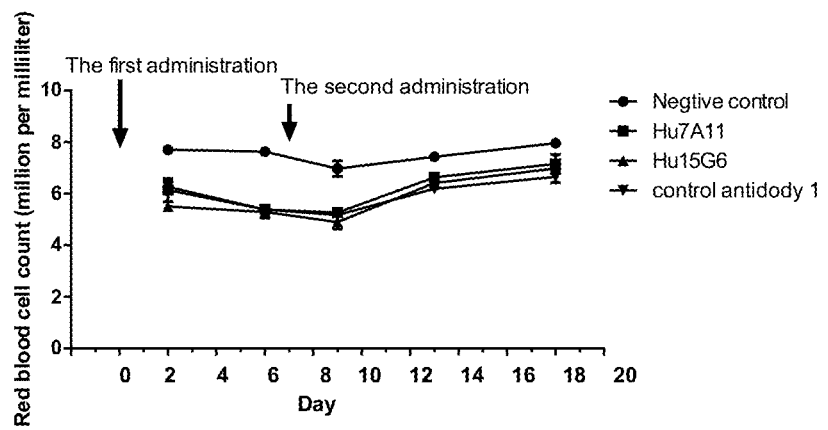
FIG. 18. Changes of peripheral blood erythrocytes of humanized mice after twice administrations of CD47 antibodies.

The results of blood routine test and blood biochemical analysis were shown in FIG. 18, which showed that after the first administration of anti-CD47 monoclonal antibody, compared with the blank control group, the number of peripheral red blood cells decreased in the tested mince group, and the number of red blood cells was basically stable after the second administration, and basically returned to normal in a week.

18. Anti-Tumor Effect of Humanized CD47 Monoclonal Antibody in Subcutaneous Xenograft NOD/SCID Mouse Model of Human Burkitt Lymphoma Raji Cell Line Raji cells were cultured in RPMI1640 medium containing 10% fetal bovine serum. The Raji cells in logarithmic growth phase were collected, resuspended in PBS to a suitable concentration and mixed with matrigel 1:1, and used for subcutaneous tumor inoculation in NOD/SCID mice. Female mice were inoculated subcutaneously with $1\times10^7$ Raji cells on the right side. When the average tumor volume was 89.39 mm$^3$, randomly grouped according to tumor size. There were 6 mice in each group, and mice in the treatment group were injected into the tail vein twice a week at a dose of 10 mg/kg for two weeks. The tumor volume was monitored. The tumor volume calculation method was: tumor volume (mm$^3$)=½×(a×b$^2$) (wherein a represented the long diameter and b represented the short diameter).

Figure 19:
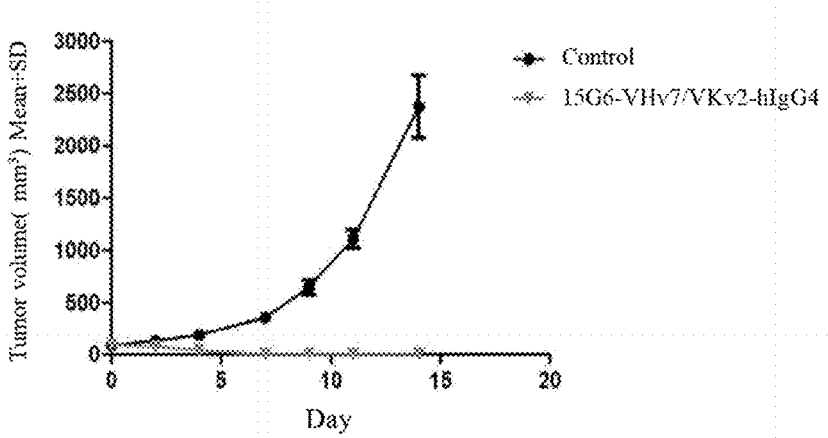
FIG. 19. The anti-tumor effect of humanized CD47 monoclonal antibody 6 in subcutaneous xenograft NOD/SCID mouse model of human Burkitt's lymphoma Raji cell lines.

The results were shown in FIG. 19. On the 9th day after the first administration, the average tumor volume of the mice in the vehicle control group grew to 649.67 mm$^3$, and the tumors in the treatment group had completely disappeared. The tumor volume was 0 mm$^3$ and the relative tumor inhibition rate reached 100%.

19. Anti-Tumor Effect of Humanized CD47 Monoclonal Antibody in Subcutaneous Xenograft NPG Mouse Model of Human Ovarian Cancer SKOV-3 Cell SKOV-3 cells were cultured in McCoy's5a medium containing 10% fetal bovine serum. The SK-OV-3 cells in the logarithmic growth phase were collected, resuspended in PBS to a suitable concentration and mixed with matrigel 1:1, and used for subcutaneous tumor inoculation of NPG mice. Female mice were subcutaneously inoculated with $1\times10^7$ SKOV-3 cells on the right side. When the average tumor volume was 93.76 mm$^3$, randomly grouped according to tumor size. There were 6 mice in each group. The mice in the treatment group were injected into the tail vein at a dose of 10 mg/kg three times a week for four weeks, and the tumor volume was monitored. The tumor volume calculation method was: tumor volume (mm$^3$)=½×(a×b$^2$) (wherein a represented the long diameter and b represented the short diameter).

Figure 20:
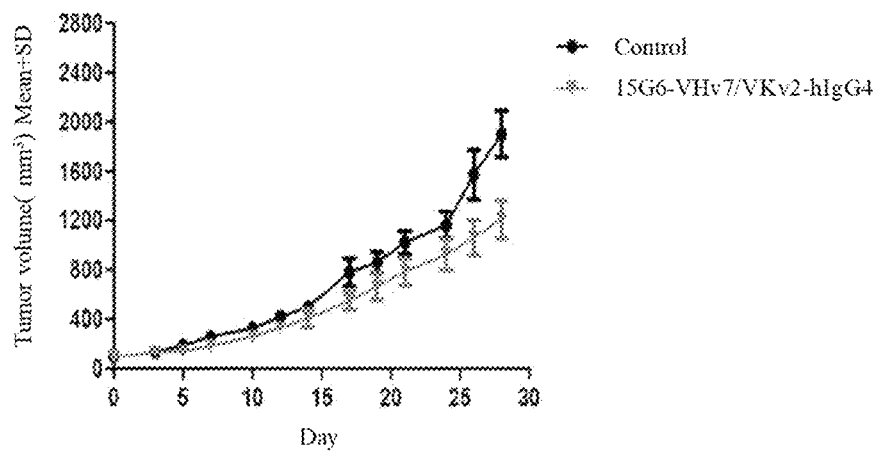
FIG. 20. The anti-tumor effect of humanized CD47 monoclonal antibody 6 in subcutaneous xenograft NPG mouse model of human ovarian cancer SKOV-3 cells.

The results were shown in FIG. 20. On the second day after the last administration, the average tumor volume of mice in the vehicle control group was 1905.53 mm$^3$, and the tumor volume of the treatment group was 1209.74 mm$^3$. Compared with the vehicle control group, the relative tumor inhibition rate was 36.51%, showing a significant tumor inhibition effect (p value is 0.0211).

20. Anti-Tumor Effect of Humanized CD47 Monoclonal Antibody in Human Promyelocytic Leukemia Cell HL-60 Subcutaneous Xenograft NPG Mouse Model HL-60 cells were cultured in RPMI1640 medium containing 10% fetal bovine serum. HL-60 cells in logarithmic growth phase were collected, resuspended in PBS to a suitable concentration and mixed with matrigel 1:1, and used for subcutaneous tumor inoculation in NPG mice. Female mice were inoculated subcutaneously with $1\times10^7$ HL-60 cells on the right side. When the average tumor volume was 107.9 mm$^3$, randomly grouped according to tumor size. There were 6 mice in each group. The mice in the treatment group were administered at doses of 3 mg/kg and 10 mg/kg for two weeks, three times in the first week and twice in the second week. Monitor tumor volume. The tumor volume calculation method was: tumor volume (mm$^3$)=½×(a×b$^2$) (wherein a represents the long diameter and b represents the short diameter).

Figure 21:
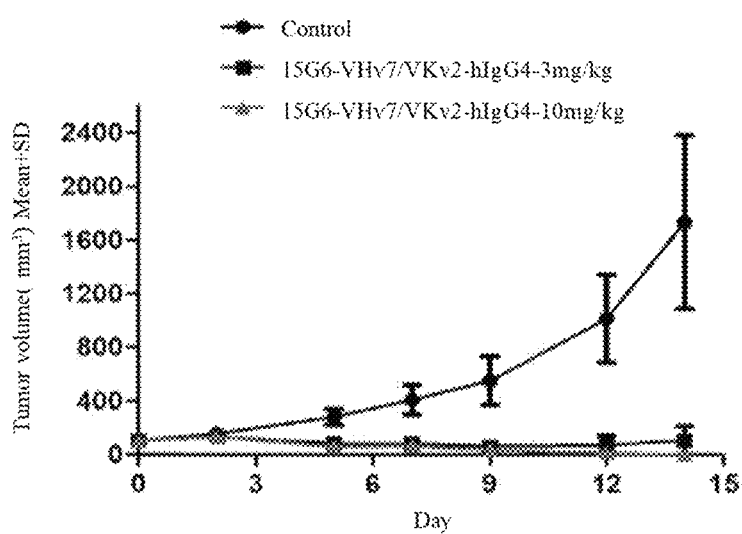
FIG. 21. The anti-tumor effect of humanized CD47 monoclonal antibody in subcutaneous xenograft NPG mouse model of human promyelocytic leukemia HL-60 cells.

The results were shown in FIG. 21. On the 14th day after the first administration, the average tumor volume of mice in the vehicle control group was 1734.22 mm$^3$, and the average tumor volume of the 10 mg/kg and 3 mg/kg treatment groups were 0 mm$^3$ and 107.13 mm$^3$, respectively. The treatment group showed significant anti-tumor effect at the two doses of 10 mg/kg and 3 mg/kg, and the relative tumor inhibition rate TGI (%) was 100% and 96.78%, respectively.

21. Anti-Tumor Effect of Humanized CD47 Monoclonal Antibody in Lung Cancer PDX Mouse Model with High CD47 Expression Tumor tissues were collected from tumor-bearing mice of tumor tissue xenotransplantation models of lung cancer patients, cut into tumor masses with a diameter of 2-3 mm, and inoculated subcutaneously at the right anterior scapula of NPG mice. When the average tumor volume was 102.97 mm$^3$, randomly grouped according to tumor size. There were 6 mice in each group. The mice in the treatment group were injected into the tail vein twice a week at doses of 1 mg/kg and 3 mg/kg for a total of three weeks. The tumor volume was monitored. The tumor volume calculation method was: tumor volume (mm$^3$)=½×(a×b$^2$) (wherein a represented the long diameter and b represented the short diameter).

Figure 22:
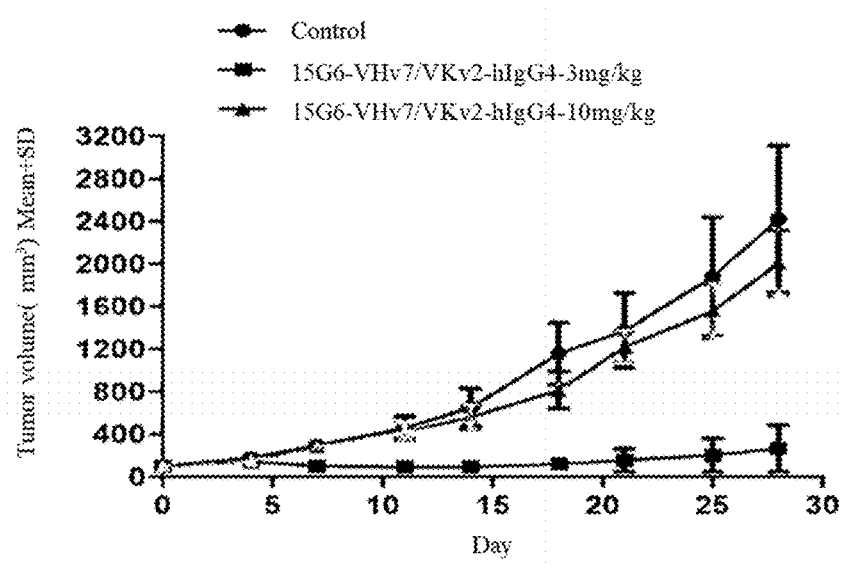
FIG. 22. The anti-tumor effect of humanized CD47 monoclonal antibody in PDX mouse model of CD47 high expression lung cancer.

The results were shown in FIG. 22. The 3 mg/kg treatment group showed significant tumor inhibition, and the endpoint relative tumor inhibition rate TGI (%) was 88.62%; the 1 mg/kg treatment group did not show significant tumor inhibition after the end of the administration. The endpoint relative tumor inhibition rate TGI (%) was 10.71%.

22. Toxicity Exploratory Test of Humanized CD47 Monoclonal Antibody Given to Cynomolgus Monkeys by Repeated Intravenous Infusion In this experiment, 4 cynomolgus monkeys, half male and half female, were randomly divided into 2 groups, namely high-dose and low-dose groups. It was administered once a week for 5 times in total, namely on D1, D8, D15, D22 and D29. The administration dosage and concentration of the animals in each group are shown in the following table, intravenous injection, administration volume is 10 ml/kg.

| Group | First administration Dosage(mg/kg) | Maintenance administration (2nd~5th times) Dosage(mg/kg) | Number of animals Male | Number of animals Female |
|---|---|---|---|---|
| 1 low-dose | 3 | 150 | 1 | 1 |
| 2 high-dose | 3 | 250 | 1 | 1 |

During the experiment, no animals were dead or dying; there were no changes in the clinical observations, body weight, body temperature, electrocardiogram, blood coagulation function, etc. of the two groups of animals. During the experiment, compared with the value before administration, the changes in blood cell counts of the two groups of animals were mainly the reduction of red blood cells related indicators (RBC, HGB, HCT), and the specific manifestations were: 2 to 4 hours after the first administration (D1), The RBC, HGB, and HCT of the animals in each treatment group significantly decreased, and then decreased continuously from D2 to D7. 2 to 4 hours after the second administration (D8), the above indicators continued to decrease to the lowest level, and then recovery was observed. After each administration (3th~5th times), the decline of the above indicators and subsequent recovery can be observed. During the test, HGB did not decrease below 90 g/L. After the end of administration, the RBC, HGB, and HCT of each group showed a clear recovery trend. Until the 31th day after the last administration (D60), the RBC, HGB, and HCT of the animals in the low and high dose groups were basically recovered.

23. Toxicokinetic Studies

About 1 ml of blood from the vein of the hind limbs of the cynomolgus monkey was collected. The blood sample was not anticoagulated. The serum was separated within 2 hours after the blood was collected. The drug concentration in blood was detected by ELISA method with coated human CD47 antigen, and the second antibody was Anti-Human IgG (Fc specific)-Peroxidase antibody produced in goat. The pharmacokinetic parameters were calculated by Winnonlin software, shown in the table below.

| Dosage (mg/kg) | Number of animals | $T_{1/2}$ h | $T_{max}$ h | $C_{max}$ mg/ml | $AUC_{0-t}$ h*mg/ml | CL ml/h/kg |
|---|---|---|---|---|---|---|
| 150 | 2 | 231.25 | 4 | 5.65 | 1418.09 | 0.096 |
| 250 | 2 | 179.35 | 2 | 9.08 | 1895.92 | 0.1245 |

The invention claimed is:

1. A CD47-targeting antibody or a functional fragment thereof, comprising a heavy chain CDR1 consisting of amino acid sequence SEQ ID NO: 102, a heavy chain CDR2 consisting of amino acid sequence SEQ ID NO: 103, a heavy chain CDR3 consisting of amino acid sequence SEQ ID NO: 104, a light chain CDR1 consisting of amino acid sequence SEQ ID NO: 157, a light chain CDR2 consisting of amino acid sequence SEQ ID NO: 158, and a light chain CDR3 consisting of amino acid sequence SEQ ID NO: 159.

2. The antibody or a functional fragment thereof according to claim 1, comprising:

(i) a heavy chain variable region consisting of amino acid sequence SEQ ID NO:101, and a light chain variable region consisting of amino acid sequence SEQ ID NO:156;

(ii) a heavy chain variable region consisting of amino acid sequence SEQ ID NO:101, and a light chain variable region consisting of amino acid sequence SEQ ID NO:161;

(iii) a heavy chain variable region consisting of amino acid sequence SEQ ID NO:106, and a light chain variable region consisting of amino acid sequence SEQ ID NO:156;
(iv) a heavy chain variable region consisting of amino acid sequence SEQ ID NO:106, and a light chain variable region consisting of amino acid sequence SEQ ID NO:161;
(v) a heavy chain variable region consisting of amino acid sequence SEQ ID NO:111, and a light chain variable region consisting of amino acid sequence SEQ ID NO:156;
(vi) a heavy chain variable region consisting of amino acid sequence SEQ ID NO:111, and a light chain variable region consisting of amino acid sequence SEQ ID NO:161;
(vii) a heavy chain variable region consisting of amino acid sequence SEQ ID NO:116, and a light chain variable region consisting of amino acid sequence SEQ ID NO:156;
(viii) a heavy chain variable region consisting of amino acid sequence SEQ ID NO:116, and a light chain variable region consisting of amino acid sequence SEQ ID NO:161;
(ix) a heavy chain variable region consisting of amino acid sequence SEQ ID NO:121, and a light chain variable region consisting of amino acid sequence SEQ ID NO:156;
(x) a heavy chain variable region consisting of amino acid sequence SEQ ID NO:121, and a light chain variable region consisting of amino acid sequence SEQ ID NO:161;
(xi) a heavy chain variable region consisting of amino acid sequence SEQ ID NO:131, and a light chain variable region consisting of amino acid sequence SEQ ID NO:156;
(xii) a heavy chain variable region consisting of amino acid sequence SEQ ID NO:131, and a light chain variable region consisting of amino acid sequence SEQ ID NO:161; or
(xiii) a heavy chain variable region consisting of amino acid sequence SEQ ID NO:151, and a light chain variable region consisting of amino acid sequence SEQ ID NO:161.

3. A CD47-targeting antibody or a functional fragment thereof, comprising a heavy chain CDR1 consisting of amino acid sequence SEQ ID NO:82, a heavy chain CDR2 consisting of amino acid sequence SEQ ID NO:83, a heavy chain CDR3 consisting of amino acid sequence SEQ ID NO:84, a light chain CDR1 consisting of amino acid sequence SEQ ID NO:87, a light chain CDR2 consisting of amino acid sequence SEQ ID NO:88, and a light chain CDR3 consisting of amino acid sequence SEQ ID NO:89.

4. A CD47-targeting antibody or a functional fragment thereof, comprising a heavy chain CDR1 consisting of amino acid sequence SEQ ID NO:102, a heavy chain CDR2 consisting of amino acid sequence SEQ ID NO:103, a heavy chain CDR3 consisting of amino acid sequence SEQ ID NO:104, a light chain CDR1 consisting of amino acid sequence SEQ ID NO:157, a light chain CDR2 consisting of amino acid sequence SEQ ID NO:158, and a light chain CDR3 consisting of amino acid sequence SEQ ID NO:159.

5. The antibody or a functional fragment thereof according to claim 2, comprising a heavy chain variable region consisting of amino acid sequence SEQ ID NO:121, and a light chain variable region consisting of amino acid sequence SEQ ID NO:156.

6. The antibody or a functional fragment thereof according to claim 2, comprising a heavy chain variable region consisting of amino acid sequence SEQ ID NO:101, and a light chain variable region consisting of amino acid sequence SEQ ID NO: 156.

7. The antibody or a functional fragment thereof of claim 1, wherein the antibody or a functional fragment thereof inhibits the interaction of CD47 and SIRPα.

8. The antibody or a functional fragment thereof of claim 7, wherein the antibody or a functional fragment thereof is humanized.

9. The antibody or a functional fragment thereof of claim 7, wherein the antibody or a functional fragment thereof is IgG1 type or IgG4 type.

10. A nucleic acid molecule encoding the antibody or a functional fragment thereof of claim 1, or a vector comprising the nucleic acid molecule, or a cell comprising the vector, or a pharmaceutical composition comprising the antibody or a functional fragment thereof, or the nucleic acid encoding same and a pharmaceutically acceptable carrier.

11. The nucleic acid molecule, or the vector, or the cell, or the pharmaceutical composition of claim 10, comprising
(i) a heavy chain variable region consisting of amino acid sequence SEQ ID NO:101, and a light chain variable region consisting of amino acid sequence SEQ ID NO:161;
(ii) a heavy chain variable region consisting of amino acid sequence SEQ ID NO:106, and a light chain variable region consisting of amino acid sequence SEQ ID NO:156;
(iii) a heavy chain variable region consisting of amino acid sequence SEQ ID NO:106, and a light chain variable region consisting of amino acid sequence SEQ ID NO:161;
(iv) a heavy chain variable region consisting of amino acid sequence SEQ ID NO:111, and a light chain variable region consisting of amino acid sequence SEQ ID NO:156;
(v) a heavy chain variable region consisting of amino acid sequence SEQ ID NO:111, and a light chain variable region consisting of amino acid sequence SEQ ID NO:161;
(vi) a heavy chain variable region consisting of amino acid sequence SEQ ID NO:116, and a light chain variable region consisting of amino acid sequence SEQ ID NO:156;
(vii) a heavy chain variable region consisting of amino acid sequence SEQ ID NO:116, and a light chain variable region consisting of amino acid sequence SEQ ID NO:161;
(viii) a heavy chain variable region consisting of amino acid sequence SEQ ID NO:121, and a light chain variable region consisting of amino acid sequence SEQ ID NO:156;
(ix) a heavy chain variable region consisting of amino acid sequence SEQ ID NO:121, and a light chain variable region consisting of amino acid sequence SEQ ID NO:161;
(x} a heavy chain variable region consisting of amino acid sequence SEQ ID NO:131, and a light chain variable region consisting of amino acid sequence SEQ ID NO:156;
(xi) a heavy chain variable region consisting of amino acid sequence SEQ ID NO:131, and a light chain variable region consisting of amino acid sequence SEQ ID NO:161;

(xii) a heavy chain variable region consisting of amino acid sequence SEQ ID NO:151, and a light chain variable region consisting of amino acid sequence SEQ ID NO:161.

12. A nucleic acid molecule, or a vector, or a cell, or a pharmaceutical composition comprising the antibody of claim 3.

13. A nucleic acid molecule, or a vector, or a cell, or a pharmaceutical composition, comprising the antibody of claim 4.

14. The nucleic acid molecule, or the vector, or the cell, or the pharmaceutical composition, of claim 12, wherein the heavy chain variable region consists of amino acid sequence SEQ ID NO:81, and the light chain variable region consists of amino acid sequence SEQ ID NO:86.

15. The nucleic acid molecule, or the vector, or the cell, or the pharmaceutical composition of claim 11, wherein the heavy chain variable region consists of amino acid sequence SEQ ID NO:101, and the light chain variable region consists of amino acid sequence SEQ ID NO:156.

16. The nucleic acid molecule, or the vector, or the cell, or the pharmaceutical composition according to claim 10, wherein the antibody or a functional fragment thereof inhibits the interaction of CD47 and SIRPα.

17. The nucleic acid molecule, or the vector, or the cell, or the pharmaceutical composition of claim 16, wherein the antibody or a functional fragment thereof is humanized.

18. The nucleic acid molecule, or the vector, or the cell, or the pharmaceutical composition of claim 16, wherein the antibody or a functional fragment thereof is IgG1 type or IgG4 type.

19. A method of treating a disease associated with abnormal production of CD47 in a mammal, comprising the step of administering to the mammal a therapeutically effective amount of the antibody or functional fragment thereof according to claim 1, or a nucleic acid molecule encoding the antibody or a functional fragment thereof, or a vector comprising the nucleic acid molecule, or a cell comprising the vector or a pharmaceutical composition comprising the antibody or a functional fragment thereof, or the nucleic acid encoding same and a pharmaceutically acceptable carrier, wherein the disease is cancer.

20. The method according to claim 19, wherein the cancer is a hematological cancer, and the hematological cancer is selected from lymphoma and myeloma, wherein the myeloma is selected from multiple myeloma (MM), giant cell myeloma, heavy chain myeloma, and light chain or Bence-Jones myeloma.

21. The method according to claim 19, wherein the solid tumor is selected from breast tumors, ovarian tumors, lung tumors, pancreatic tumors, prostate tumors, melanomas, colorectal tumors, lung tumors, head and neck tumors, bladder tumors, esophageal tumors, liver tumors, and kidney tumors.

22. The method according to claim 19, wherein the disease is atherosclerosis.

* * * * *